US007598417B2

(12) United States Patent
Chow et al.

(10) Patent No.: US 7,598,417 B2
(45) Date of Patent: Oct. 6, 2009

(54) SUBSTITUTED FLUOROETHYL UREAS AS ALPHA 2 ADRENERGIC AGENTS

(75) Inventors: Ken Chow, Newport Coast, CA (US); Wenkui K. Fang, Irvine, CA (US); Evelyn G. Corpuz, Irvine, CA (US); Daniel W. Gil, Corona Del Mar, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/058,219

(22) Filed: Mar. 28, 2008

(65) Prior Publication Data

US 2008/0255239 A1 Oct. 16, 2008

Related U.S. Application Data

(60) Provisional application No. 60/911,442, filed on Apr. 12, 2007.

(51) Int. Cl.
*C07C 275/06* (2006.01)
*A61K 31/17* (2006.01)
(52) U.S. Cl. .................. 564/57; 514/588; 514/443; 514/464; 549/57; 549/462
(58) Field of Classification Search .................. 564/57; 514/588, 443, 464; 549/57, 412
See application file for complete search history.

(56) References Cited

FOREIGN PATENT DOCUMENTS

| DE | 2812578 | 10/1978 |
|---|---|---|
| WO | WO 92/0073 | 1/1992 |

OTHER PUBLICATIONS

Johnston et al, Journal of Medicinal Chemistry, 1971, vol. 14, No. 7, pp. 600-614.*
Adamczyk, Maciej; Watt, David S.; Netzel, Daniel A.: Synthesis of Biological Markers in Fossil Fuels, 2. Synthesis and 13C NMR Studies of Substituted Idans and Tetralins. J. Org. Chem. 1984,49,4226-4237.
Adcock, W. et al.: Conformational Consequences of Metallo-Methyl Interactions: A 13C Nuclear Magnetic Resonance Study. J. Organometallic Chem. 1975, 102; 297-311.
Adlerova et al. Synthetische Versuche In Der Gruppe Der Ostrogenen Hormone XIV. CCCAK; Collect. Czech. Chem. Commun. 1958, 23, 681-688.
Askam, V.; et al.: Ethyl 6-Acetylindane-1-carboxylate. J. Chem. Soc. 1954, 4691-4693.
Baldwin, Steven W.; Tomesch, John C.: Total Synthesis of dl-Cyclosativene by Cationic Olefinic and Acetylenic Cyclizations. J. Org. Chem. 1980, 45, 1455-1462.
Barnier, Jean-Pierre; et al.: Enzymatic Resolution of Cyclopropanols, An Easy Access to Optically Active Cyclohexanones Possessing an α-Quaternary Chiral Carbon.Tetrahedron: Asymmetry 1999, 10,1107-1118.

Bartmann, W.; et al.: Synthesis of Di- and Tetraalkyl-3-piperazinoisoquinolines and Related Compounds as Potential Antidepressant Agents. J. Het. Chem. 1987, 24, 677-682.
Berube, Gervais; et al.: A stereocontrolled intramolecular cycloaddition — sigmatropic rearrangement approach to a tricyclo[7.4.0$^{1,6}$.0$^{1,10}$]tridecane precursor for (±) gascardic acid. Can. J. Chem. 1991, 69, 77-83.
Borne, R.F. et al.: Conformational Analogues of Antihypertensive Agents Related to Guanethidine. J. Med. Chem. 1977, 20, 771-776.
Braun, H.; et al: Asymmetric Synthesis of Primary Amines From Alkenes and Chiral Chloronitroso Sugar Derivatives. Tetrahedron 1991, 47, 3313-3328.
Bunneft, J. F.; Skorcz, J.A.: Homocyclic Ring Closures via Benzyne Intermediates. A New Synthesis I of 1-Substituted Benzocyclobutenes. J. Org. Chem. 1962, 27, 3836-3843.
Burnham, J.W.; et al.: Effects of Alkyl Substituents in the Chromic Acid Oxidation of Tetrealins. J. Org. Chem. 1974, 39, 1416-1420.
Callis, David J.; et al.: A Tandem Horner-Emmons Olefination-Conjugate Addition Approach to the Synthesis of 1,5-Disubstituted-6-azabicyclo[3.2.1]octanes Based on the AE Ring Structure of the Norditerpenoid Alkaloid Methyllycaconitine. J. Org. Chem. 1996, 61, 4634-4640.
Cannon, Joseph G.; et al.: Comparison of Biological Effects of N-Alkylated Congeners of aPhenethylamine Derived from 2-Aminotetralin, 2-Aminoindan, and 6-Aminobenzocycloheptene. J. Med. Chem. 1980, 23, 745-749.
Caprathe, Bradley W.; et al.: Dopamine Autoreceptor Agonists as Potential Antipsychotics. 3. 6-Propyl-4,5,5a,6,7,8-hexahydrothiazolo[4,5-f]quinolin-2-amine. J. Med. Chem. 1991, 34, 2736-2746.
Carrea, Giacomol; et al.: Lipase mediated resolution of 2-cyclohexen-1-ols as chiral building blocks en route to eburnane alkaloids. Tetrahedron: Asymmetry 1992, 3, 775-784..
Cauquil-Caubere, lsoline; et al.: New structures able to prevent the inhibition by hydroxyl radicals of glutamate transport in cultured astrocytes. Eur. J. Med. Chem. Chim Ther. 1998, 33, 867-878.
Clemo, G. R.; et al.: Indene Series. Part I. A Synthesis of 1:2:3:8-Tetrahydro-1-ketocyclopent[a]diene J. Chem. Soc. 1951, 863-867.
Colette; Perrot: Organische und biologische Chemie - Chimie organique et chimie biologique Etude de l'action de l'oxyde d'azote (III) sur l'indène et ses homologues Helv. Chim. Acta 1977, 60, 2089-2094.
Cope, Al.; et al.: Cyclic Polylefins. XLI. Reaction of Acetyl Bromide and Propionyl Chloride with Cycloocatatetraene J. Am. Chem. Soc. 1957, 79, 240-243.
Haadsma-Svensson; et al.: Dopamine D3 Receptor Antagonists. 1. Synthesis and Structure-Activity Relationships of 5,6-Dimethoxy-N-alkyl- and N-Alkylaryl-Substituted 2-Aminoindans J. Med. Chem. 2001,44, 4716-4732.
Hahn, R.C.; et al.: Cyclopropyl aromatic chemistry. I. Ultraviolet spectra of certain cyclopropyl aromatic systems. J. Am. Chem. Soc. 1971, 93, 5816-5820.
Houghton, Roy P.; et al.: Reactions of Coordinated Ligands. Part 9. Chromium(0)-Promoted Intramolecular Nucleophilic Substitution of an Aryl Halide: A Preparation of Chroman. J. Organomet. Chem. 1983, 259, 183-188.

(Continued)

*Primary Examiner*—Shailendra Kumar
(74) *Attorney, Agent, or Firm*—John E. Wurst; Allergan, Inc.

(57) ABSTRACT

The present patent application is directed to novel fluoroethyl urea compounds and compositions and their therapeutic use in the treatment of pain and other conditions.

21 Claims, No Drawings

OTHER PUBLICATIONS

Houghton, Roy P.; et al.: Reactions of co-ordinated ligands. Part 10. Rhodium-catalysed cyclisation of 3-(2-fluorophenyl)propanols to chromans. J. Chem. Soc. Perkin Trans. 1 1984, 5, 925-931.

Houghton, Roy P.; Shervington, Leroy A.: Preparation of Some Chromans Substituted at the 3- or 4- Position by an Aryl of Benzyl Group, by the Rhodium-caralysed Intramolecular Nucleophilic Substitution of the Corresponding 3-(2-Fluorophenyl)Propan-1-ols. J. Chem. Res. Miniprint 1989, 8, 1872-1892.

Hua, Duy H.; et al.: A One-Pot Condensation of Pryones and Enals. Synthesis of 1H, 7H-5a,6,8,9-Tetrahydro-1-oxopyrano[4,3-b][1]benzopyrans. J. Org. Chem. 1997, 62, 6888-6896.

Immer, H.; Bagli, J.F.: Syntheses of Medium-Ring Benzoic Acid Lactones. J. Org. Chem. 1968, 33, 2457-2462.

Ito, Satoru; et al.: Preparation of Chiral Allylic Alcohols Using Rhizopus Nigricans. Use of the Harada-Nakanishi Exciton Chirality Method for Verifying Configurational Assignments of Allylic Alcohols. Can. J. Chem. 1987, 65, 574-582.

Ward, Dale E.; et al.: "Chemoselective Reductions with Sodium Borohydride." Can. J. Chem. 1989, 67, 1206-1211.

Wolfe, John P.; et al: Intramolecular Palladium-Catalyzed Aryl Amination and Aryl Amidation. Tetrahedron 1996, 52, 7525-7546.

Zh. Obshch. Khim. 1964, 34, 1581.

Zh. Obshch. Khim. 1960, 30, 3692.

Zhang, Xiaoyan; et al.: Medetomidine Analogs as a-Adrenergic Ligands. 3. Synthesis and Biological Evaluation of a New Series of Medetomidine Analogs and Their Potential Binding Interactions with $\alpha$-Adrenoceptors Involving a "methyl Pocket". J. Med. Chem. 1997, 40, 3014-3024.

Johnson, M. P.; et al.: Synthesis and Pharmacological Examination of 1-(3-Methoxy-4-methylphenyl)-2-aminopropane and 5-Methoxy-6-methyl-2-aminoindan: Similarities to 3,4-(Methylenedioxy)methamphetamine (MDMA). J. Med. Chem. 1991, 34, 1662-1668.

Johnston, Thomas; et al.: Synthesis of Analogues of N-(2-Chloroethyl)-N'-(trans-4-methylcyclohexyl)-N-nitrosourea for Evaluation as Anticancer Agents. Journal of Medicinal Chemistry, 1977, vol. 20, No. 2 p. 279-290.

Ksander, Gary M.; et al.: Ortho-Substituted Benzofused Macrocyclic Lactams as Zinc Metalloprotease Inhibitors J. Med. Chem. 1997, 40, 495-505.

Kuiban et al.: Investigations in the Field of Derivatives of Tetrahydronaphthalene. J. Gen. Chem. USSR (Engl. Transl.) 1964, 34, p. 1581-1586.

Kuwahara, Shigefunmi; et al.: Synthesis of Robinal, a Highly Conjugated Monoterpenoid From the Mite, Rhizoglyphus robini. Biosci. Biotechnol. Biochem. 1992, 56, 1510-1511.

Landsiedel-Maier; et al.: Structure Activity Relationship of Homochiral 7-Substituted 1-Aminoindans as 5-HT1A Receptor Ligands. Arch. Pharm. (Weinheim Ger.) 1998, 331, 59-71 (Abstract Only).

Laurent, Andre; et al.: J. Chem. Res. Miniprint 1984, 11,3165-3194.

Leblac, Y.; et al.: Amination of olefinic compounds with bis(2,2,2-trichloroethyl) azodicarboxylate J. Org. Chem. 1991, 56, 1971-1972.

Lewschina; Kolodkina: Bis ($\beta$-Chloroethyl)-Amines of Bicyclic Compounds. J. Gen. Chem. USSR (Engl. Transl.) 1960, 30, 3656.

Mattson, Ronald J.; et al.: Indanyl Piperazines as Melatonergic MT2 Selective Agents. Bio. Org. Med. Chem. Lett. 2003, 13, 1199-1202.

Mizuno, Masanori; et al.: Efficient method for the one-pot azidation of alcohols using bis(p-nitrophenyl) phosphorazidate. Chem Commun. 1997, 22, 2165-2166.

Musso, David L.; et al.: Indanylidenes. 1. Design and Synthesis of (E)-2(4,6-Difluror-1-indanylidene)acetamide, a Potent, Centrally Acting Muscle Relaxant with Antiiflammatory and Analgesic Activity. J. Med. Chem. 2003, 46, 399-408.

Nakada et al.: Synthesis and Insecticidal Activity of 4-Substituted 1-Indayl Chrysanthemates Agric. Biol. Chem. 1978, 42, 1365-1372.

Nakamura, Y.; et al.; Photochemical Synthesis, Conformational Analysis, and Transformation of [60]Fullerene-o-quinodimethane Adducts Bearing a Hydroxy Group. J. Org. Chem. 2002, 67, 1247-1252.

Nguy, Nim Ming; et al.: Synthesis and Reactivity of 6- and 7-Methoxyindano[1,2-b]aziridines J. Org. Chem. 1987, 52, 1649-1655.

Novak; Protiva CCCCAK; Collect. Czech Chem. Commun. 1962, 27, 2413, 2416.

Organ, Michael. G.; et al.: Ni-Catalyzed Cross Coupling of Alkoxide-Containing Vinyl Halides with Grignard Reagents. A "One-Pot" Synthesis of 2-[(Trimethylsilyl]-2-propen-1-yl Acetate. J. Org. Chem. 1997, 62, 1523-1526.

Patent; Eli Lilly and Co.; Indianapolis; Ind. (V.ST.A.); 1978; Chem. Abstr., 90, 54730.

Pau, Amedeo; et al.: Synthesis of Amides with anti-inflammatory and analgesic activities Farmaco 1997, 52, 93-98.

Perrone, Roberto; et al.: 1-Aryl-4-[(1-tetralinyl)alkyl]piperazines: Alkylamido and Alkylamino Derivatives. Synthesis, 5-$HT_{1A}$ Receptor Affinity, and Selectivity. J. Med. Chem. 1996, 39, 3195-3202.

Ranade, V.S.; et al.: Functional-Group-Directed Diastereoselective Hydrogenation of Aromatic Compounds J. Org. Chem. 1999, 64, 8862-8867.

Robert R. Ruffolo, Jr., $\alpha$-Adrenoreceptors: Molecular Biology, Biochemistry and Pharmacology, (Progress in Basic and Clinical Pharmacology series, Karger, 1991.

Russell, G.A.; et al.: Aliphatic semidiones. XV. 2,3-Semidiones derived from the bicyclo[n.1.0]alkanes J. Am. Chem. Soc. 1971, 93, 1452-1466.

Sarges et al.: 5,8-Disubstituted 1-aminotetralins. Class of compounds with a novel profile of central nervous system activity J. Med. Chem. 1973, 16, 1003, 1004.

SciFinder, Dec. 28, 2006.

Seidl, G.; et al.: Umsetzungen Der 1:2-Benzocyclenyl-3-Methylamine Mit Salpetriger Saure. Tetrahedron 1964, vol. 20, pp. 633-640.

Shoji, Mitsuru; et al.: Different Reaction Modes for the Oxidative Dimerization of Epoxyquinols and Epoxyquinones. Importance of Intermolecular Hydrogen-Bonding J. Org. Chem. 2004, 69, 1548-1556.

Simchen, G.; Kraemer, W.: Eine Neue Isochinolinsynthese. Chem. Ber. 1969, 102, 3656-3665.

Sircar, I.; Cardiotonic agents. 4. Synthesis and biological evaluation of N-substituted 2,4,4a,5-tetrahydro-3H-indeno[1,2-c]pyridazin-3-ones: rigid structures derived from CI-930 and analogs J. Med. Chem. 1986, 29, 2142-2148.

Siscovic, E. et al.: Synthesis of Some Optically Active Substituted Indanes. Indian J. Chem. 1968, 6, 400-401.

Srikrishna, A.; et al.: A Radical Cyclisation Based Cyclopentenone Annulation of Allyl Alcohols Tetrahedron: Asymmetry 2003, 14, 2978-2984.

Stipanovic, B.; Pines, H.: Base-Catalyzed reactions. XXXIII. Sodium- and Potassium-Catalyzed Reactions of Methylnaphalenes with Ethylene. J. Org, Chem. 1969, 34, 2106-2113.

Staab, Heinz A.; et al.: Photoinduced Electron-Transfer in Porphyrin-Acceptor Cyclophanes, 19 Pyromellitic Diimide-Porphyrin Cyclophanes: Syntheses, Transannular Interactions, and Stucture Analysis. J. Org. Chem. 1999, 6, 1459-1470.

Stratford, E.S. et al.: Potential Hypocholesteremic Derivatives of Styrylacetic Acid II: cis- and trans-3-Methyl-4-phenyl-3-butenoic Acid Analogs. J. Pharm. Sci. 1978, 67, 80-83.

Thummel, Randolph P.; et al.: Polyaza cavity-shaped molecules. Annelated derivatives of 2-(2'-pyridyl)-1,8-naphthyridine and 2,2'-bi-1,8-naphthyridine J. Org. Chem. 1984, 49, 2208-2212.

Tombari, D.G.; et al.: Preparation of 2(2-Hydroxymethyl-6-Methyl)Phenylethanol, Org. Prep. Proced. Int. 1995,27,671-674.

Vaccaro, W.; et al.: Inhibitors of Acyl CoA:Cholesterol Acyltransferase J. Med. Chem. 1996, 39, 1704-1719.

Vejdelek, Z.J.; et al.: Benzocycloheptenes and Heterocyclic Analogues as Potential Drugs. I. N-Substituted Derivatives of 5-Amino-6,7,8,9-Tetrahydro-5H-Benzocycloheptene and Some Other Compounds. CCCCAK; Collect. Czech. Chem. Commun. 1971, 36, 1611-1623.

\* cited by examiner

SUBSTITUTED FLUOROETHYL UREAS AS ALPHA 2 ADRENERGIC AGENTS

CROSS REFERENCE TO RELATED APPLICATIONS

This application claims the benefit of U.S. Provisional Application Ser. No. 60/911,442 filed Apr. 12, 2007, which is hereby incorporated by reference in its entirety.

DESCRIPTION OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting $\alpha$-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Disclosed herein is a compound having the formula

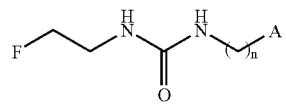

or a pharmaceutically acceptable salt thereof,
wherein n is 0 or 1; and
A is 5 to 7-membered cycloalkenyl optionally fused to an aromatic ring;
wherein A has 0, 1, 2, 3, or 4 substituents;
said substituents each independently consisting of: a moiety consisting of from 0 to 8 carbon atoms, 0 or 1 nitrogen atoms, 0 or 1 oxygen atoms, 0 or 1 sulfur atoms, 0 to 3 fluorine atoms, and from 0 to 22 hydrogen atoms; F; Cl; Br; or I;
provided that A is not unsubstituted hexenyl.

These compounds are agonists of alpha 2 adrenergic receptors in mammals, and are thus useful for modulating the $\alpha_2$ adrenergic receptors in mammals. For example, they are useful to alleviate chronic pain, allodynia, muscle spasticity, diarrhea, neuropathic pain, visceral pain and other diseases and conditions. Many of these compounds are also specific for either the $\alpha$2A, a2B, or $\alpha$2C receptor, or are active at only two of those three.

Since n is 0 or 1, compounds of the structures shown below are possible.

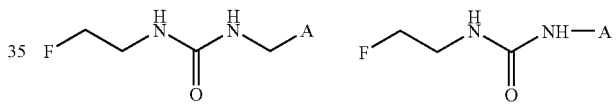

A is 5 to 7-membered cycloalkenyl optionally fused to an aromatic ring. Cycloalkenyl is a carbocycle with a double bond. Thus, 5 to 7-membered cycloalkenyl includes the structures depicted below.

structure:

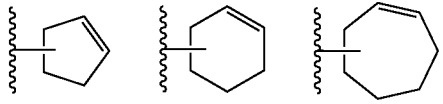

name: cyclopentenyl cyclohexenyl cycloheptenyl

That A is "optionally fused to an aromatic ring" means that A may be monocyclic cycloalkenyl such as one of the structures above, or A may be fused to an aromatic ring such as phenyl, thienyl, furyl, pyridinyl, and the like. Thus, hypothetical examples of cycloalkenyl fused to an aromatic ring are shown below. Substituted versions of each of these structures are also contemplated.

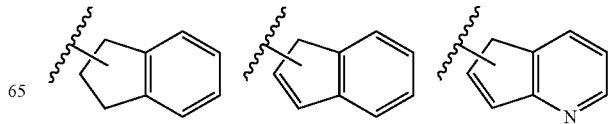

-continued

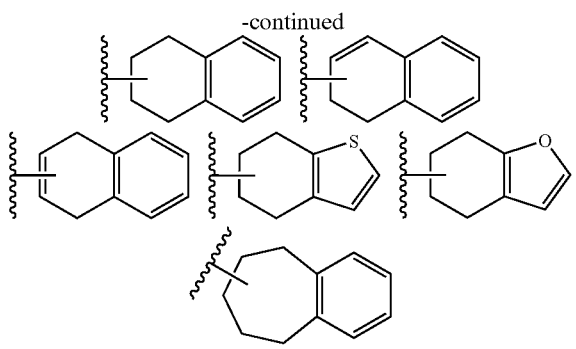

In these structures, the point of attachment occurs at a carbon that is solely part of the cycloalkenyl, i.e. the attachment is not to the aromatic ring. The structures shown below are exemplary. Substituted versions of each of these structures are also contemplated.

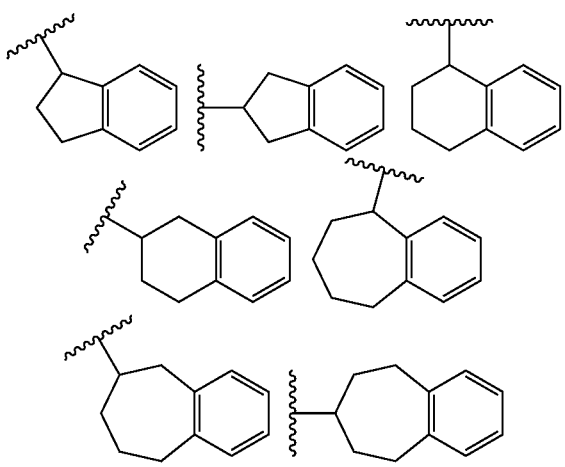

A has 0, 1, 2, 3, or 4 substituents. In other words, 0, 1, 2, 3, or 4 hydrogens on the cycloakenyl ring or on an aryl ring fused to the cycloalkenyl, such as one of the structures depicted above, may be replaced with a moiety that is not hydrogen. Each substituent may be the same as one or more of any other substituents, or may be different from all other substituents. Each substituent is a moiety consisting of from 0 to 8 carbon atoms, 0 or 1 nitrogen atoms, 0 or 1 oxygen atoms, 0 or 1 sulfur atoms, 0 to 3 fluorine atoms, and from 0 to 22 hydrogen atoms; or a substituent is F; Cl; Br; or I.

Examples of substituents include, but are not limited to:

Hydrocarbyl having from 1 to 8 carbon atoms including, but not limited to:

a. alkyl having from 1 to 8 carbon atoms, including, but not limited to:
  linear alkyl, e.g. methyl, ethyl, n-propyl, n-butyl, n-pentyl, n-hexyl, etc.,
  branched alkyl, e.g. iso-propyl, t-butyl and other branched butyl isomers, branched pentyl isomers, etc.,
  cycloalkyl, e.g. cyclopropyl, cyclobutyl, cyclopentyl, cyclohexyl, etc.,
  combinations of linear, branched, and/or cycloalkyl;
b. alkenyl having from 1 to 8 carbon atoms, e.g. hydrocarbyl having 1 or more double bonds, including linear, branched, or cycloalkenyl c. alkynyl having from 1 to 8 carbon atoms, e.g. hydrocarbyl having 1 or more triple bonds, including linear, branched, or cycloalkenyl;
d. combinations of alkyl, alkenyl, and/or alkynyl
   alkyl-CN having from 1 to 7 carbon atoms;
ether substituents, including O-alkyl, alkyl-O-alkyl, and the like, having from 1 to 8 carbon atoms;
thioether substituents, including S-alkyl, alkyl-S-alkyl, and the like, having from 1 to 8 carbon atoms;
amine substituents, including $NH_2$, NH-alkyl, N-alkyl$^1$alkyl$^2$ (i.e., alkyl$^1$ and alkyl$^2$ are the same or different, both attached to N), alkyl-$NH_2$, alkyl-NH-alkyl, alkyl-N-alkyl$^1$alkyl$^2$, and the like;
ester substituents, including $CO_2$-alkyl, $CO_2$-phenyl, etc., having from 1 to 8 carbon atoms;
other carbonyl substituents, including aldehydes, ketones, and the like;
phenyl, provided that the ring and any substituents remain with the constraints defined herein;
fluorocarbons or hydrofluorocarbons such as $CF_3$, $CH_2CF_3$, etc.; and
CN;
combinations of the above are also possible, subject to the constraints defined;
Alternatively, a substituent may be F, Cl, Br, or I.

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counterion of said salt, i.e. the ion that is not covalently bonded to the remainder of the molecule is not counted for the purposes of the number of heavy atoms in a substituent. Thus, for example, the salt —$CO_2^-Na^+$ is a stable substituent consisting of 3 heavy atoms, i.e. sodium is not counted. In another example, the salt —$NH(Me)_2^+Cl^-$ is a stable substituent consisting of 3 heavy atoms, i.e. chlorine is not counted.

A is not unsubstituted hexenyl, e.g.

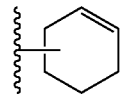

with no substituents.

In one embodiment A is cyclopentenyl optionally fused to an aromatic ring.

In one embodiment A is cyclohexenyl optionally fused to an aromatic ring.

In one embodiment A is tetrahydronaphthylenyl.

In one embodiment A is cycloheptenyl optionally fused to an aromatic ring.

In one embodiment A has 0, 1, or 2 substituents.

In one embodiment the substituents are independently $C_{1-3}$ alkyl, $C_{1-3}$ alkoxy, F, Cl, Br, I, or $NH_2$.

Tautomers of these compounds are possible. If a structure is depicted in any claim, any tautomer of that structure is considered to be within the scope of the claim unless specifically disclaimed. Examples of tautomers for these compounds are depicted below.

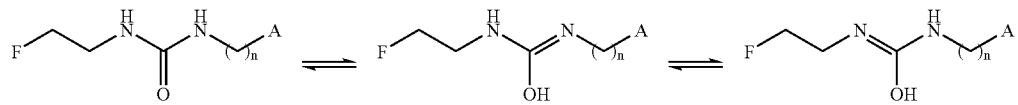

Another embodiment is a compound having the formula

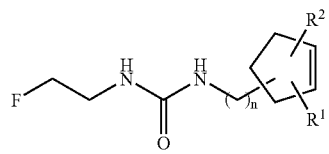

or a pharmaceutically acceptable salt thereof;

wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I.

Another embodiment is a compound having the formula

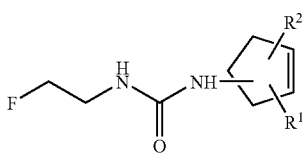

or a pharmaceutically acceptable salt thereof;

wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I.

Another embodiment is a compound having the formula

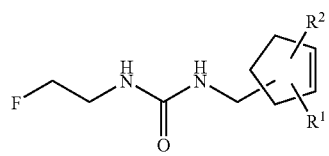

or a pharmaceutically acceptable salt thereof;

wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I.

Another embodiment is a compound having the formula

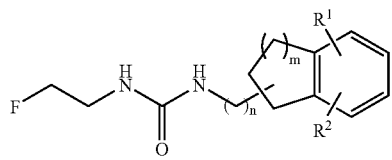

or a pharmaceutically acceptable salt thereof;

wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and m is 1, 2, or 3.

Another embodiment is a compound having the formula

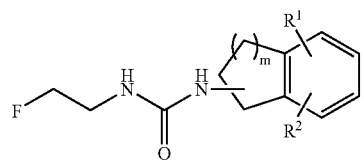

or a pharmaceutically acceptable salt thereof;

wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and m is 1, 2, or 3.

Another embodiment is a compound having the formula

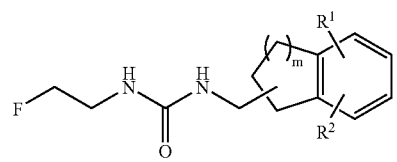

or a pharmaceutically acceptable salt thereof;

wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and m is 1, 2, or 3.

Another embodiment is a compound having the formula

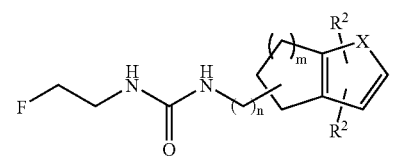

or a pharmaceutically acceptable salt thereof;

wherein X is S, N, or O;

$R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and m is 1, 2, or 3.

Another embodiment is a compound having the formula

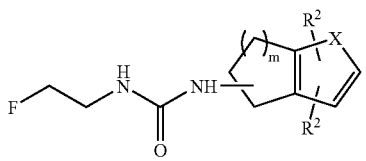

or a pharmaceutically acceptable salt thereof;
wherein X is S, N, or O;
$R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and m is 1, 2, or 3.

Another embodiment is a compound having the formula

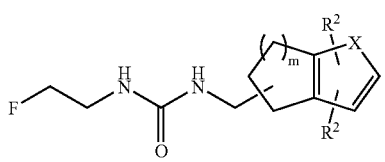

or a pharmaceutically acceptable salt thereof;
wherein X is S, N, or O;
$R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and m is 1, 2, or 3.

One embodiment is a method of treating pain comprising administering a compound disclosed herein to a mammal in need thereof.

Another embodiment is use of a compound disclosed herein in the manufacture of a medicament for the treatment of pain.

Another embodiment is a dosage form comprising a compound disclosed herein.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid or another salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Unless stereochemistry is explicitly depicted, a structure is intended to include every possible stereoisomer, both pure or in any possible mixture.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

BIOLOGICAL DATA

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

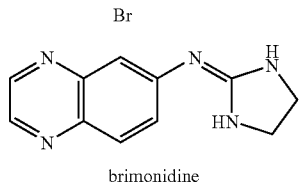

brimonidine

The results of the RSAT assay with several exemplary compounds of the invention are disclosed in Table 1 above together with the chemical formulas of these exemplary compounds. EC$_{50}$ values are nanomolar. NA stands for "not active" at concentrations less than 10 micromolar. IA stands for "intrinsic activity."

| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 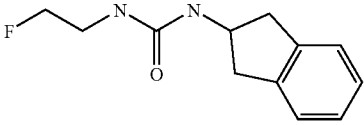 | not active | | 18 | 0.92 | 246 | 0.48 |
| 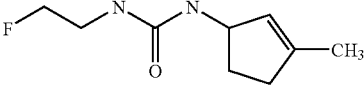 | not active | | 1157 | 0.61 | 911 | 0.47 |
| 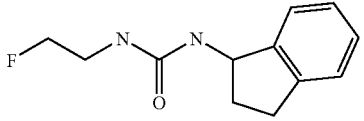 | not active | | 6.3 | 1.21 | 192 | 0.64 |
| 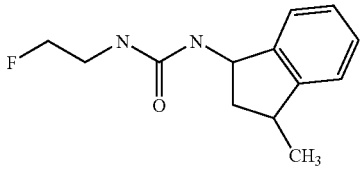 | not active | | 10.9 | 0.96 | 168 | 0.43 |
| 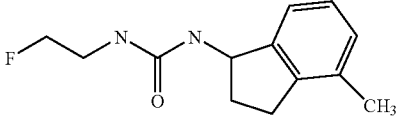 | 120 | 0.59 | 1.2 | 1.1 | 67.2 | 0.79 |
| 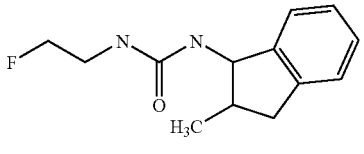 | not active | | 26.4 | 0.85 | not active | |
| 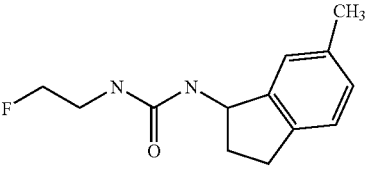 | not active | | 32 | 0.88 | 807 | 0.31 |
| 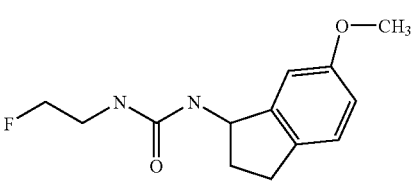 | not active | | 300 | 0.81 | 1464 | 0.31 |
| 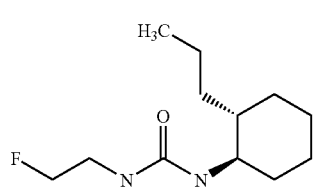 | 1475 | 0.4 | 1739 | 0.84 | not active | |

-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 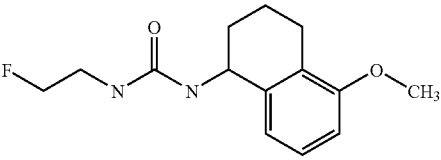 | 2353 | 0.37 | 291 | 0.84 | 872 | 0.51 |
| 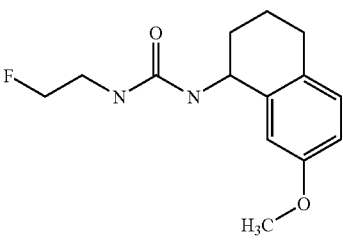 | not active | | 824 | 0.78 | not active | |
| 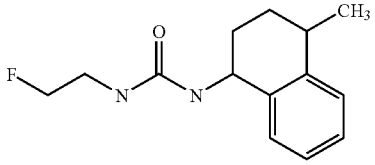 | 331 | 0.34 | 21 | 0.89 | 282 | 0.45 |
| 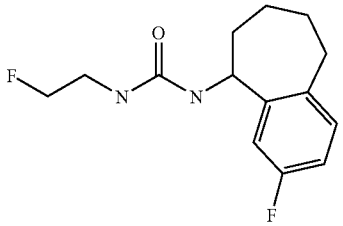 | >2000 | 0.31 | 913 | 0.54 | 341 | 0.3 |
| 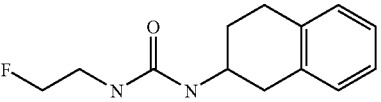 | not active | | 226 | 0.63 | not active | |
| 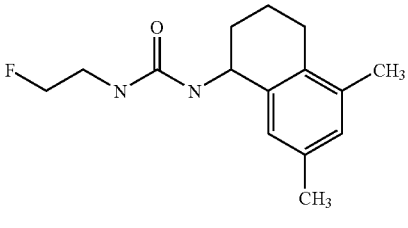 | 109 | 0.49 | 27 | 0.91 | 391 | 0.58 |
| 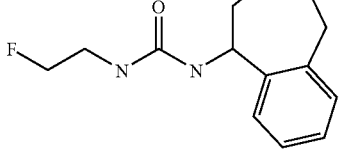 | 534 | 0.3 | 212 | 0.65 | 967 | 0.5 |
| 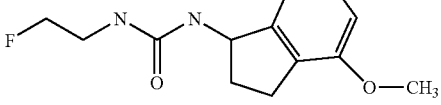 | 2069 | 0.48 | 121 | 0.72 | 1107 | 0.59 |

-continued
| | Alpha 2A | | Alpha 2B | | Alpha 2C | |
| --- | --- | --- | --- | --- | --- | --- |
| | EC$_{50}$ | IA | EC$_{50}$ | IA | EC$_{50}$ | IA |
| 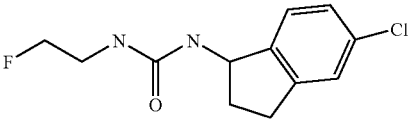 | not active | | 845 | 0.31 | not active | |
| 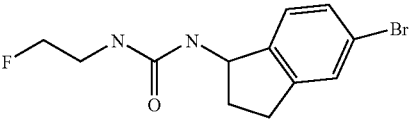 | not active | | 2620 | 0.31 | 1258 | 0.31 |
| 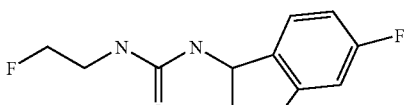 | not active | | 88 | 0.59 | 543 | 0.54 |
|  | not active | | not active | | 1437 | 0.35 |
| 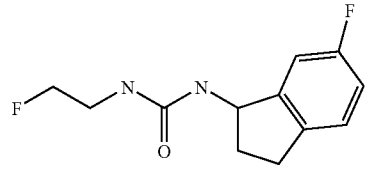 | not active | | 20 | 0.54 | 60 | 0.47 |
| 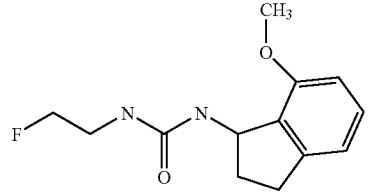 | 277 | 0.48 | 544 | 0.63 | 972 | 0.54 |
| 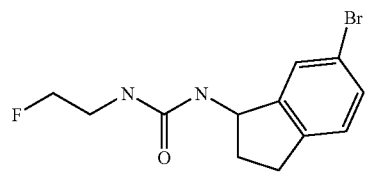 | not active | | 302 | 0.52 | 220 | 0.45 |
| 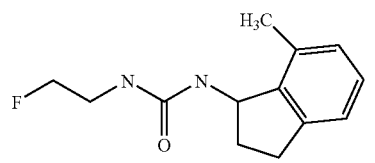 | 189 | 0.43 | 26.8 | 0.6 | 197 | 0.62 |
| Chiral 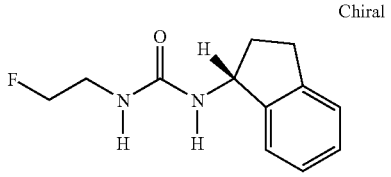 | 693 | 0.36 | 565 | 0.55 | 1822 | 0.61 |

|  | | Alpha 2A | | Alpha 2B | | Alpha 2C | |
| --- | --- | --- | --- | --- | --- | --- | --- |
|  | | EC$_{50}$ | IA | EC$_{50}$ | IA | EC$_{50}$ | IA |
| Chiral structure | | not active | | 1.6 | 1.0 | 17.5 | 0.47 |
| structure | | 586 | 0.36 | 37 | 1.07 | 214 | 0.64 |
| structure | | not active | | 247 | 0.71 | not active | |
| structure | | 343 | 0.63 | 12 | 0.99 | 86 | 0.7 |
| structure | | 34.9 | 1.05 | 2.5 | 1.03 | 116 | 1.1 |
| structure | | 64.6 | 0.97 | 2.7 | 1.06 | 103 | 0.7 |
| structure | | 130 | 0.76 | 1.8 | 1.05 | 107 | 0.68 |
| structure | | not active | | 380 | 0.76 | >2000 | 0.38 |
| structure | | not active | | 1371 | 0.45 | not active | |
| structure | | not active | | 100 | 0.98 | 454 | 0.4 |

-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 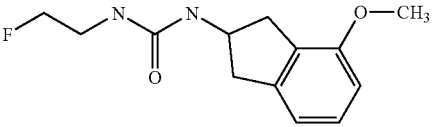 | not active | | 7.5 | 1.57 | 41 | 0.63 |
| 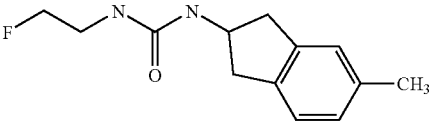 | not active | | 637 | 0.6 | not active | |
| 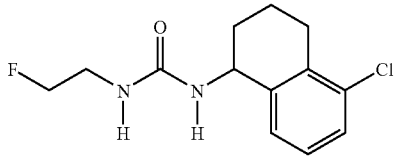 | 168 | 0.42 | 29 | 1.11 | 310 | 0.72 |
| 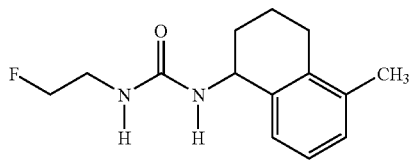 | 48 | 0.41 | 5.6 | 1.3 | 123 | 1.03 |
| 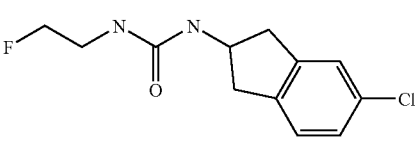 | not active | | 1776 | 0.31 | not active | |
| 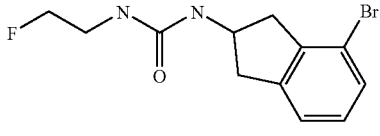 | not active | | 156 | 0.45 | not active | |
| 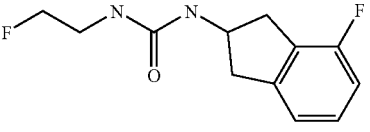 | not active | | 21 | 0.68 | 182 | 0.32 |
| 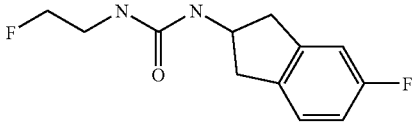 | not active | | 2198 | 0.93 | not active | |
| 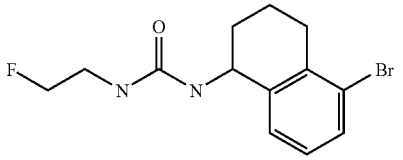 | 146 | 0.41 | 20.3 | 0.91 | 204 | 0.53 |

|  | | Alpha 2A | | Alpha 2B | | Alpha 2C | |
|---|---|---|---|---|---|---|---|
|  | | EC$_{50}$ | IA | EC$_{50}$ | IA | EC$_{50}$ | IA |
| 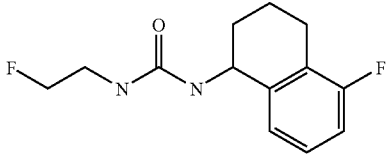 | | 68.3 | 0.52 | 8.2 | 1.03 | 107 | 0.76 |
| 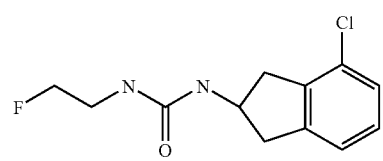 | | not active | | 15.4 | 0.67 | 12.5 | 0.44 |
| 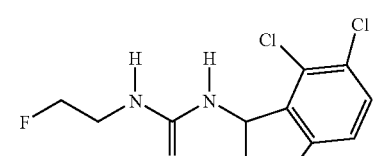 | | not active | | 72.4 | 1.0 | 29.5 | 0.43 |
| 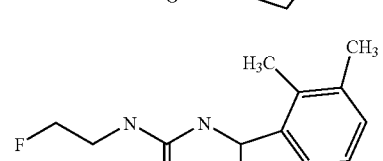 | | not active | | 649 | 0.64 | not active | |
| 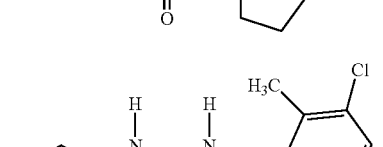 | | not active | | 85 | 0.6 | not active | |
| 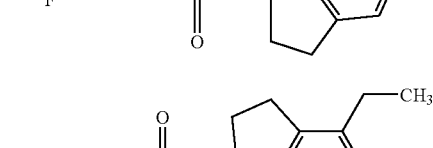 | | not active | | 10.6 | 0.99 | 103 | 0.47 |
| 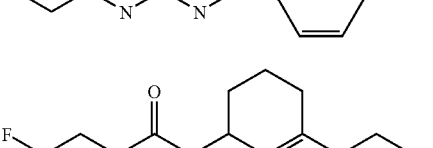 | | 450 | 0.32 | 158 | 0.93 | 904 | 0.34 |
| 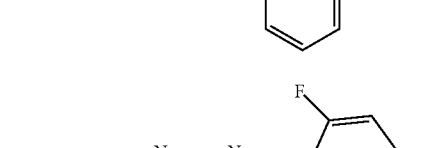 | | 59.6 | 0.41 | 8.8 | 1.08 | 95.4 | 0.55 |
| 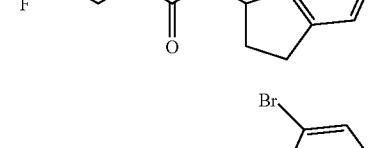 | | 111 | 0.52 | 20 | 1.01 | 716 | 0.97 |

-continued
|  | Alpha 2A | | Alpha 2B | | Alpha 2C | |
|---|---|---|---|---|---|---|
|  | EC$_{50}$ | IA | EC$_{50}$ | IA | EC$_{50}$ | IA |
| 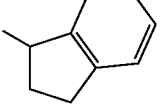 | 29 | 0.68 | 7.2 | 1.05 | 103 | 0.78 |
| 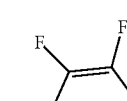 | not active | | 18.7 | 0.97 | 117 | 0.53 |
| 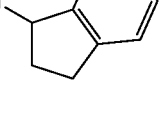 | not active | | 238 | 0.37 | not active | |
| 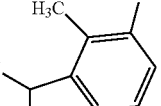 | not active | | 90 | 0.81 | 453 | 0.44 |
| 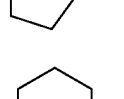 | not active | | 9.6 | 0.86 | 40 | 0.52 |
| 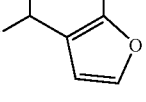 | 95 | 0.62 | 8.3 | 0.95 | 102 | 0.73 |
| 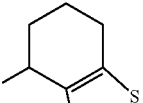 | 186 | 0.53 | 9.6 | 0.96 | 73 | 0.73 |
|  | 429 | 0.48 | 36.6 | 1.0 | 1300 | 0.54 |
| 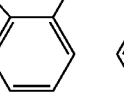 | not active | | 3075 | 0.81 | not active | |

-continued

| | Alpha 2A | | Alpha 2B | | Alpha 2C | |
|---|---|---|---|---|---|---|
| | $EC_{50}$ | IA | $EC_{50}$ | IA | $EC_{50}$ | IA |
| (fluoroethyl urea with 2-methyl-3-ethyl cyclopentenyl) | not active | | 319 | 0.88 | 886 | 0.37 |
| (fluoroethyl urea with 2-methyl cyclohexenyl) | not active | | 74 | 0.9 | 453 | 0.58 |
| (fluoroethyl urea with 2-ethyl cyclohexenyl) | 184 | 0.64 | 45 | 1.22 | 348 | 0.59 |
| (fluoroethyl urea with dihydrocyclopenta-pyridinyl) | 2553 | 0.55 | 100 | 1.08 | 2460 | 0.41 |
| (fluoroethyl urea with 2,3-dimethyl cyclohexenyl) | not active | | 19.7 | 0.76 | 513 | 0.52 |
| (fluoroethyl urea with 3-hydroxymethyl cyclohexenyl) | not active | | 1264 | 0.58 | 2599 | 0.4 |
| (fluoroethyl urea with 2-methyl-3-formyl cyclohexenyl) | not active | | 2580 | 0.81 | 3617 | 0.32 |
| (fluoroethyl urea with 3-methyl cyclohexenyl) | not active | | 225 | 0.42 | 520 | 0.4 |
| (fluoroethyl urea with 3-ethyl cyclohexenyl) | not active | | not active | | 346 | 0.32 |

Synthetic Methods

Proton nuclear magnetic resonance ($^1$H NMR) and carbon nuclear magnetic resonance ($^{13}$C NMR) spectra were recorded on a Varian 300 or 500 MHz spectrometer in deuterated solvent.

Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

General Procedure A for the Synthesis of Fluoroethyl Substituted Indan Ureas:

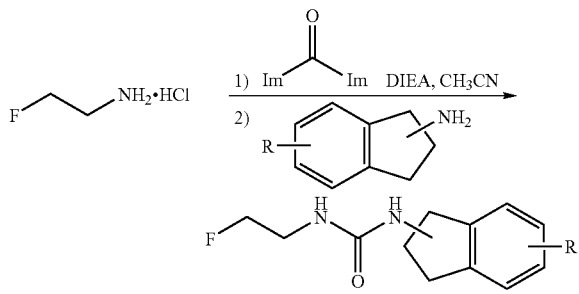

Fluoroethylamine hydrochloride (1.0 eq) was mixed with diimidazole carbonyl (1.0 eq) in acetonitrile at room temperature, and then diisopropylethyl amine (2.0 eq) was added. The resulting reaction mixture was stirred for 14 hours. Indan amine (1.0 eq) in THF was then added and the resulting mixture was stirred for another 14 hours. The reaction mixture was diluted with EtOAc and washed with $H_2O$ (3×75 mL), then concentrated. Chromatography (gradient solvent system, from 50% EtOAc/hexanes to 10% Methanol/EtOAc) or recrystallization in $CH_3CN$ gave the desired title compounds. This method may be adapted to other cycloalkyl-aryl fused rings systems using starting materials such as those shown below.

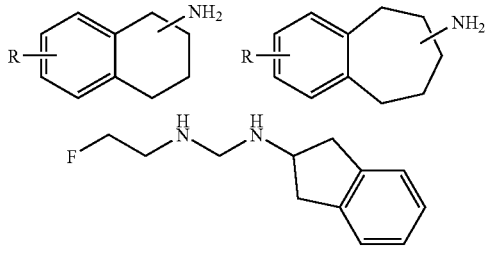

Synthesis of 1-(2-fluoro-ethyl)-3-indan-2-yl-urea

The title urea was produced from commercially available indan-2-ylamine (1.33 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 2.63-2.74 (m, 2H), 3.07-3.17 (m, 2H), 3.21-3.27 (m, 1H), 3.30-3.36 (m, 2H), 4.3 (t, J=5.3 Hz, 1H), 4.5 (t, J=5.0 Hz, 1H), 6.0 (t, J=5.6 Hz, 1H), 6.3 (d, J=7.3 Hz, 1H), 6.97-7.36 (m, 4H).

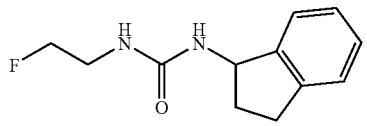

Synthesis of 1-(2-Fluoro-ethyl)-3-indan-1-yl-urea

The title compound was generated from the commercially available indan-1-ylamine according to the general procedure A described above.

1-(2-Fluoro-ethyl)-3-indan-1-yl-urea: Spectroscopic data: $^1$H NMR (300 MHz, DMSO-d$_6$) δ 1.59-1.72 (m, 1H), 2.31-2.42 (m, 1H), 2.71-2.79 (m, 1H), 2.81-2.91 (m, 1H), 3.26-3.41 (m, 2H), 4.3 (t, 1H, J=5.0 Hz), 4.5 (t, 1H, J=5.3 Hz), 5.1 (q, 1H, J=7.9 Hz), 6.0 (t, 1H, J=5.0 Hz), 6.3 (d, 1H, J=8.5 Hz), 7.14-7.23 (m, 4H).

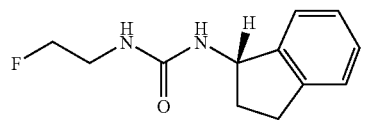

Synthesis of (R)-(−)-1-(2-Fluoro-ethyl)-3-indan-1-yl-urea

The title compound was generated from the commercially available (R)-indan-1-ylamine according to the general procedure A described above.

(R)-(+)-1-(2-Fluoro-ethyl)-3-indan-1-yl-urea: The title urea was obtained from indan-1-(R)-ylamine (1.30 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.60-1.74 (m, 1H), 2.33-2.44 (m, 1H), 2.72-2.81 (m, 1H), 2.83-2.93 (m, 1H), 3.27-3.42 (m, 2H), 4.4 (t, J=5.3 Hz, 1H), 4.5 (t, J=5.0 Hz, 1H), 5.1 (q, J=8.2 Hz, 1H), 6.1 (t, J=5.9 Hz, 1H), 6.3 (d, J=8.2 Hz, 1H), 7.14-7.26 (m, 4H). $^{13}$C NMR (75 MHz, DMSO-d$_6$) δ 30.2, 34.8, 40.5 (d, J=20.7 Hz), 55.2, 84.4 (d, J=164.1 Hz), 124.4, 125.1, 126.9, 127.9, 143.3, 145.5, 158.5.

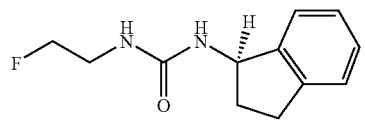

Synthesis of (S)-(−)-1-(2-Fluoro-ethyl)-3-indan-1-yl-urea

The title compound was generated from the commercially available (S)-indan-1-ylamine according to the general procedure A described above.

(S)-(−)-1-(2-Fluoro-ethyl)-3-indan-1-yl-urea: Spectroscopic data: $^1$H NMR (300 MHz, DMSO-d$_6$) δ 1.60-1.74 (m, 1H), 2.32-2.45 (m, 1H), 2.72-2.81 (m, 1H), 2.83-2.93 (m, 1H), 3.27-3.42 (m, 2H), 4.3 (t, J=5.3 Hz, 1H), 4.5 (t, J=5.0 Hz, 1H), 5.1 (q, J=8.2 Hz, 1H), 6.0 (t, J=5.9 Hz, 1H), 6.3 (d, J=8.5 Hz, 1H), 7.16-7.26 (m, 4H).

General Procedure B for the Synthesis of 1-(2-Fluoro-Ethyl)-3-(Substituted-Indan-1-yl)-Ureas:

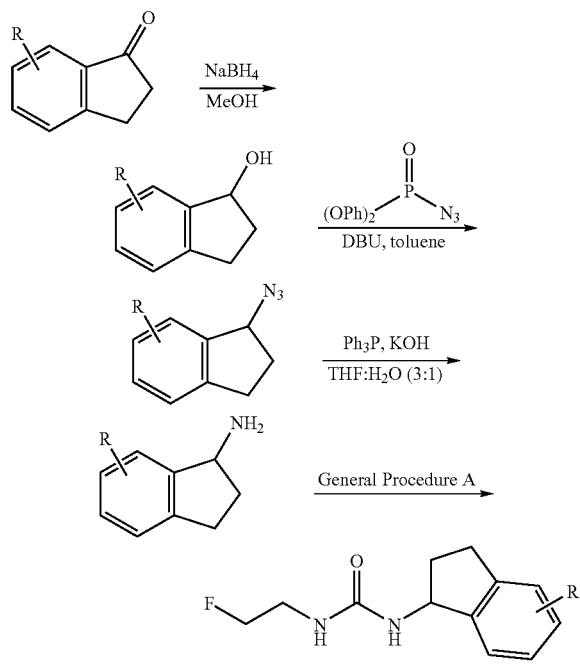

Indanone was dissolved in ether and cooled to 0° C., a solution NaBH₄ (1.0 eq) in MeOH was slowly added. The reaction mixture was stirred for 1 hour and then quenched with saturated NH₄Cl. The resulting mixture was extracted with Et₂O (3×50 mL), and the combined organic extracts was washed with H₂O (3×50 mL), brine (1×50 mL), dried over MgSO₄ and concentrated. Purification by column chromatography using hexane:EtOAc (4:1) as eluant gave the pure indanol. The indanol was then dissolved in toluene and cooled to 0° C., diphenylphosphoryl azide (1.5 eq) was added. The resulting mixture was stirred for a few minutes and DBU (1.5 eq) was added slowly. After stirring the reaction mixture overnight, it was diluted with toluene and washed with H₂O (3×50 mL), brine (1×50 mL), dried over MgSO₄ and concentrated. Purification by column chromatography using hexane:EtOAc (4:1) as eluant gave the desired azido compound. This azido compound was then dissolved in THF:H₂O (3:1), Ph₃P (1.1 eq) was added, followed by KOH (1.0 eq). The resulting mixture was stirred overnight. The reaction mixture was then diluted with H₂O and slowly acidified with HCl and the aqueous layer was washed with Et₂O (3×50 mL). The aqueous layer was then basified with NaOH (pH 14) and extracted with Et₂O (3×50 mL). The combined organic extracts were washed with H₂O (1×25 mL), brine (1×25 mL), dried over K₂CO₃ and concentrated to give the desired indan amine. The final fluoroethyl ureas were thus obtained according to the protocol described in General Procedure A. This method may be adapted to other cycloalkyl-aryl fused rings systems using starting materials such as those shown below.

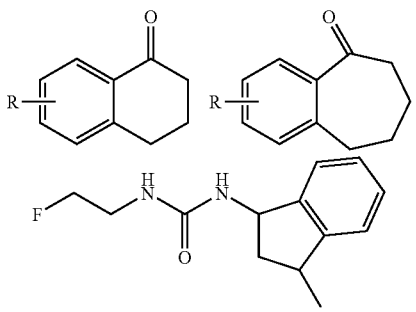

Synthesis of 1-(2-fluoroethyl)-3-(3-methylindan-1-yl)urea

The title compound was generated from commercially available 3-methyl-1-indanone according to the general procedure B. The intermediates 3-methyl-1-indanol, 1-azido-3-methylindan and 3-methylindan-1-ylamine were isolated and characterized.

3-Methyl-1-indanol': 4.77 g (94%) of the title indanol was obtained from 3-methyl-1-indanone (5.00 g, 34.20 mmol) according to the protocol described in general procedure B. Spectroscopic data: ¹H NMR (300 MHz, CDCl₃) δ 1.3 (d, 3H, J=6.7 Hz), 1.41-1.52 (m, 1H), 1.9 (br s, 1H), 2.68-2.80 (m, 1H), 2.98-3.11 (m, 1H), 5.2 (t, 1H, J=7.3 Hz), 7.19-7.31 (m, 3H), 7.35-7.41 (m, 1H).

1-Azido-3-methyl-indan: 5.53 g (99%) of the title azide was obtained from 3-methyl-1-indanol (4.77 g, 32.20 mmol) according to the protocol described in general procedure B. Spectroscopic data: ¹H NMR (300 MHz, CDCl₃) δ 1.3 (d, 3H, J=7.0 Hz), 1.88-1.99 (m, 1H), 2.32-2.41 (m, 1H), 3.35-3.48 (m, 1H), 4.77-4.89 (m, 1H), 7.19-7.46 (m, 4H).

3-Methyl-indan-1-ylamine: 4.49 g (96%) of the title amine was obtained from 1-azido-3-methyl-indan (5.53 g, 32.00 mmol) according to the protocol described in general procedure B. Spectroscopic data: ¹H NMR (300 MHz, CDCl₃) δ 1.2 (d, 3H, J=7.0 Hz), 1.7 (br s, 2H), 1.94-2.10 (m, 2H), 3.30-3.41 (m, 1H), 4.4 (t, 1H, J=6.2 Hz), 7.12-7.27 (m, 3H), 7.27-7.37 (m, 1H).

1-(2-Fluoro-ethyl)-3-(3-methyl-indan-1-yl)-urea: Spectroscopic data: ¹H NMR (300 MHz, DMSO-d₆) δ 1.2 (d, 3H, J=7.0 Hz), 1.87-2.01 (m, 2H), 3.21-3.38 (m, 3H), 4.3 (t, 1H, J=5.0 Hz), 4.5 (t, 1H, J=5.0 Hz), 5.1 (q, 1H, J=7.8 Hz), 5.9 (t, 1H, J=5.9 Hz), 6.3 (d, 1H, J=8.2 Hz), 7.13-7.24 (m, 4H).

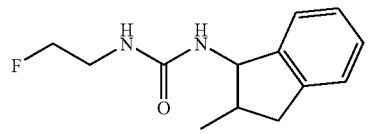

Synthesis of 1-(2-fluoro-ethyl)-3-(2-methyl-indan-1-yl)-urea

The title compound was generated from commercially available 2-methyl-1-indanone according to the general procedure B. The intermediates 2-methyl-1-indanol, 1-azido-2-methylindan and 2-methylindan-1-ylamine were isolated and characterized.

2-Methyl-1-indanol[ii]: Spectroscopic data: $^1$H NMR (300 MHz, CDCl$_3$) (mixture of diastereomers) δ 1.1 (d, J=7.0 Hz), 1.3 (d, J=6.7 Hz), 1.6 (br s), 1.8 (br s), 2.19-2.32 (m), 2.39-2.75 (m), 2.91-3.00 (m), 3.06-3.16 (m), 4.7 (d, J=6.7 Hz), 5.0 (d, J=5.9 Hz), 7.18-7.27 (m), 7.34-7.43 (m).

1-Azido-2-methyl-indan: Spectroscopic data: $^1$H NMR (300 MHz, CDCl$_3$) (mixture of diastereomers) δ 1.2 (d, J=6.7 Hz), 1.2 (d, J=6.7 Hz), 2.43-2.57 (m), 2.60-2.74 (m), 2.88-3.01 (m), 3.10-3.23 (m), 4.4 (d, J=6.4 Hz), 4.7 (d, J=5.9 Hz), 7.05-7.11 (m), 7.17-7.29 (m), 7.32-7.40 (m).

2-Methyl-indan-1-ylamine[iii]: Spectroscopic data: $^1$H NMR (300 MHz, CDCl$_3$) (mixture of diastereomers) δ 1.0 (d, J=6.7 Hz), 1.2 (d, J=6.4 Hz), 1.6 (br s), 1.80-1.90 (m), 1.93-2.07 (m), 2.36-2.71 (m), 2.92-3.07 (m), 3.70-3.81 (m), 4.2 (d, J=6.2 Hz), 7.16-7.26 (m), 7.28-7.35 (m).

1-(2-Fluoro-ethyl)-3-(2-methyl-indan-1-yl)-urea: Spectroscopic data: $^1$H NMR (300 MHz, DMSO-d$_6$) (1:1 mixture of diastereomers) δ 0.8 (d, 3H, J=7.0 Hz), 1.1 (d, 3H, J=6.4 Hz), 2.01-2.16 (m, 1H), 2.42-2.50 (m, 3H), 2.88-3.03 (m, 2H), 3.28-3.44 (m, 4H), 4.3 (q, 2H, J=5.6 Hz), 4.5 (q, 2H, J=5.6 Hz), 4.7 (t, 1H, J=8.8 Hz), 5.1 (t, 1H, J=7.0 Hz), 6.1 (t, 2H, J=4.7 Hz), 6.2 (q, 2H, J=8.8 Hz), 7.09-7.23 (m, 8H).

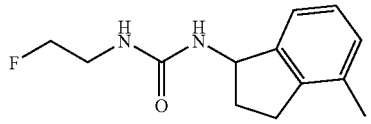

Synthesis of 1-(2-fluoro-ethyl)-3-(4-methyl-indan-1-yl)-urea

The title compound was generated from commercially available 4-methyl-1-indanone according to the general procedure B. The intermediates 4-methyl-1-indanol, 1-azido-4-methylindan and 4-methylindan-1-ylamine were isolated and characterized.

4-Methyl-1-indanol[iv]: 4.29 g (85%) of the title compound was obtained from 4-methyl-1-indanone (5.00 g, 34.20 mmol) and NaBH$_4$ (1.30 g, 35.35 mmol) according to general procedure B above. Spectroscopic data: $^1$H NMR (300 MHz, CDCl$_3$) δ 1.7 (br s, 1H), 1.89-2.03 (m, 1H), 2.3 (s, 3H), 2.43-2.55 (m, 1H), 2.67-2.80 (m, 1H), 2.92-3.05 (m, 1H), 5.2 (t, 1H, J=6.7, 5.0 Hz), 7.08 (d, 1H, J=7.3 Hz), 7.1 (t, 1H, J=7.3 Hz), 7.3 (d, 1H, J=7.6 Hz).

1-Azido-4-ethyl-indan: The title azido compound was obtained from 4-methyl-1-indanol (4.29 g, 29.00 mmol), diphenylphosphoryl azide (9.40 mL, 43.62 mmol) and DBU (6.50 mL, 43.46 mmol) according to the protocols as outlined in general procedure B. Spectroscopic data: $^1$H NMR (300 MHz, CDCl$_3$) δ 2.06-2.17 (m, 1H), 2.3 (s, 3H), 2.34-2.49 (m, 1H), 2.71-2.85 (m, 1H), 2.89-3.04 (m, 1H), 4.77-4.90 (m, 1H), 7.09-7.24 (m, 3H).

4-Methyl-indan-1-ylamine: 3.96 g (89%) of the title amine was obtained from 1-azido-4-methyl-indan (5.23 g, 30.20 mmol), triphenylphosphine (8.00 g, 30.50 mmol) and KOH (1.70 g, 30.30 mmol) according to general procedure B described above. Spectroscopic data: $^1$H NMR (300 MHz, CDCl$_3$) δ 1.58-1.70 (m, 1H), 1.7 (s, 2H), 2.2 (s, 3H), 2.41-2.57 (m, 1H), 2.60-2.76 (m, 1H), 2.82-2.96 (m, 1H), 4.3 (t, 1H, J=7.6 Hz), 6.99-7.06 (m, 1H), 7.09-7.18 (m, 2H).

1-(2-Fluoro-ethyl)-3-(4-methyl-indan-1-yl)-urea: The title urea was obtained from 4-methyl-indan-1-ylamine (1.50 g, 10.20 mmol), diimidazole carbonyl (1.65 g, 10.17 mmol), fluoroethyl amine hydrochloride (1.0 g, 90% purity, 9.05 mmol) and diisopropyl ethyl amine (3.60 mL, 20.67 mmol) according to the protocols as outlined in general procedure A above. Spectroscopic data: $^1$H NMR (300 MHz, DMSO-d$_6$) δ 1.57-1.71 (m, 1H), 2.2 (s, 3H), 2.29-2.43 (m, 1H), 2.56-2.70 (m, 1H), 2.74-2.87 (m, 1H), 3.26-3.41 (m, 2H), 4.3 (t, 1H, J=5.9 Hz), 4.5 (t, 1H, J=5.0 Hz), 5.1 (q, 1H, J=7.9 Hz), 6.0 (t, 1H, J=5.6 Hz), 6.3 (d, 1H, J=8.5 Hz), 6.96-7.10 (m, 3H). $^{13}$C NMR (75 MHz, DMSO-d$_6$) δ 19.1, 28.7, 34.2, 40.5 (d, J=20.37 Hz), 55.3, 84.06 (d, J=164 Hz), 121.8, 127.2, 128.6, 134.0, 142.1, 145.2, 158.4.

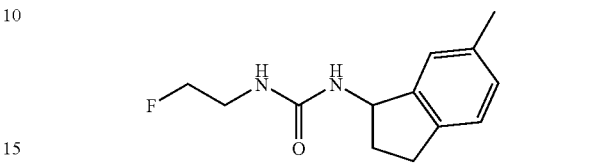

Synthesis of 1-(2-fluoro-ethyl)-3-(6-methyl-indan-1-yl)-urea

The title compound was generated from commercially available 6-methyl-1-indanone according to the general procedure B. The intermediates 6-methyl-1-indanol, 1-azido-6-methylindan and 6-methylindan-1-ylamine were isolated and characterized.

6-Methyl-1-indanol[v]: Spectroscopic data: $^1$H NMR (300 MHz, CDCl$_3$) δ 1.8 (br s, 1H), 1.87-1.99 (m, 1H), 2.4 (s, 3H), 2.43-2.50 (m, 1H), 2.67-2.82 (m, 1H), 2.94-3.10 (m, 1H), 5.2 (t, 1H, J=5.9 Hz), 7.10 (d, 1H, J=7.6 Hz), 7.14 (d, 1H, J=7.6 Hz), 7.2 (s, 1H).

1-Azido-6-methyl-indan: Spectroscopic data: $^1$H NMR (300 MHz, CDCl$_3$) δ 2.05-2.17 (m, 1H), 2.4 (br s, 3H), 2.38-2.51 (m, 1H), 2.74-2.88 (m, 1H), 2.94-3.09 (m, 1H), 4.72-4.86 (m, 1H), 7.09 (d, 1H, J=7.9 Hz), 7.14 (d, 1H, J=7.6 Hz), 7.2 (s, 1H).

6-Methyl-indan-1-ylamine: Spectroscopic data: $^1$H NMR (300 MHz, CDCl$_3$) δ 1.60-1.75 (m, 3H), 2.3 (s, 3H), 2.42-2.54 (m, 1H), 2.69-2.81 (m, 1H), 2.85-2.96 (m, 1H), 4.3 (t, 1H, J=7.3 Hz), 7.0 (d, 1H, J=7.6 Hz), 7.12 (d, 1H, J=7.6 Hz), 7.15 (s, 1H).

1-(2-Fluoro-ethyl)-3-(6-methyl-indan-1-yl)-urea (AGN-201610): Spectroscopic data: $^1$H NMR (300 MHz, DMSO-d$_6$) δ 1.58-1.72 (m, 1H), 2.3 (s, 3H), 2.32-2.42 (m, 1H), 2.64-2.75 (m, 1H), 2.77-2.86 (m, 1H), 3.28-3.43 (m, 2H), 4.3 (t, 1H, J=4.4 Hz), 4.5 (t, 1H, J=4.4 Hz), 5.1 (q, 1H, J=7.9 Hz), 6.0 (t, 1H, J=5.9 Hz), 6.3 (d, 1H, J=8.2 Hz), 6.97-7.05 (m, 2H), 7.1 (d, 1H, J=7.6 Hz).

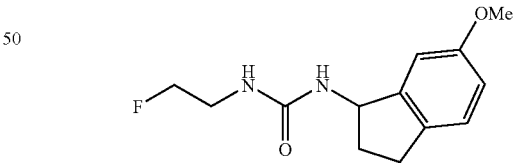

Synthesis of 1-(2-fluoro-ethyl)-3-(6-methoxy-indan-1-yl)-urea

The title compound was generated from commercially available 6-methoxy-1-indanone according to the general procedure B. The intermediates 6-methoxy-1-indanol, 1-azido-6-methoxyindan and 6-methoxyindan-1-ylamine were isolated and characterized.

6-Methoxy-1-indanol[vi]: Spectroscopic data: $^1$H NMR (300 MHz, CDCl$_3$) δ 1.8 (br s, 1H), 1.89-2.02 (m, 1H), 2.44-2.58

(m, 1H), 2.68-2.81 (m, 1H), 2.91-3.07 (m, 1H), 3.8 (s, 3H), 5.2 (t, 1H, J=6.2 Hz), 6.74-6.88 (m, 1H), 6.88-7.00 (m, 1H), 7.1 (d, 1H, J=8.5 Hz).

1-Azido-6-methoxy-indan: Spectroscopic data: $^1$H NMR (300 MHz, CDCl$_3$) δ 2.06-2.19 (m, 1H), 2.38-2.53 (m, 1H), 2.73-2.86 (m, 1H), 3.73-3.87 (m, 1H), 3.8 (s, 3H), 4.8 (t, 1H, J=5.0 Hz), 6.84 (dd, 1H, J=8.21 Hz), 6.9 (br s, 1H), 7.16 (d, 1H, J=8.5 Hz).

6-Methoxy-indan-1-ylamine[vii]: Spectroscopic data: $^1$H NMR (300 MHz, CDCl$_3$) δ 1.61-1.77 (m, 1H), 1.8 (br s, 2H), 2.42-2.56 (m, 1H), 2.65-2.80 (m, 1H), 2.80-2.95 (m, 1H), 3.8 (s, 3H), 4.3 (t, 1H, J=7.6 Hz), 6.8 (dd, 1H, J=8.2 Hz), 6.9 (br s, 1H), 7.1 (d, 1H, J=7.9 Hz).

1-(2-Fluoro-ethyl)-3-(6-methoxy-indan-1-yl)-urea: Spectroscopic data: $^1$H NMR (500 MHz, DMSO-d$_6$) δ 1.63-1.71 (m, 1H), 2.35-2.42 (m, 1H), 2.63-2.71 (m, 1H), 2.76-2.83 (m, 1H), 3.31-3.40 (m, 2H), 3.7 (s, 3H), 4.4 (t, 1H, J=5.4 Hz), 4.5 (t, 1H, J=5.4 Hz), 5.1 (q, 1H, J=7.8 Hz), 6.1 (t, 1H, J=6.3 Hz), 6.3 (d, 1H, J=8.8 Hz), 6.75-6.78 (m, 2H), 7.10-7.13 (m, 1H).

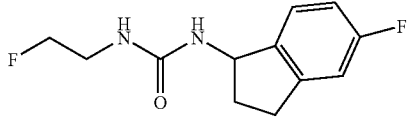

Synthesis of 1-(2-fluoro-ethyl)-3-(5-fluoro-indan-1-yl)-urea

The title compound was generated from commercially available 5-fluoro-1-indanone according to the general procedure B. The intermediates 5-fluoro-1-indanol, 1-azido-5-fluoroindan and 5-fluoroindan-1-ylamine were isolated and characterized.

5-Fluoro-1-indanol[viii]: Spectroscopic data: $^1$H NMR (300 MHz, CDCl$_3$) δ 1.90-2.06 (m, 2H), 2.43-2.54 (m, 1H), 2.73-2.85 (m, 1H), 2.98-3.09 (m, 1H), 5.2 (t, 1H, J=5.9 Hz), 6.87-6.94 (m, 2H), 7.26-7.35 (m, 1H).

1-Azido-5-fluoro-indan: Spectroscopic data: $^1$H NMR (300 MHz, CDCl$_3$) δ 2.10-2.21 (m, 1H), 2.41-2.53 (m, 1H), 2.80-2.91 (m, 1H), 3.02-3.13 (m, 1H), 4.77-4.87 (m, 1H), 6.90-6.98 (m, 2H), 7.25-7.36 (m, 1H).

5-Fluoro-indan-1-ylamine: Spectroscopic data: $^1$H NMR (300 MHz, CDCl$_3$) δ 1.80-1.96 (m, 3H), 2.45-2.56 (m, 1H), 2.71-2.83 (m, 1H), 2.87-2.99 (m, 1H), 4.3 (t, 1H, J=7.6, 7.0 Hz), 6.84-6.92 (m, 2H), 7.18-7.28 (m, 1H).

1-(2-Fluoro-ethyl)-3-(5-fluoro-indan-1-yl)-urea: Spectroscopic data: $^1$H NMR (500 MHz, DMSO-d$_6$) δ 1.68-1.76 (m, 1H), 2.37-2.44 (m, 1H), 2.72-2.80 (m, 1H), 2.85-2.92 (m, 1H), 3.30-3.39 (m, 2H), 4.4 (t, 1H, J=4.9 Hz), 4.5 (t, 1H, J=5.4 Hz), 5.1 (q, 1H, J=7.8 Hz), 6.1 (t, 1H, J=5.9 Hz), 6.3 (d, 1H, J=8.3 Hz), 6.96-7.01 (m, 1H), 7.03-7.06 (m, 1H), 7.19-7.23 (m, 1H).

General Procedure C for the Synthesis of fluoroethyl Substituted Indan Ureas:

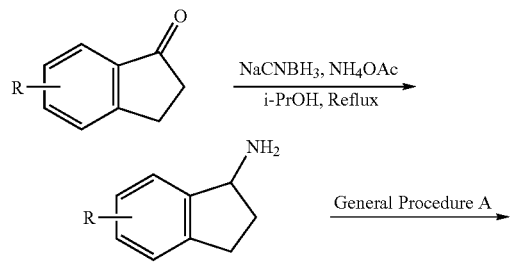

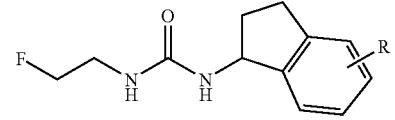

NaBH$_3$CN (7.0 eq) was added to a solution of an indanone in isopropanol. NH$_4$OAc (30 eq) was then added and the resulting mixture was stirred at room temperature for 4 hours, then refluxed for 22 hours. After cooling to room temperature, the reaction mixture was quenched with 200 mL of 2.5 N aq. NaOH. The layers were then separated and the aqueous layer was extracted with CH$_2$Cl$_2$. The combined organic extracts were washed with H$_2$O (75 mL), dried over K$_2$CO$_3$ and concentrated to give the desired indan amine. The final fluoroethyl ureas were thus obtained according to the protocol described in General Procedure A. This method may be adapted to other cycloalkyl-aryl fused rings systems using starting materials such as those shown below.

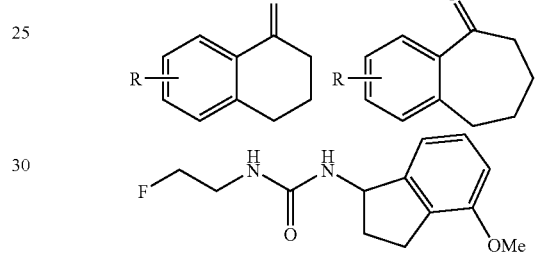

Synthesis of 1-(2-fluoro-ethyl)-3-(4-methoxy-indan-1-yl)-urea

The title compound was generated from commercially available 4-methoxy-1-indanone according to the general procedure C. The intermediate 4-methoxyindan-1-ylamine was isolated and characterized.

4-Methoxy-indan-1-ylamine[ix]: The title amine was obtained from 4-methoxy-1-indanone (2.00 g, 12.35 mmol), NaBH$_3$CN (5.43 g, 86.40 mmol) and NH$_4$OAc (28.50 g, 0.37 mol) according to general procedure C described above. Spectroscopic data: $^1$H NMR (300 MHz, CDCl$_3$) δ 1.61-1.73 (m, 1H), 1.8 (br s, 2H), 2.44-2.59 (m, 1H), 2.64-2.78 (m, 1H), 2.90-3.04 (m, 1H), 3.8 (s, 3H), 4.20-4.59 (m, 1H), 6.8 (d, 1H, J=8.2 Hz), 7.0 (d, 1H, J=7.6 Hz), 7.2 (t, 1H, J=8.2, 7.3 Hz).

1-(2-Fluoro-ethyl)-3-(4-methoxy-indan-1-yl)-urea: The title urea was obtained from 4-methoxy-indan-1-ylamine (2.81 g, 17.24 mmol), diimidazole carbonyl (2.80 g, 17.26 mmol), fluoroethyl amine hydrochloride (1.72 g, 90% purity, 15.56 mmol) and diisopropyl ethyl amine (6.00 mL, 34.45 mmol) according to general procedure A above. Spectroscopic data: $^1$H NMR (500 MHz, DMSO-d$_6$) δ 1.61-1.69 (m, 1H), 2.34-2.41 (m, 1H), 2.57-2.65 (m, 1H), 2.79-2.85 (m, 1H), 3.30-3.39 (m, 2H), 3.8 (s, 3H), 4.4 (t, 1H, J=5.4 Hz), 4.5 (t, 1H, J=5.4 Hz), 5.1 (q, 1H, J=8.3 Hz), 6.0 (t, 1H, J=5.9 Hz), 6.3 (d, 1H, J=7.3 Hz), 6.78-6.83 (m, 2H), 7.2 (t, 1H, J=7.6 Hz). $^{13}$C NMR (126 MHz, DMSO-d$_6$) δ 27.0, 34.4, 40.52 (d, J=20.11 Hz), 55.5, 55.7, 84.1 (d, J=163.42 Hz), 109.8, 116.7, 128.7, 130.5, 147.2, 156.2, 158.4.

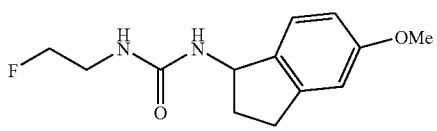

Synthesis of 1-(2-fluoro-ethyl)-3-(5-methoxy-indan-1-yl)-urea

The title compound was generated from commercially available 5-methoxy-1-indanone according to the general procedure C. The intermediate 5-methoxyindan-1-ylamine was isolated and characterized.

5-Methoxy-indan-1-ylamine[x]: 2.19 g of the crude title amine (which was used in the next step without further purification) was obtained from 5-methoxy-1-indanone (2.00 g, 12.30 mmol), NaBH$_3$CN (5.42 g, 86.25 mmol) and NH$_4$OAc (28.50 g, 369.75 mmol) according to the protocols as outlined in general procedure C described above.

1-(2-Fluoro-ethyl)-3-(5-methoxy-indan-1-yl)-urea: The title urea was obtained from 5-methoxy-indan-1-ylamine (2.19 g, 13.42 mmol), diimidazole carbonyl (2.17 g, 13.37 mmol), fluoroethyl amine hydrochloride (1.33 g, 90% purity, 12.03 mmol) and diisopropyl ethyl amine (4.70 mL, 26.98 mmol) according to general procedure A above. Spectroscopic data: $^1$H NMR (500 MHz, DMSO-d$_6$) δ 1.63-1.71 (m, 1H), 2.34-2.40 (m, 1H), 2.68-2.75 (m, 1H), 2.81-2.88 (m, 1H), 3.29-3.38 (m, 2H), 3.7 (s, 3H), 4.4 (t, 1H, J=4.9 Hz), 4.5 (t, 1H, J=5.4 Hz), 5.0 (q, 1H, J=7.3 Hz), 6.0 (t, 1H, J=5.4 Hz), 6.2 (d, 1H, J=8.3 Hz), 6.72-6.76 (m, 1H), 6.8 (s, 1H), 7.1 (d, 1H, J=8.3 Hz). $^{13}$C NMR (126 MHz, DMSO-d$_6$) δ 30.4, 35.1, 40.5 (d, J=20.16 Hz), 54.6, 55.8, 84.1 (d, J=164.0 Hz), 110.2, 113.2, 125.2, 137.4, 145.0, 158.4, 159.8.

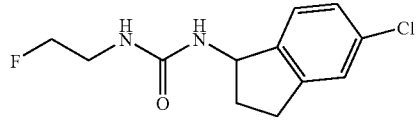

Synthesis of 1-(5-chloro-indan-1-yl)-3-(2-fluoro-ethyl)-urea

The title compound was generated from commercially available 5-chloro-1-indanone according to the general procedure C. The intermediate 5-chloroindan-1-ylamine was isolated and characterized.

5-Chloro-indan-1-ylamine[xi]: Spectroscopic data: $^1$H NMR (300 MHz, CDCl$_3$) δ 1.65-1.72 (m, 1H), 1.8 (br s, 2H), 2.44-2.58 (m, 1H), 2.74-2.85 (m, 1H), 2.87-2.97 (m, 1H), 4.27-4.38 (m, 1H), 7.14-7.28 (m, 3H).

1-(5-Chloro-indan-1-yl)-3-(2-fluoro-ethyl)-urea: Spectroscopic data: $^1$H NMR (500 MHz, DMSO-d$_6$) δ 1.67-1.75 (m, 1H), 2.36-2.43 (m, 1H), 2.72-2.80 (m, 1H), 2.84-2.91 (m, 1H), 3.31-3.39 (m, 2H), 4.4 (t, 1H, J=4.9 Hz), 4.5 (t, 1H, J=4.9 Hz), 5.1 (q, 1H, J=7.8 Hz), 6.1 (t, 1H, J=5.9 Hz), 6.4 (d, 1H, J=8.3 Hz), 7.19-7.23 (m, 2H), 7.3 (s, 1H).

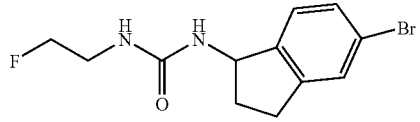

Synthesis of 1-(5-bromo-indan-1-yl)-3-(2-fluoro-ethyl)-urea

The title compound was generated from commercially available 5-bromo-1-indanone according to the general procedure C. The intermediate 5-bromoindan-1-ylamine was isolated and characterized.

5-bromo-indan-1-ylamine: Spectroscopic data: $^1$H NMR (300 MHz, CDCl$_3$) δ 1.6 (br s, 2H), 1.63-1.80 (m, 1H), 2.44-2.58 (m, 1H), 2.76-2.85 (m, 1H), 2.87-2.98 (m, 1H), 4.26-4.37 (m, 1H), 7.13-7.21 (m, 1H), 7.24-7.39 (m, 2H).

1-(5-Bromo-indan-1-yl)-3-(2-fluoro-ethyl)-urea: Spectroscopic data: $^1$H NMR (500 MHz, DMSO-d$_6$) δ 1.66-1.73 (m, 1H), 2.34-2.41 (m, 1H), 2.73-2.81 (m, 1H), 2.84-2.92 (m, 1H), 3.30-3.39 (m, 2H), 4.4 (t, 1H, J=4.9 Hz), 4.5 (t, 1H, J=4.9 Hz), 5.1 (q, 1H, J=8.3 Hz), 6.1 (t, 1H, J=5.9 Hz), 6.4 (d, 1H, J=8.3 Hz), 7.1 (d, 1H, J=7.8 Hz), 7.4 (d, 1H, J=7.8 Hz), 7.4 (s, 1H).

General Procedure D for the Synthesis of Fluoroethyl Substituted Indan Ureas:

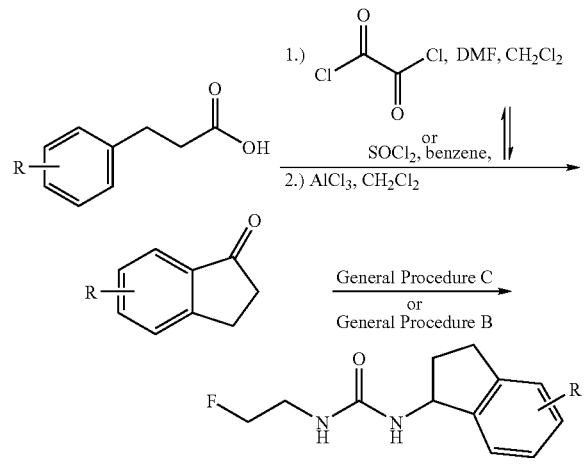

To a solution of 3-(substituted-phenyl)-propionic acid in CH$_2$Cl$_2$ at 0° C. was added oxalyl chloride (1.5 eq) followed by 2-3 drops of DMF (in case of SOCl$_2$, benzene would be used as solvent, and the reaction mixture would be refluxed for 3 hours). The resulting mixture was stirred until no more gas evolution was observed. After concentration of the reaction mixture, the residue was dissolved in CH$_2$Cl$_2$, cooled to 0° C., and AlCl$_3$ (1.0 eq) was added in 3 batches at 3-minute interval. After stirring for 1 hour, the reaction mixture was quenched in ice-water and the layers were separated. The aqueous layer was extracted with Et$_2$O (3×150 mL) and the combined organic extracts were washed with H$_2$O (3×100 mL), saturated NaHCO$_3$ (3×100 mL), brine (1×100 mL), dried over MgSO$_4$ and concentrated. Purification by column chromatography using hexane:EtOAc (4.5:0.5) as eluant gave the desired substituted indanone. The indanone was converted to the desired fluoroethyl ureas via the protocol described in general procedure C. This method may be adapted to other cycloalkyl-aryl fused rings systems using starting materials such as those shown below.

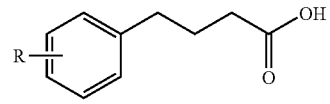

-continued

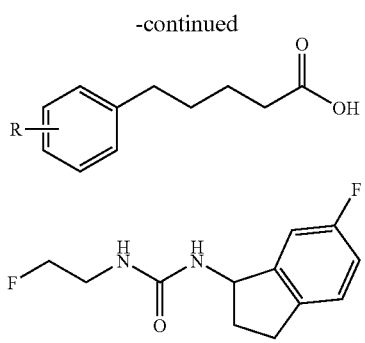

Synthesis of 1-(2-fluoro-ethyl)-3-(6-fluoro-indan-1-yl)-urea

The title compound was generated from commercially available 3-(4-fluoro-phenyl)-propionic acid according to the general procedure D. The intermediates 6-fluoro-1-indanone and 6-fluoroindan-1-ylamine were isolated and characterized.

6-Fluoro-1-indanone[xii]: Spectroscopic data: $^1$H NMR (500 MHz, CDCl$_3$) δ 2.72-2.76 (m, 2H), 3.1 (t, 2H, J=5.9 Hz), 7.28-7.32 (m, 1H), 7.4 (dd, 1H, J=7.8 Hz), 7.5 (dd, 1H, J=8.3 Hz).

6-Fluoro-indan-1-ylamine: The title compound was generated from 6-fluoro-1-indanone (2.00 g, 13.30 mmol), NaBH$_3$CN (5.90 g, 93.89 mmol) and NH$_4$OAc (31.00 g, 0.40 mol) according to the protocols as outlined in general procedure C.

1-(2-Fluoro-ethyl)-3-(6-fluoro-indan-1-yl)-urea: Spectroscopic data: $^1$H NMR (500 MHz, DMSO-d$_6$) δ 1.69-1.77 (m, 1H), 2.38-2.45 (m, 1H), 2.68-2.76 (m, 1H), 2.81-2.88 (m, 1H), 3.31-3.40 (m, 2H), 4.4 (t, 1H, J=5.4 Hz), 4.5 (t, 1H, J=4.9 Hz), 5.1 (q, 1H, J=7.8 Hz), 6.1 (t, 1H, J=5.9 Hz), 6.4 (d, 1H, J=8.3 Hz), 6.95-7.02 (m, 2H), 7.21-7.26 (m, 1H).

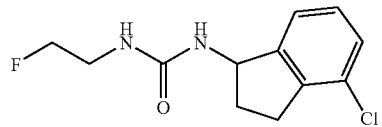

Synthesis of 1-(4-chloro-indan-1-yl)-3-(2-fluoro-ethyl)-urea

The title compound was generated from commercially available 3-(2-chloro-phenyl)-propionic acid according to general procedure D. The intermediates 4-chloro-1-indanone and 4-chloroindan-1-ylamine were isolated and characterized.

4-Chloro-1-indanone[12]: 5.56 g (62%) of the title indanone was obtained from 3-(2-chloro-phenyl)-propionic acid (10.00 g, 54.20 mmol), oxalyl chloride (32.50 mL, 372.55 mmol) of and AlCl$_3$ (8.00 g, 60.00 mmol) according to general procedure D. Spectroscopic data: $^1$H NMR (300 MHz, CDCl$_3$) δ 2.70-2.78 (m, 2H), 3.1 (t, 2H, J=5.9 Hz), 7.3 (t, 1H, J=7.6 Hz), 7.58 (d, 1H, J=7.6 Hz), 7.63 (d, 1H, J=7.6 Hz).

4-Chloro-indan-1-ylamine[xiii]: 2.09 g of the crude title amine (used in the next step without further purification) was obtained from 4-chloro-1-indanone (1.94 g, 11.60 mmol), NaBH$_3$CN (5.10 g, 81.16 mmol) and NH$_4$OAc (27.00 g, 350.29 mmol) according to the protocols as outlined in general procedure D above. Spectroscopic data: $^1$H NMR (300 MHz, CDCl$_3$) δ 1.6 (s, 2H), 1.67-1.75 (m, 1H), 2.47-2.59 (m, 1H), 2.77-2.92 (m, 1H), 2.98-3.12 (m, 1H), 4.37-4.48 (m, 1H), 7.13-7.27 (m, 3H).

1-(4-Chloro-indan-1-yl)-3-(2-fluoro-ethyl)-urea: The title urea was obtained from 4-chloro-indan-1-ylamine (2.09 g, crude taken from the previous step without further purification), diimidazole carbonyl (2.00 g, 12.33 mmol), fluoroethyl amine hydrochloride (1.24 g, 90% purity, 11.22 mmol) and diisopropyl ethyl amine (4.40 mL, 25.26 mmol) according to general procedure D above. Spectroscopic data: $^1$H NMR (500 MHz, DMSO-d$_6$) δ 1.70-1.77 (m, 1H), 2.39-2.45 (m, 1H), 2.74-2.80 (m, 1H), 2.89-2.95 (m, 1H), 3.31-3.39 (m, 2H), 4.4 (t, 1H, J=4.9 Hz), 4.5 (t, 1H, J=5.4 Hz), 5.2 (q, 1H, J=7.8 Hz), 6.1 (t, 1H, J=5.9 Hz), 6.4 (d, 1H, J=8.3 Hz), 7.17 (d, 1H, J=7.3 Hz), 7.24 (t, 1H, J=7.8 Hz), 7.3 (d, 1H, J=7.8 Hz). $^{13}$C NMR (126 MHz, DMSO-d$_6$) δ 29.5, 33.7, 40.5 (d, J=21.42 Hz), 55.8, 84.0 (d, J=164.5 Hz), 123.3, 127.8, 129.2, 130.3, 141.3, 148.3, 158.3.

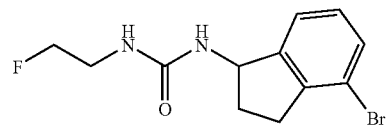

Synthesis of 1-(4-bromo-indan-1-yl)-3-(2-fluoro-ethyl)-urea

The title compound was generated from commercially available 3-(2-bromo-phenyl)-propionic acid according to general procedure D. The intermediates 4-bromo-1-indanone and 4-bromoindan-1-ylamine were isolated and characterized.

4-Bromo-1-indanone[xiv]: 5.69 g (62%) of the title indanone was obtained from 3-(2-bromo-phenyl)-propionic acid (10.00 g, 43.7 mmol), oxalyl chloride (26.00 mL, 295.99 mmol) and AlCl$_3$ (6.40 g, 48.00 mmol) according to the protocols as outlined in general procedure D above. Spectroscopic data: $^1$H NMR (300 MHz, CDCl$_3$) δ 2.7 (m, 2H), 3.1 (t, 2H, J=5.9 Hz), 7.3 (t, 1H, J=6.7 Hz), 7.7 (d, 1H, J=7.6 Hz), 7.8 (d, 1H, J=7.6 Hz).

4-Bromo-indan-1-ylamine: 2.29 g of the crude title compound (used in the next step without further purification) was obtained from 4-bromo-1-indanone (2.00 g, 9.50 mmol), NaBH$_3$CN (4.20 g, 66.84 mmol) and NH$_4$OAc (22.00 g, 285.42 mmol) according to the protocols as outlined in general procedure D above. Spectroscopic data: $^1$H NMR (300 MHz, CDCl$_3$) δ 1.58-1.74 (m, 3H), 2.46-2.58 (m, 1H), 2.75-2.90 (m, 1H), 2.95-3.09 (m, 1H), 4.39-4.50 (m, 1H), 7.04-7.15 (m, 1H), 7.2 (d, 1H, J=7.6 Hz), 7.4 (d, 1H, J=8.8 Hz).

1-(4-Bromo-indan-1-yl)-3-(2-fluoro-ethyl)-urea: The title urea was obtained from 4-bromo-indan-1-ylamine (2.29 g, 10.80 mmol), diimidazole carbonyl (1.80 g, 11.09 mmol), fluoroethyl amine hydrochloride (1.10 g, 90% purity, 9.95 mmol) and diisopropyl ethyl amine (3.80 mL, 21.82 mmol) according to the protocols as outlined in general procedure A above. Spectroscopic data: $^1$H NMR (500 MHz, DMSO-d$_6$) δ 1.69-1.77 (m, 1H), 2.37-2.44 (m, 1H), 2.71-2.79 (m, 1H), 2.84-2.91 (m, 1H), 3.30-3.39 (m, 2H), 4.4 (t, 1H, J=5.4 Hz), 4.5 (t, 1H, J=4.9 Hz), 5.2 (q, 1H, J=7.8 Hz), 6.1 (t, 1H, J=5.9 Hz), 6.4 (d, 1H, J=8.3 Hz), 7.1 (t, 1H, J=7.3 Hz), 7.2 (d, 1H, J=7.3 Hz), 7.4 (d, 1H, J=7.8 Hz). $^{13}$C NMR (126 MHz, DMSO-d$_6$) δ 31.6, 33.5, 40.5 (d, J=21.42 Hz), 56.1, 84.0 (d, J=164.5 Hz), 120.0, 123.8, 129.5, 130.7, 143.4, 148.2, 158.3.

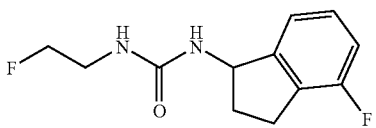

Synthesis of 1-(2-fluoro-ethyl)-3-(4-fluoro-indan-1-yl)-urea

The title compound was generated from commercially available 3-(2-fluoro-phenyl)-propionic acid according to general procedure D. The intermediates 4-fluoro-1-indanone and 4-fluoroindan-1-ylamine were isolated and characterized.

4-Fluoro-1-indanone[12]: 11.10 g (83%) of the title indanone was obtained from 3-(2-fluoro-phenyl)-propionic acid (15.00 g, 89.20 mmol) and thionyl chloride (9.80 mL, 134.35 mmol) and AlCl$_3$ (13.00 g, 97.50 mmol) according to the protocols as outlined in general procedure D above. Spectroscopic data: $^1$H NMR (300 MHz, CDCl$_3$) δ 2.71-2.77 (m, 2H), 3.2 (t, 2H, J=6.4, 5.6 Hz), 7.3 (t, 1H, J=8.8, 7.9 Hz), 7.34-7.41 (m, 1H), 7.6 (d, 1H, J=7.6 Hz).

4-Fluoro-indan-1-ylamine: 2.33 g of the crude amine was obtained from 4-fluoro-1-indanone (2.00 g, 13.33 mmol), NaBH$_3$CN (5.90 g, 93.89 mmol) and NH$_4$OAc (31.00 g, 402.18 mmol) according to the protocols as outlined in general procedure D above.

1-(2-Fluoro-ethyl)-3-(4-fluoro-indan-1-yl)-urea: The title urea was obtained from 4-fluoro-indan-1-ylamine (2.33 g, 15.43 mmol), diimidazole carbonyl (2.50 g, 19.80 mmol), fluoroethyl amine hydrochloride (1.50 g, 90% purity, 13.57 mmol) and diisopropyl ethyl amine (5.40 mL, 31.00 mol) according to the protocols as outlined in general procedure A above. Spectroscopic data: $^1$H NMR (500 MHz, DMSO-d$_6$) δ 1.70-1.78 (m, 1H), 2.39-2.47 (m, 1H), 2.71-2.79 (m, 1H), 2.90-2.97 (m, 1H), 3.31-3.39 (m, 2H), 4.4 (t, 1H J=5.4 Hz), 4.5 (t, 1H, J=4.9 Hz), 5.1 (q, 1H, J=7.8 Hz), 6.1 (t, 1H, J=5.4 Hz), 6.4 (d, 1H, J=8.8 Hz), 6.99-7.07 (m, 2H), 7.21-7.26 (m, 1H). $^{13}$C NMR (126 MHz, DMSO-d$_6$) δ 26.0, 34.4, 40.5 (d, J=20.16 Hz), 55.4 (d, J=2.4 Hz), 84.0 (d, J=164.5 Hz), 114.4 (d, J=20.1 Hz), 120.6 (d, J=2.9 Hz), 129.2 (d, J=18.7 Hz), 129.4 (d, J=7.2 Hz), 149.7 (d, J=5.3 Hz), 158.3, 159.2 (d, J=244.4 Hz).

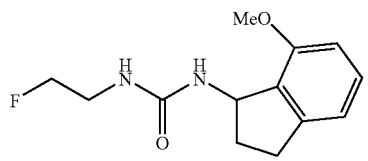

Synthesis of 1-(2-fluoro-ethyl)-3-(7-methoxy-indan-1-yl)-urea

The title compound was generated from commercially available 3-(3-methoxy-phenyl)-propionic acid according to general procedure D. The intermediates 7-methoxy-1-indanone and 7-methoxyindan-1-ylamine were isolated and characterized.

7-Methoxy-1-indanone[xv]: 4.20 g (93%) of the title indanone was obtained from 3-(3-methoxy-phenyl)-propionic acid (5.00 g, 27.70 mmol), oxalyl chloride (17.00 mL, 193.53 mmol) and AlCl$_3$ (3.70 g, 27.75 mmol) according to the protocols as outlined in general procedure D above. Spectroscopic data: $^1$H NMR (300 MHz, CDCl$_3$) δ 2.65-2.72 (m, 2H), 3.06-3.11 (m, 2H), 4.0 (s, 3H), 6.8 (d, 1H, J=8.2 Hz), 7.0 (d, 1H, J=7.0 Hz), 7.5 (t, 1H, J=8.2, 7.6 Hz).

7-Methoxy-indan-1-ylamine[xvi]: 1.62 g of the crude title amine was obtained from 7-methoxy-1-indanone (1.60 g, 10.00 mmol), NaBH$_3$CN (4.30 g, 68.43 mmol) and NH$_4$OAc (23.00 g, 298.39 mmol) according to the protocols as outlined in general procedure D above. Spectroscopic data: $^1$H NMR (300 MHz, CDCl$_3$) δ 1.70-1.84 (m, 1H), 2.0 (br s, 2H), 2.37-2.51 (m, 1H), 2.74-2.89 (m, 1H), 2.97-3.11 (m, 1H), 3.8 (s, 3H), 4.49-4.59 (m, 1H), 6.7 (d, 1H, J=8.2 Hz), 6.8 (d, 1H, J=7.3 Hz), 7.2 (t, 1H, J=7.6 Hz).

1-(2-Fluoro-ethyl)-3-(7-methoxy-indan-1-yl)-urea: The title compound was obtained from 7-methoxy-indan-1-ylamine (1.62 g, 9.93 mmol), diimidazole carbonyl (1.60 g, 9.86 mmol), fluoroethyl amine hydrochloride (1.00 g, 90% purity, 9.05 mmol) and diisopropyl ethyl amine (3.50 mL, 20.09 mmol) according to the protocols as outlined in general procedure A above. Spectroscopic data: $^1$H NMR (500 MHz, DMSO-d$_6$) δ 1.81-1.87 (m, 1H), 2.15-2.22 (m, 1H), 2.68-2.74 (m, 1H), 2.90-2.98 (m, 1H), 3.26-3.34 (m, 2H), 3.7 (s, 3H), 4.3 (t, 1H, J=5.4 Hz), 4.4 (t, 1H, J=4.9 Hz), 5.05-5.09 (m, 1H), 5.9 (t, 1H, J=5.9 Hz), 6.1 (d, 1H, J=6.8 Hz), 6.79 (d, 1H, J=8.3 Hz), 6.84 (d, 1H, J=7.8 Hz), 7.2 (t, 1H, J=7.8 Hz). $^{13}$C NMR (126 MHz, DMSO-d$_6$) δ 30.7, 34.8, 40.52 (d, J=21.42 Hz), 53.2, 55.8, 84.13 (d, J=163.8 Hz), 109.4, 117.5, 130.3, 130.9, 146.7, 156.9, 158.1.

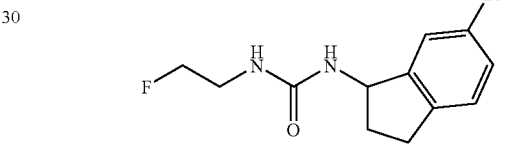

Synthesis of 1-(6-bromo-indan-1-yl)-3-(2-fluoro-ethyl)-urea

The title compound was generated from commercially available 3-(4-bromo-phenyl)-propionic acid according to the general procedure D. The intermediates 6-bromo-1-indanone and 6-bromoindan-1-ylamine were isolated and characterized.

6-Bromo-1-indanone[12]: The title indanone was generated from 3-(4-bromo-phenyl)-propionic acid (10.00 g, 43.60 mmol), oxalyl chloride (26.20 mL, 0.30 mol) and AlCl$_3$ (6.00 g, 45.00 mmol) according to the protocols as outlined in general procedure D. Spectroscopic data: $^1$H NMR (300 MHz, CDCl$_3$) δ 2.69-2.76 (m, 2H), 3.06-3.13 (m, 2H), 7.4 (d, 1H, J=7.9 Hz), 7.7 (dd, 1H, J=8.2 Hz), 7.9 (br s, 1H).

6-Bromo-indan-1-ylamine: The title indanamine was generated from 6-bromo-1-indanone (2.00 g, 9.50 mmol), NaBH$_3$CN (4.20 g, 66.84 mmol) and NH$_4$OAc (22.00 g, 0.29 mol) according to the protocols as outlined in general procedure C. Spectroscopic data: $^1$H NMR (300 MHz, CDCl$_3$) δ 1.59-1.73 (m, 3H), 2.44-2.56 (m, 1H), 2.70-2.82 (m, 1H), 2.84-2.98 (m, 1H), 4.29-4.40 (m, 1H), 6.98-7.18 (m, 1H), 7.26-7.38 (m, 1H), 7.4 (s, 1H).

1-(6-Bromo-indan-1-yl)-3-(2-fluoro-ethyl)-urea: The title urea was afforded from 6-bromo-indan-1-ylamine (2.00 g, 9.43 mmol), diimidazole carbonyl (1.50 g, 9.24 mmol), fluoroethyl amine hydrochloride (940 mg, 90% purity, 8.50 mmol) and diisopropylethyl amine (3.30 mL, 18.95 mmol) according to the protocols as outlined in general procedure A above. Spectroscopic data: $^1$H NMR (500 MHz, DMSO-d$_6$) δ

1.67-1.75 (m, 1H), 2.36-2.42 (m, 1H), 2.68-2.75 (m, 1H), 2.81-2.87 (m, 1H), 3.31-3.40 (m, 2H), 4.4 (t, 1H, J=4.9 Hz), 4.5 (t, 1H, J=5.4 Hz), 5.1 (q, 1H, J=7.8 Hz), 6.1 (t, 1H, J=5.9 Hz), 6.4 (d, 1H, J=8.3 Hz), 7.2 (d, 1H, J=7.8 Hz), 7.3 (s, 1H), 7.35-7.38 (m, 1H).

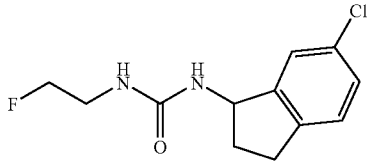

Synthesis of 1-(6-chloro-indan-1-yl)-3-(2-fluoro-ethyl)-urea

The title compound was generated from commercially available 3-(4-chloro-phenyl)-propionic acid according to the general procedure D. The intermediates 6-chloro-1-indanone and 6-chloroindan-1-ylamine were isolated and characterized.

6-Chloro-1-indanone[12]: 4.50 g (50%) of the title indanone was obtained from 3-(4-chloro-phenyl)-propionic acid (10.00 g, 54.00 mmol), oxalyl chloride (32.50 mL, 0.36 mol) and AlCl$_3$ (7.22 g, 54.15 mmol) according to the protocols as outlined in general procedure D above. Spectroscopic data: $^1$H NMR (300 MHz, CDCl$_3$) δ 2.64-2.78 (m, 2H), 3.04-3.17 (m, 2H), 7.4 (d, 1H, J=7.9 Hz), 7.5 (dd, 1H, J=8.2 Hz), 7.65-7.75 (m, 1H).

6-Chloro-indan-1-ylamine: 1.27 g of the crude amine was obtained from 6-chloro-1-indanone (1.42 g, 8.50 mmol), NaBH$_3$CN (3.75 g, 59.68 mmol) and NH$_4$OAc (19.70 g, 0.26 mol) according to the protocols as outlined in general procedure D above. Spectroscopic data: $^1$H NMR (300 MHz, CDCl$_3$) δ 1.42-1.89 (m, 3H), 2.46-2.59 (m, 1H), 2.66-3.18 (m, 2H), 4.30-4.41 (m, 1H), 7.00-7.35 (m, 3H).

1-(6-Chloro-indan-1-yl)-3-(2-fluoro-ethyl)-urea: The title compound was obtained from 6-chloro-indan-1-ylamine (1.27 g, 7.58 mmol), diimidazole carbonyl (1.30 g, 10.30 mmol), fluoroethyl amine hydrochloride (755 mg, 90% purity, 6.83 mmol) and diisopropyl ethyl amine (2.64 mL, 15.16 mmol) according to the protocols as outlined in general procedure A above. Spectroscopic data: $^1$H NMR (500 MHz, DMSO-d$_6$) δ 1.68-1.76 (m, 1H), 2.37-2.44 (m, 1H), 2.70-2.77 (m, 1H), 2.82-2.89 (m, 1H), 3.31-3.40 (m, 2H), 4.4 (t, 1H, J=4.9 Hz), 4.5 (t, 1H, J=5.4 Hz), 5.1 (q, 1H, J=8.3 Hz), 6.1 (t, 1H, J=5.9 Hz), 6.4 (d, 1H, J=8.3 Hz), 7.19 (s, 1H), 7.22-7.28 (m, 2H). $^{13}$C NMR (126 MHz, DMSO-d$_6$) δ 29.8, 34.8, 40.6 (d, J=20.16 Hz), 55.1, 84.0 (d, J=164.0 Hz), 124.4, 126.9, 127.8, 131.5, 142.3, 148.3, 158.4.

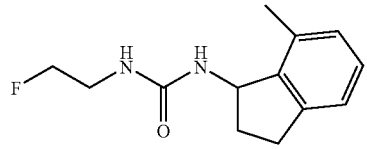

Synthesis of 1-(2-fluoro-ethyl)-3-(7-methyl-indan-1-yl)-urea

The title compound was generated from commercially available 3-(3-methyl-phenyl)-propionic acid according to the general procedure D. The intermediates 7-methyl-1-indanone and 7-methylindan-1-ylamine were isolated and characterized.

7-Methyl-1-indanone[12]: 3-(3-Methyl-phenyl)-propionic acid (10.00 g, 61.00 mmol) was added all at once to methanesulfonic acid at 110° C. The resulting mixture was stirred for 3 hours, then slowly quenched into ice-water. The solution was extracted with EtOAc (3×200 mL) and the combined extracts were washed with H$_2$O (3×150 mL), saturated NaHCO$_3$ (3×150 mL) and brine (1×150 mL), then dried over MgSO$_4$ and concentrated. Column chromatography using hexane:EtOAc (4.5:0.5) as eluant gave 2.67 g (30%) of the title indanone and 2.00 g (22.5%) of the undesired 5-methyl-1-indanone. Spectroscopic data for the desired title indanone: $^1$H NMR (300 MHz, CDCl$_3$) δ 2.60-2.70 (m, 5H), 3.03-3.13 (m, 2H), 7.1 (d, 1H, J=6.7 Hz), 7.3 (d, 1H, J=7.9 Hz), 7.4 (t, 1H, J=7.3 Hz).

7-Methyl-indan-1-ylamine: 2.77 g of the crude title compound was obtained from 7-methyl-1-indanone (2.67 g, 18.30 mmol), NaBH$_3$CN (8.00 g, 0.13 mol) and NH$_4$OAc (42.30 g, 0.55 mol) according to the protocols as outlined in general procedure D. Spectroscopic data: $^1$H NMR (300 MHz, CDCl$_3$) δ 1.79-1.89 (m, 3H), 2.28-2.42 (m, 4H), 2.74-2.90 (m, 1H), 3.01-3.17 (m, 1H), 4.36-4.50 (m, 1H), 6.90-7.19 (m, 3H).

1-(2-Fluoro-ethyl)-3-(7-methyl-indan-1-yl)-urea: The title compound was obtained from 7-methyl-indan-1-ylamine (2.77 g, 18.84 mmol), diimidazole carbonyl (3.10 g, 19.11 mmol), fluoroethyl amine hydrochloride (1.90 g, 90% purity, 17.19 mmol) and diisopropyl ethyl amine (6.60 mL, 37.89 mmol) according to the protocols as outlined in general procedure A above. Spectroscopic data: $^1$H NMR (500 MHz, DMSO-d$_6$) δ 1.77-1.83 (m, 1H), 2.20-2.28 (m, 4H), 2.69-2.76 (m, 1H), 2.92-2.99 (m, 1H), 3.27-3.36 (m, 2H), 4.3 (t, 1H, J=5.4 Hz), 4.4 (t, 1H, J=5.4 Hz), 5.15-5.19 (m, 1H), 5.9 (t, 1H, J=5.9 Hz), 6.2 (d, 1H, J=8.8 Hz), 7.0 (d, 1H, J=7.3 Hz), 7.05 (d, 1H, J=7.3 Hz), 7.11 (t, 1H, J=7.3 Hz). $^{13}$C NMR (126 MHz, DMSO-d$_6$) δ 18.6, 30.5, 34.4, 40.5 (d, J=20.16 Hz), 54.1, 84.1 (d, J=164.0 Hz), 122.6, 128.4, 128.5, 135.1, 142.8, 144.2, 158.0.

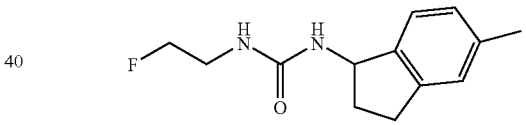

Synthesis of 1-(2-fluoro-ethyl)-3-(5-methyl-indan-1-yl)-urea

The title compound was generated from commercially available 3-(4-methyl-phenyl)-propionic acid according to the general procedure D. The intermediates 5-methyl-1-indanone and 5-methylindan-1-ylamine were isolated and characterized.

5-Methyl-1-indanone[12]: Spectroscopic data: $^1$H NMR (300 MHz, CDCl$_3$) δ 2.5 (s, 3H), 2.63-2.74 (m, 2H), 3.04-3.15 (m, 2H), 7.2 (d, 1H, J=8.5 Hz), 7.3 (s, 1H), 7.7 (d, 1H, J=7.6 Hz).

5-Methyl-indan-1-ylamine: 1.86 g of the crude title amine was obtained from 5-methyl-1-indanone (2.00 g, 13.00 mmol), NaBH$_3$CN (6.02 g, 95.80 mmol) and NH$_4$OAc (31.70 g, 0.41 mol) according to the protocols as outlined in general procedure D above. Spectroscopic data: $^1$H NMR (300 MHz, CDCl$_3$) δ 1.62-1.78 (m, 3H), 2.3 (s, 3H), 2.40-2.54 (m, 1H), 2.73-2.82 (m, 1H), 2.84-2.96 (m, 1H), 4.27-4.42 (m, 1H), 6.98-7.13 (m, 2H), 7.2 (d, 1H, J=7.9 Hz).

1-(2-Fluoro-ethyl)-3-(5-methyl-indan-1-yl)-urea: The title urea was obtained from 5-methyl-indan-1-ylamine (1.86 g, 12.65 mmol) of, diimidazole carbonyl (2.00, 12.33 mmol), fluoroethyl amine hydrochloride (1.30 g, 90% purity, 11.76 mmol) and diisopropyl ethyl amine (4.40 mL, 25.26 mmol) according to the protocols as outlined in general procedure A above. Spectroscopic data: $^1$H NMR (500 MHz, DMSO-$d_6$) δ 1.61-1.69 (m, 1H), 2.3 (s, 3H), 2.33-2.39 (m, 1H), 2.67-2.74 (m, 1H), 2.80-2.85 (m, 1H), 3.30-3.38 (m, 2H), 4.4 (t, 1H, J=5.4 Hz), 4.5 (t, 1H, J=4.9 Hz), 5.0 (q, 1H, J=7.8 Hz), 6.0 (t, 1H, J=4.4 Hz), 6.3 (d, 1H, J=8.3 Hz), 7.0 (d, 1H, J=7.8 Hz), 7.02 (s, 1H), 7.1 (d, 1H, J=7.3 Hz). $^{13}$C NMR (126 MHz, DMSO-$d_6$) δ 21.6, 30.1, 34.9, 40.5 (d, J=21.42 Hz), 54.9, 84.1 (d, J=164.0 Hz), 124.2, 125.7, 127.7, 137.0, 142.6, 143.5, 158.4.

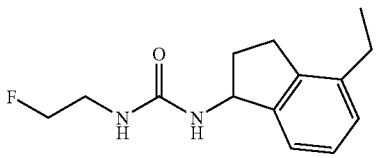

Synthesis of 1-(4-ethyl-indan-1-yl)-3-(2-fluoro-ethyl)-urea

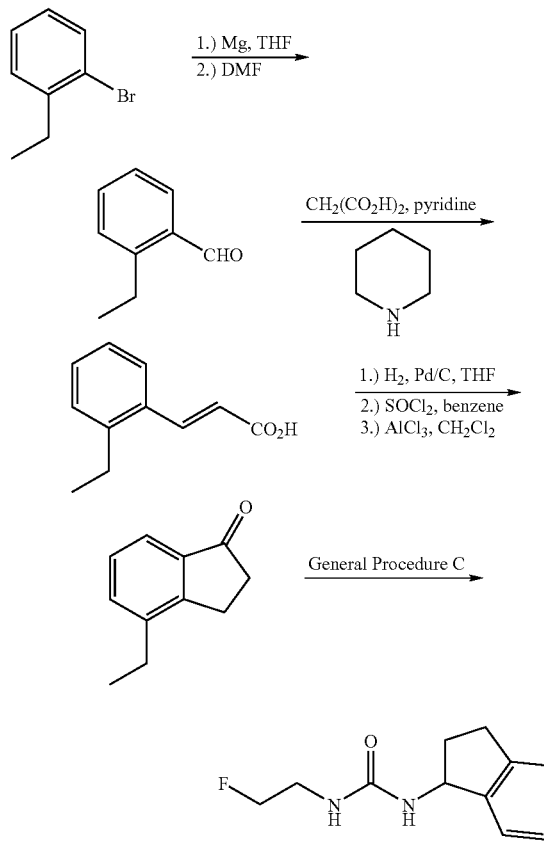

The title compound was generated from commercially available 1-bromo2-ethylbenzene according to the scheme above. The intermediates 2-ethylbenzaldehyde, 3-(2-ethyl-phenyl)-acrylic acid, 4-ethyl-1-indanone and 4-ethylindan-1-ylamine were isolated and characterized.

2-Ethyl-benzaldehyde[vii]: A solution of 1-bromo-2-ethyl-benzene (5.00 g, 27.02 mmol), Mg (4.00 g, 0.16 mol) and a catalytic amount of I2 in THF was refluxed for 2 hours. After cooling the reaction mixture to 0° C., DMF (10.0 mL) was added and the mixture was stirred for 30 minutes. It was then quenched with 10% HCl and the resulting solution was extracted with Et$_2$O (3×200 mL). The combined organic extracts were washed with H$_2$O (2×200 mL), brine (1×200 mL), dried over MgSO$_4$ and concentrated to give the title compound.

3-(2-Ethyl-phenyl)-acrylic acid[xviii]: To a solution of 2-ethyl-benzaldehyde (18.40 g, 0.14 mol) and malonic acid (28.00 g, 0.27 mol) in pyridine was added 10.00 mL of piperidine and the resulting mixture was slowly refluxed for 3 hours. After cooling to room temperature, the reaction mixture was diluted with ice water, acidified to pH<1. The resulting solid was filtered, washed with water and dried under vacuum to give the title compound.

4-Ethyl-indan-1-one: 3-(2-Ethyl-phenyl)-acrylic acid (17.00 g, 96.48 mmol) in THF was mixed with Pd/C (1.50 g) and hydrogenated at 50 psi for 6 hours. The resulting mixture was filtered through a pad of celite and the filtrate was concentrated to give 3-(2-ethyl-phenyl)-propionic acid. The acid was reacted with SOCl$_2$ (5.00 mL, 68.55 mmol) and AlCl$_3$ (6.70 g, 50.25 mmol) according to the protocols as outlined in general procedure D to give the title compound.

4-Ethyl-indan-1-ylamine: 4-Ethyl-indan-1-one (5.00 g, 31.21 mmol), NaBH$_3$CN (13.70 g, 0.22 mol) and NH$_4$OAc (72.00 g, 0.93 mol) in isopropanol were reacted according to the protocols as outlined in general procedure C to give the desired amine.

1-(4-Ethyl-indan-1-yl)-3-(2-fluoro-ethyl)-urea: 4-ethyl-indan-1-ylamine (3.0 g, 18.6 mmol), diimidazole carbonyl (3.02 g, 18.61 mmol), fluoroethyl amine hydrochloride (1.85 g, 90 purity, 16.73 mmol) and diisopropylethyl amine (6.50 mL, 37.32 mmol) in acetonitrle were reacted according to the protocols as outlined in general procedure A above to afford the title compound. Spectroscopic data: $^1$H NMR (300 MHz, DMSO-$d_6$) δ 1.1 (t, J=7.9, 7.3 Hz, 3H), 1.59-1.73 (m, 1H), 2.33-2.45 (m, 1H), 2.49-2.60 (m, 2H), 2.63-2.75 (m, 1H), 2.82-2.93 (m, 1H), 3.25-3.33 (m, 1H), 3.4 (q, J=5.3 Hz, 1H), 4.3 (t, J=5.3 Hz, 1H), 4.5 (t, J=5.0 Hz, 1H), 5.1 (q, J=7.6 Hz, 1H), 6.0 (t, J=6.2 Hz, 1H), 6.3 (d, J=8.2 Hz, 1H), 7.0 (d, J=7.0 Hz, 2H), 7.1 (t, J=7.6 Hz, 1H).

General Procedure E for the Synthesis of Fluoroethyl Substituted Indan Ureas

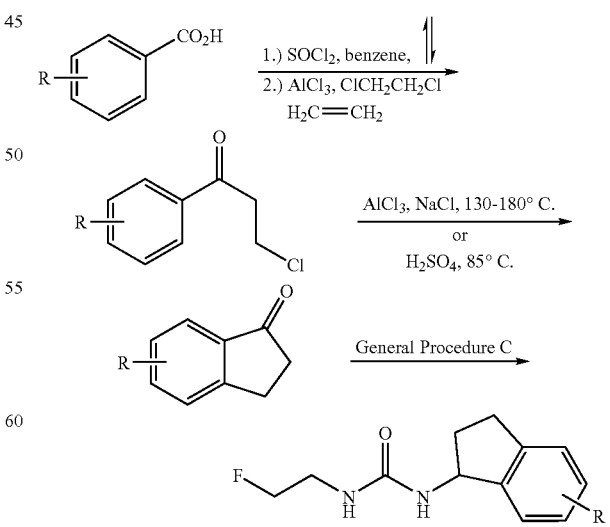

A mixture of SOCl$_2$ (1.5 eq) and substituted benzoic acids in benzene was refluxed until no more gas evolution was observed. After cooling to room temperature the mixture was concentrated on a rotary evaporator. The concentrate was taken up in dichloroethane and added to a solution of AlCl₃ (1.0 eq) in dichloroethane at 10-20° C. Ethylene was bubbled for 4 hours after which the resulting mixture was stirred overnight and quenched into 4 N HCl. The resulting layers were separated and the aqueous layer was extracted with Et₂O (3×250 mL). The combined organic extracts were washed with H₂O (3×150 mL), saturated NaHCO₃ (3×150 mL), brine (1×150 mL), dried over MgSO₄ and concentrated. The concentrate was added to a slurry of AlCl₃ (9.0 g, 10 eq) and NaCl (2.4 g, 6 eq) at 130° C. The resulting mixture was stirred at 180° C. for 2 hours. Alternatively, this concentrate was mixed with concentrated sulfuric acid and the resulting mixture was stirred at 85° C. one hour. The reaction mixture was cooled to room temperature and ice was slowly added, followed by concentrated HCl. The resulting mixture was extracted with CH₂Cl₂ (3×500 mL) and the combined organic extracts were concentrated and purified by column chromatography using hexane:EtOAc (4:1) as eluant to give the desired substituted indanones$^{xix}$. Thus, the title fluoroethyl ureas were obtained from these indanones according the protocol described in general procedure C.

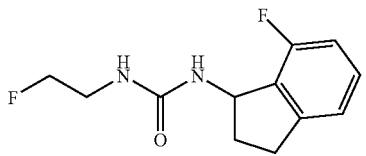

Synthesis of 1-(2-fluoro-ethyl)-3-(7-fluoro-indan-1-yl)-urea

The title compound was generated from commercially available 2-fluororobenzoic acid according to the general procedure E described above. The intermediates 7-fluoro-1-indanone and 7-fluoro-indan-1-ylamine were isolated and characterized.

7-Fluoro-1-indanone: 6.85 g (32%) of the title indanone was obtained from 2-fluoro-benzoic acid (20.00 g, 0.14 mol), SOCl₂ (15.60 mL, 0.21 mol), AlCl₃ (19.00 g, 0.14 mol), an additional AlCl₃ (285.50 g, 2.14 mol) and NaCl (75.10 g, 1.29 mol) according to the protocols as outlined in general procedure E above. Spectroscopic data: ¹H NMR (300 MHz, CDCl₃) δ 2.67-2.80 (m, 2H), 3.2 (t, 2H, J=5.9 Hz), 7.0 (t, 1H, J=8.5 Hz), 7.3 (d, 1H, J=7.6 Hz), 7.6 (m, 1H).

7-Fluoro-indan-1-ylamine: The title amine was obtained from 7-fluoro-1-indanone (5.82 g, 39.00 mmol), NaBH₃CN (17.10 g, 0.27 mol) and NH₄OAc (90.00 g, 1.17 mol) according to the protocols as outlined in general procedure C above.

1-(2-Fluoro-ethyl)-3-(7-fluoro-indan-1-yl)-urea: The title urea was obtained from 7-fluoro-indan-1-ylamine (3.35 g, 22.16 mmol), diimidazole carbonyl (3.60 g, 22.19 mmol), fluoroethyl amine hydrochloride (2.20 g, 90% purity, 19.90 mmol) and diisopropyl ethyl amine (7.72 mL, 44.32 mmol) according to the protocols as outlined in general procedure A. Spectroscopic data: ¹H NMR (300 MHz, DMSO-d₆) δ 1.76-1.88 (m, 1H), 2.28-2.41 (m, 1H), 2.73-2.85 (m, 1H), 2.92-3.05 (m, 1H), 3.25-3.40 (m, 2H), 4.3 (t, 1H, J=5.0 Hz), 4.5 (t, 1H, J=5.3 Hz), 5.23-5.36 (m, 1H), 5.9 (t, 1H, J=5.6 Hz), 6.4 (d, 1H, J=8.2 Hz), 7.0 (t, 1H, J=9.7 Hz), 7.1 (d, 1H, J=7.3 Hz), 7.19-7.31 (m, 1H). ¹³C NMR (75 MHz, DMSO-d₆) δ 30.7, 34.9, 40.5 (d, J=20.25 Hz), 52.8, 84.0 (d, J=164.1 Hz), 113.8 (d, J=20.7 Hz), 121.3 (d, J=3.4 Hz), 130.4, 130.6 (d, J=6.9 Hz), 148.0 (d, J=4.6 Hz), 157.8, 159.8 (d, J=247.8 Hz).

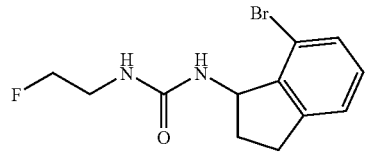

Synthesis of 1-(7-bromo-indan-1-yl)-3-(2-fluoro-ethyl)-urea

The title compound was generated from commercially available 2-bromobenzoic acid according to the general procedure E described above. The intermediates 7-bromo-1-indanone and 7-bromo-indan-1-ylamine were isolated and characterized.

7-Bromo-1-indanone: 9.68 g (31%) of the title indanone was obtained from 2-bromo-benzoic acid (30.00 g, 0.15 mol), SOCl₂ (16.50 mL, 0.23 mol), AlCl₃ (20.00 g, 0.15 mol), an additional AlCl₃ (200.00 g, 1.50 mol) and NaCl (52.30 g, 0.89 mol) according to the protocols as outlined in general procedure E. Spectroscopic data: ¹H NMR (300 MHz, CDCl₃) δ 2.69-2.79 (m, 2H), 3.04-3.14 (m, 2H), 7.35-7.45 (m, 2H), 7.49-7.55 (m, 1H).

7-Bromo-indan-1-ylamine: 4.84 g of the crude amine was obtained from 7-bromo-1-indanone (8.00 g, 38.00 mmol), NaBH₃CN (16.70 g, 0.27 mol) and NH₄OAc (88.00 g, 1.14 mol) according to the protocols as outlined in general procedure C.

1-(7-Bromo-indan-1-yl)-3-(2-fluoro-ethyl)-urea: The title compound was obtained from 7-bromo-indan-1-ylamine (2.42 g, 11.40 mmol), diimidazole carbonyl (1.85 g, 14.65 mmol), fluoroethyl amine hydrochloride (1.14 g, 90% purity, 10.31 mmol) and diisopropyl ethyl amine (4.00 mL, 22.97 mmol) outlined in general procedure A above. Spectroscopic data: ¹H NMR (300 MHz, DMSO-d₆) δ 1.82-1.91 (m, 1H), 2.19-2.32 (m, 1H), 2.78-2.89 (m, 1H), 3.00-3.12 (m, 1H), 3.24-3.39 (m, 2H), 4.3 (t, 1H, J=5.0 Hz), 4.5 (t, 1H, J=5.0 Hz), 5.08-5.15 (m, 1H), 5.9 (t, 1H, J=5.9 Hz), 6.3 (d, 1H, J=7.9 Hz), 7.2 (t, 1H, J=7.6 Hz), 7.3 (d, 1H, J=7.3 Hz), 7.4 (d, 1H, J=7.6 Hz). ¹³C NMR (75 MHz, DMSO-d₆) δ 31.2, 34.1, 40.5 (d, J=20.25 Hz), 56.1, 84.1 (d, J=164.1 Hz), 120.3, 124.7, 130.7 (2C), 143.5, 147.5, 157.9.

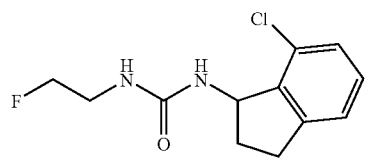

Synthesis of 1-(7-chloro-indan-1-yl)-3-(2-fluoro-ethyl)-urea

The title compound was generated from commercially available 2-chlorobenzoic acid according to the general procedure E described above. The intermediates 7-chloro-1-indanone and 7-chloro-indan-1-ylamine were isolated and characterized.

7-Chloro-1-indanone: 4.13 g (31%) of the title indanone was obtained from 2-chloro-benzoic acid (10.00 g, 64.00 mmol), SOCl₂ (7.00 mL, 95.97 mmol), AlCl₃ (8.50 g, 63.75 mmol), an additional AlCl₃ (85.20 g, 0.64 mol) and NaCl (22.40 g, 0.38 mol) according to the protocols as outlined in general procedure E. Spectroscopic data: $^1$H NMR (300 MHz, CDCl$_3$) δ 2.65-2.75 (m, 2H), 3.1 (t, 2H, J=6.7, 5.6 Hz), 7.3 (d, 1H, J=7.6 Hz), 7.4 (d, 1H, J=7.6 Hz), 7.5 (t, 1H, J=7.6 Hz).

7-Chloro-indan-1-ylamine: 1.00 g of the crude title amine was obtained from 7-chloro-1-indanone (4.13 g, 25.00 mmol), NaBH$_3$CN (11.00 g, 0.18 mol) and NH$_4$OAc (57.40 g, 0.74 mol) according to the protocols as outlined in general procedure C. Spectroscopic data: $^1$H NMR (300 MHz, CDCl$_3$) δ 1.7 (br s, 2H), 1.82-1.92 (m, 1H), 2.37-2.51 (m, 1H), 2.79-2.94 (m, 1H), 3.07-3.19 (m, 1H), 4.48-4.59 (m, 1H), 7.07-7.16 (m, 3H).

1-(7-Chloro-indan-1-yl)-3-(2-fluoro-ethyl)-urea: The title compound was obtained from 7-chloro-indan-1-ylamine (1.00 g, 5.97 mmol), diimidazole carbonyl (970 mg, 5.98 mmol), fluoroethyl amine hydrochloride (600 mg, 90% purity, 5.43 mmol) and diisopropyl ethyl amine (2.00 mL, 11.48 mmol) according to the protocols as outlined in general procedure A above. Spectroscopic data: $^1$H NMR (300 MHz, DMSO-d$_6$) δ 1.79-1.92 (m, 1H), 2.21-2.34 (m, 1H), 2.74-2.87 (m, 1H), 2.96-3.10 (m, 1H), 3.24-3.39 (m, 2H), 4.3 (t, 1H J=5.0 Hz), 4.5 (t, 1H, J=5.0 Hz), 5.14-5.25 (m, 1H), 5.9 (t, 1H, J=5.6 Hz), 6.3 (d, 1H, J=8.2 Hz), 7.17-7.29 (m, 3H). $^{13}$C NMR (75 MHz, DMSO-d$_6$) δ 30.9, 34.2, 40.5 (d, J=20.25 Hz), 54.6, 84.1 (d, J=164.1 Hz), 124.1, 127.6, 130.4, 131.0, 141.6, 147.4, 157.9.

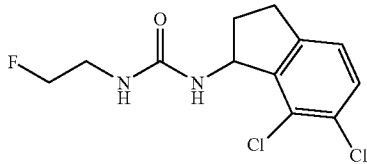

Synthesis of 1-(6,7-dichloro-indan-1-yl)-3-(2-fluoro-ethyl)-urea

The title compound was generated from commercially available 2,3-dichlorobenzoic acid according to the general procedure E described above. The intermediates 6,7-dichloro-1-indanone and 6,7-dichloro-indan-1-ylamine were isolated and characterized.

6,7-Dichloro-1-indanone:[xx] Spectroscopic data: $^1$H NMR (300 MHz, CDCl$_3$) δ 2.75-2.81 (m, 2H), 3.06-3.11 (m, 2H), 7.3 (d, 1H, J=8.2 Hz), 7.6 (d, 1H, J=7.92 Hz).

6,7-Dichloro-indan-1-ylamine[13]: 6,7-Dichloro-1-indanone (3.48 g, 17.30 mmol), NaBH$_3$CN (7.62 g, 0.12 mol) and NH$_4$OAc (40.00 g, 0.52 mol) in isopropanol were reacted according to the protocols as outlined in general procedure C to give the title amine. Spectroscopic data: $^1$H NMR (300 MHz, CDCl$_3$) δ 1.83-1.96 (m, 3H), 2.38-2.52 (m, 1H), 2.78-2.93 (m, 1H), 3.04-3.19 (m, 1H), 4.41-4.63 (m, 1H), 7.1 (d, 1H, J=7.9 Hz), 7.3 (d, 1H, J=7.9 Hz).

1-(6,7-Dichloro-indan-1-yl)-3-(2-fluoro-ethyl)-urea: Title compound was produced from 6,7-dichloro-indan-1-ylamine (2.90 g, 14.36 mmol), diimidazole carbonyl (2.30 g, 14.18 mmol), fluoroethyl amine hydrochloride (1.40 g, 90% purity, 12.66 mmol) and diisopropylethyl amine (5.00 mL, 28.71 mmol) according to the protocols as outlined in general procedure A above. Spectroscopic data: $^1$H NMR (300 MHz, DMSO-d$_6$) δ 1.83-1.93 (m, 1H), 2.26-2.39 (m, 1H), 2.73-2.87 (m, 1H), 2.96-3.09 (m, 1H), 3.24-3.39 (m, 2H), 4.3 (t, 1H, J=5.3 Hz), 4.5 (t, 1H, J=4.7 Hz), 5.19-5.27 (m, 1H), 5.9 (t, 1H, J=6.4 Hz), 6.4 (d, 1H, J=7.3 Hz), 7.3 (d, 1H, J=8.2 Hz), 7.5 (d, 1H, J=7.9 Hz).

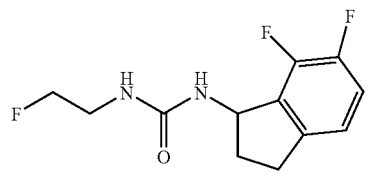

Synthesis 1-(6,7-difluoro-indan-1-yl)-3-(2-fluoro-ethyl)-urea

The title compound was generated from commercially available 2,3-difluorobenzoic acid according to the general procedure E described above. The intermediates 6,7-difluoro-1-indanone and 6,7-difluoro-indan-1-ylamine were isolated and characterized.

6,7-Difluoro-1-indanone[12]: 2,3-Difluoro-benzoic acid (10.30 g, 65.14 mmole), SOCl$_2$ (7.20 mL, 98.71 mmol), AlCl$_3$ (8.70 g, 65.25 mmol), an additional AlCl$_3$ (87.00 g, 0.65 mol) and NaCl (23.00 g, 0.39 mol) were reacted according to the protocols as outlined in general procedure E to give the title indanone. Spectroscopic data: $^1$H NMR (300 MHz, CDCl$_3$) δ 2.73-2.80 (m, 2H), 3.09-3.16 (m, 2H), 7.11-7.23 (m, 1H), 7.35-7.46 (m, 1H).

6,7-Difluoro-indan-1-ylamine: 6,7-Difluoro-1-indanone (6.000 g, 35.70 mmol), NaBH$_3$CN (15.70 g, 0.25 mol) and NH$_4$OAc (82.60 g, 1.07 mol) in isopropanol were reacted according to the protocols as outlined in general procedure C to give the title amine. Spectroscopic data: $^1$H NMR (300 MHz, CDCl$_3$) δ 1.7 (br s, 2H), 1.78-1.90 (m, 1H), 2.44-2.57 (m, 1H), 2.72-2.87 (m, 1H), 2.95-3.09 (m, 1H), 4.7 (t, 1H, J=6.7 Hz), 6.86-7.00 (m, 2H).

1-(6,7-Difluoro-indan-1-yl)-3-(2-fluoro-ethyl)-urea: The title compound was obtained from 6,7-difluoro-indan-1-ylamine (1.50 g, 9.00 mmol), diimidazole carbonyl (1.50 g, 9.24 mmol), fluoroethyl amine hydrochloride (894 mg, 90% purity, 8.09 mmol) and diisopropylethyl amine (3.20 mL, 18.37 mmol) according to the protocols as outlined in general procedure A above. Spectroscopic data: $^1$H NMR (300 MHz, DMSO-d$_6$) δ 1.79-1.92 (m, 1H), 2.33-2.45 (m, 1H), 2.70-2.82 (m, 1H), 2.88-3.01 (m, 1H), 3.26-3.41 (m, 2H), 4.3 (t, 1H, J=4.4 Hz), 4.5 (t, 1H, J=4.1 Hz), 5.4 (q, 1H, J=7.3 Hz), 6.0 (t, 1H, J=5.6 Hz), 6.5 (d, 1H, J=8.5 Hz), 6.99-7.10 (m, 1H), 7.19-7.31 (m, 1H).

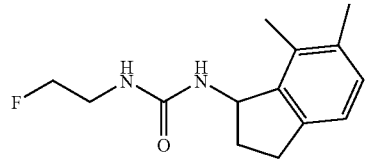

Synthesis of 1-(6,7-dimethyl-indan-1-yl)-3-(2-fluoro-ethyl)-urea

The title compound was generated from commercially available 2,3-dimethylbenzoic acid according to the general procedure E described above. The intermediates 6,7-dimethyl-1-indanone and 6,7-dimethyl-indan-1-ylamine were isolated and characterized.

6,7-Dimethyl-1-indanone[xxi]: Sulfuric acid was used in the key cyclization step. Spectroscopic data: $^1$H NMR (300 MHz, CDCl$_3$) δ 2.3 (s, 3H), 2.6 (s, 3H), 2.63 (t, 2H, J=6.2 Hz), 3.0 (t, 2H, J=5.9 Hz), 7.2 (d, 1H, J=7.9 Hz), 7.3 (d, 1H, J=7.9 Hz).

6,7-Dimethyl-indan-1-ylamine: 6,7-Dimethyl-1-indanone (2.50 g, 15.60 mmol), NaBH₃CN (6.90 g, 0.11 mol) and NH₄OAc (36.00 g, 0.47 mol) in isopropanol were reacted according to the protocols as outlined in general procedure E to afford the title indanamine. Spectroscopic data: ¹H NMR (300 MHz, CDCl₃) δ 1.6 (br s, 2H), 1.83-1.96 (m, 1H), 2.01-2.11 (m, 1H), 2.26 (s, 3H), 2.31 (s, 3H), 2.72-2.87 (m, 1H), 3.05-3.18 (m, 1H), 4.42-4.50 (m, 1H), 6.95-7.09 (m, 2H).

1-(6,7-Dimethyl-indan-1-yl)-3-(2-fluoro-ethyl)-urea: The title urea was obtained from 6,7-dimethyl-indan-1-ylamine (2.51 g, 15.60 mmol), diimidazole carbonyl (2.53 g, 15.59 mmol), fluoroethyl amine hydrochloride (1.60 g, 90% purity, 14.47 mmol) and diisopropylethyl amine (5.40 mL, 31.00 mmol) according to the protocols as outlined in general procedure A above. Spectroscopic data: ¹H NMR (300 MHz, DMSO-d₆) δ 1.76-1.90 (m, 1H), 2.1 (s, 3H), 2.2 (s, 3H), 2.20-2.32 (m, 1H), 2.62-2.74 (m, 1H), 2.85-2.98 (m, 1H), 3.23-3.38 (m, 2H), 4.3 (t, 1H, J=5.3 Hz), 4.4 (t, 1H, J=5.0 Hz), 5.09-5.18 (m, 1H), 5.8 (t, 1H, J=5.9 Hz), 6.2 (d, 1H, J=8.5 Hz), 6.9 (d, 1H, J=7.6 Hz), 7.0 (d, 1H, J=7.6 Hz).

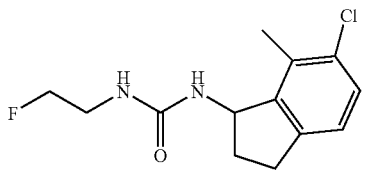

Synthesis of 1-(6-chloro-7-methyl-indan-1-yl)-3-(2-fluoro-ethyl)-urea

The title compound was generated from commercially available 3-chloro-2-methylbenzoic acid according to the general procedure E described above. The intermediates 6-chloro-7-methyl-1-indanone and 6-chloro-7-methyl-indan-1-ylamine were isolated and characterized.

6-Chloro-7-methyl-1-indanone: Sulfuric acid was used in the key cyclization step. Spectroscopic data: ¹H NMR (300 MHz, CDCl₃) δ 2.67-2.75 (m, 5H), 3.01-3.09 (m, 2H), 7.2 (d, 1H, J=7.9 Hz), 7.5 (d, 1H, J=7.6 Hz).

6-Chloro-7-methyl-indan-1-ylamine: 6-Chloro-7-methyl-1-indanone (2.50 g, 14.00 mmol), NaBH₃CN (6.00 g, 95.48 mmol) and NH₄OAc (32.04 g, 0.42 mol) in isopropanol were reacted according to the protocols as outlined in general procedure C to give the title indanamine. Spectroscopic data: ¹H NMR (300 MHz, CDCl₃) δ 1.5 (br s, 2H), 1.84-1.93 (m, 1H), 2.30-2.45 (m, 4H), 2.72-2.88 (m, 1H), 3.02-3.16 (m, 1H), 4.40-4.50 (m, 1H), 7.0 (d, 1H, J=7.9 Hz), 7.2 (d, 1H, J=8.2 Hz).

1-(6-Chloro-7-methyl-indan-1-yl)-3-(2-fluoro-ethyl)-urea: The title urea was obtained from 6-chloro-7-methyl-indan-1-ylamine (2.51 g, 13.86 mmol), diimidazole carbonyl (2.25 g, 13.87 mmol), fluoroethyl amine hydrochloride (1.40 g, 90% purity, 12.66 mmol) and diisopropylethyl amine (4.83 mL, 27.73 mmol) according to the protocols as outlined in general procedure A above. Spectroscopic data: ¹H NMR (300 MHz, DMSO-d₆) δ 1.78-1.88 (m, 1H), 2.2 (s, 3H), 2.26-2.35 (m, 1H), 2.68-2.79 (m, 1H), 2.90-3.02 (m, 1H), 3.25-3.39 (m, 2H), 4.3 (t, 1H, J=5.9 Hz), 4.5 (t, 1H, J=5.3 Hz), 5.17-5.24 (m, 1H), 5.9 (t, 1H, J=5.6 Hz), 6.4 (d, 1H, J=8.5 Hz), 7.1 (d, 1H, J=7.9 Hz), 7.3 (d, 1H, J=8.2 Hz).

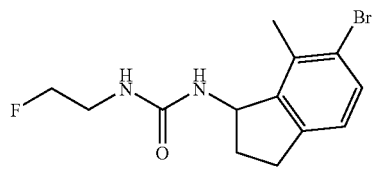

Synthesis of 1-(6-bromo-7-methyl-indan-1-yl)-3-(2-fluoro-ethyl)-urea

The title compound was generated from commercially available 3-bromo-2-methylbenzoic acid according to the general procedure E described above. The intermediates 6-bromo-7-methyl-1-indanone and 6-bromo-7-methyl-indan-1-ylamine were isolated and characterized.

6-Bromo-7-methyl-1-indanone: 2.45 g (22%) of the title indanone was obtained from 3-bromo-2-methyl-benzoic acid (10.40 g, 48.40 mmol), SOCl₂ (5.30 mL, 72.66 mmol) and AlCl₃ (6.50 g, 48.75 mmol) according to the protocols as outlined in general procedure E above. Spectroscopic data: ¹H NMR (300 MHz, CDCl₃) δ 2.67-2.72 (m, 2H), 2.7 (s, 3H), 3.0 (t, 2H, J=6.4, 5.6 Hz), 7.2 (d, 1H, J=7.9 Hz), 7.7 (d, 1H, J=8.2 Hz).

6-Bromo-7-methyl-indan-1-ylamine: 300 mg of the crude title amine (used directly in the next step without further purification) was obtained from 6-bromo-7-methyl-1-indanone (2.45 g, 11.00 mmol), NaBH₃CN (4.80 g, 76.38 mmol) and NH₄OAc (25.00 g, 0.32 mol) according to the protocols as outlined in general procedure E above. Spectroscopic data: ¹H NMR (300 MHz, CDCl₃) δ 1.4 (br s, 2H), 1.84-1.93 (m, 1H), 2.27-2.41 (m, 1H), 2.5 (s, 3H), 2.71-2.85 (m, 1H), 3.02-3.15 (m, 1H), 4.43-4.52 (m, 1H), 6.9 (d, 1H, J=7.9 Hz), 7.4 (d, 1H, J=7.9 Hz).

1-(6-Bromo-7-methyl-indan-1-yl)-3-(2-fluoro-ethyl)-urea: The title urea was obtained from 6-bromo-7-methyl-indan-1-ylamine (300 mg, crude, taken from the previous step, 1.33 mmol), diimidazole carbonyl (215 mg, 1.33 mmol), fluoroethyl amine hydrochloride (132 mg, 90% purity, 1.19 mmol) and diisopropyl ethyl amine (463 μL, 2.66 mmol) according to the protocols as outlined in general procedure A above. Spectroscopic data: ¹H NMR (300 MHz, DMSO-d₆) δ 1.78-1.88 (m, 1H), 2.23-2.34 (m, 4H), 2.67-2.78 (m, 1H), 2.88-3.00 (m, 1H), 3.25-3.39 (m, 2H), 4.3 (t, 1H, J=4.7 Hz), 4.5 (t, 1H, J=5.3 Hz), 5.17-5.25 (m, 1H), 5.9 (t, 1H, J=5.6 Hz), 6.3 (d, 1H, J=8.2 Hz), 7.0 (d, 1H, J=7.9 Hz), 7.4 (d, 1H, J=7.9 Hz). ¹³C NMR (75 MHz, DMSO-d₆) δ 19.0, 30.4, 34.5, 40.5 (d, J=20.25 Hz), 54.7, 84.0 (d, J=164.1 Hz), 123.0, 124.5, 132.2, 134.7, 144.1, 145.4, 157.8.

General Procedure F for the Synthesis of Fluoroethyl Substituted Indan Ureas

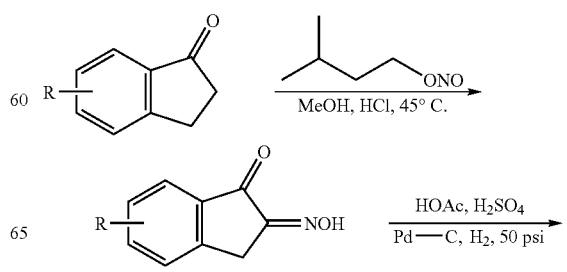

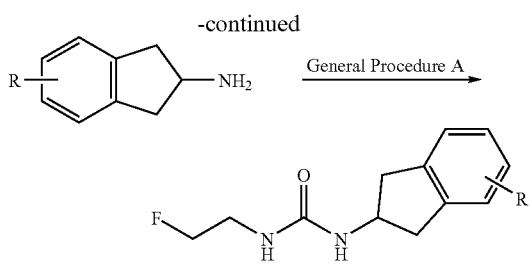

Isoamyl nitrite (1.1 eq) was added to a solution of a substituted indanone in MeOH at 45° C., followed by 2 mL of concentrated HCl. The resulting mixture was stirred for 1 hour, then was cooled to room temperature. The precipitate formed was filtered, washed with small amount of MeOH, then Et$_2$O and dried under vacuum to give the desired oxime.[xxii,xxiii]. The crude oxime was dissolved in HOAc and H$_2$SO$_4$ was added slowly. The resulting mixture was purged with N$_2$ and Pd/C (10%) was added. The reaction mixture was hydrogenated at 50 psi overnight. The catalyst was filtered through celite and the filtrate was concentrated. The concentrate was basified slowly using solid NaOH. The resulting solution was extracted with CH$_2$Cl$_2$ (3×75 mL) and the combined organic extracts were washed with H$_2$O (2×25 mL), brine (1×25 mL), dried over K$_2$CO$_3$ and concentrated to give the desired indan-2-ylamine. This indan-2-ylamine was converted to the title urea using the chemistry described in general procedure A above. This method may be adapted to other cycloalkyl-aryl fused rings systems using starting materials such as those shown below.

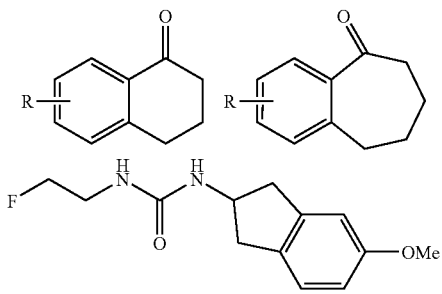

Synthesis of 1-(2-fluoro-ethyl)-3-(5-methoxy-indan-2-yl)-urea

The title compound was generated from commercially available 5-methoxy-1-indanone according to the general procedure F described above. The intermediates 5-methoxy-indan-1,2-dione 2-oxime and 5-methoxy-indan-2-ylamine were isolated and characterized.

5-Methoxy-indan-1,2-dione 2-oxime[24]: The title oxime was obtained from isoamyl nitrite (2.70 mL, 20.09 mmol) and 5-methoxy-1-indanone (3.00 g, 18.50 mmol) according to general procedure F described above. Spectroscopic data: $^1$H NMR (300 MHz, DMSO-d$_6$) δ 3.7 (s, 2H), 3.9 (s, 3H), 6.99-7.04 (m, 1H), 7.1 (s, 1H), 7.7 (d, 1H, J=8.5 Hz), 12.5 (s, 1H).

5-Methoxy-indan-2-ylamine[15]: The title compound was obtained from the crude oxime (2.00 g, 10.50 mmol) according to the general procedure F described above. Spectroscopic data: $^1$H NMR (300 MHz, DMSO-d$_6$) δ 2.43-2.57 (m, 2H), 2.89-3.05 (m, 2H), 3.59-3.69 (m, 1H), 3.7 (s, 3H), 6.7 (dd, 1H, J=8.2 Hz), 6.8 (s, 1H), 7.1 (d, 1H, J=7.9 Hz).

1-(2-Fluoro-ethyl)-3-(5-methoxy-indan-2-yl)-urea: The title compound was obtained from 5-methoxy-indan-2-ylamine (1.19 g, 7.30 mmol), diimidazole carbonyl (1.31 g, 8.07 mmol), fluoroethyl amine hydrochloride (800 mg, 90% purity, 7.24 mmol) and diisopropylethyl amine (2.80 mL, 16.08 mmol) according to general procedure A above. Spectroscopic data: $^1$H NMR (500 MHz, DMSO-d6) □ 2.55-2.70 (m, 2H), 3.02-3.11 (m, 2H), 3.24-3.28 (m, 1H), 3.30-3.36 (m, 1H), 3.7 (s, 3H), 4.3 (t, 2H J=5.1 Hz), 4.4 (t, 1H, J=5.1 Hz), 6.0 (t, 1H, J=5.9 Hz), 6.3 (d, 1H, J=7.3 Hz), 6.7 (d, 1H, J=5.1 Hz), 6.8 (s, 1H), 7.1 (d, 1H, J=8.3 Hz).

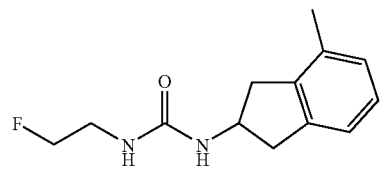

Synthesis of 1-(2-fluoro-ethyl)-3-(4-methyl-indan-2-yl)-urea

The title compound was generated from commercially available 4-methyl-1-indanone according to the general procedure F described above. The intermediates 4-methyl-indan-1,2-dione 2-oxime and 4-methyl-indan-2-ylamine were isolated and characterized.

14-Methyl-indan-1,2-dione 2-oxime[xxiv]: the title compound was obtained from isoamyl nitrite (2.70 mL, 20.09 mmol), 4-methyl-1-indanone (2.65 g, 18.10 mmol) and 1.5 mL of concentrated HCl in MeOH according to the protocols as outlined in general procedure F above. Spectroscopic data: $^1$H NMR (300 MHz, DMSO-d$_6$) δ 2.3 (s, 3H), 3.7 (s, 2H), 7.4 (t, 1H, J=7.6 Hz), 7.50-7.61 (m, 2H), 12.6 (s, 1H).

4-Methyl-indan-2-ylamine[xxv]: The title amine was obtained from 4-methyl-indan-1,2-dione 2-oxime (2.00 g, 11.40 mmol) according to general procedure F described above. Spectroscopic data: $^1$H NMR (300 MHz, DMSO-d$_6$) δ 2.2 (s, 3H), 2.39-2.70 (m, 2H), 2.92-3.06 (m, 2H), 3.63-3.72 (m, 1H), 6.89-7.03 (m, 3H).

1-(2-Fluoro-ethyl)-3-(4-methyl-indan-2-yl)-urea: The title compound was obtained from 4-methyl-indan-2-ylamine (1.44 g, 9.78 mmol), diimidazole carbonyl (1.60 g, 9.86 mmol), fluoroethyl amine hydrochloride (975 mg, 90% purity, 8.82 mmol) and diisopropylethyl amine (3.40 mL, 19.52 mmol) according to general procedure A above. Spectroscopic data: $^1$H NMR (500 MHz, DMSO-d$_6$) δ 2.2 (s, 3H), 2.56-2.62 (m, 1H), 2.65-2.72 (m, 1H), 3.05-3.15 (m, 2H), 3.25-3.34 (m, 2H), 4.29-4.36 (m, 2H), 4.4 (t, 1H, J=5.4 Hz), 6.0 (t, 1H, J=5.9 Hz), 6.3 (d, 1H, J=7.3 Hz), 6.93-6.97 (m, 1H), 7.01-7.05 (m, 2H).

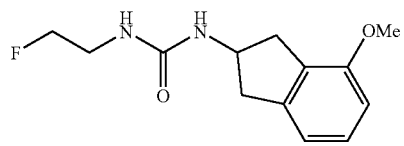

Synthesis of 1-(2-fluoro-ethyl)-3-(4-methoxy-indan-2-yl)-urea

The title compound was generated from commercially available 4-methoxy-1-indanone according to the general procedure F described above. The intermediates 4-methoxyindan-1,2-dione 2-oxime and 4-methoxy-indan-2-ylamine were isolated and characterized.

4-Methoxy-indan-1,2-dione 2-oxime[24]. The title compound was obtained from isoamyl nitrite (4.60 mL, 34.23 mmol), 4-methoxy-1-indanone (5.00 g, 31.00 mmol) and 3.0 mL of concentrated HCl in MeOH according to the protocols as outlined in general procedure F. Spectroscopic data: $^1$H NMR (300 MHz, DMSO-d$_6$) δ 3.6 (s, 2H), 3.9 (s, 3H), 7.30-7.36 (m, 2H), 7.5 (t, 1H, J=8.2 Hz), 12.6 (s, 1H).

4-Methoxy-indan-2-ylamine[24]: The title amine was obtained from 4-methoxy-indan-1,2-dione 2-oxime (3.12 g, 16.30 mmol) according to general procedure F. Spectroscopic data: $^1$H NMR (300 MHz, CDCl$_3$) δ 1.6 (br s, 2H), 2.58-2.72 (m, 2H), 3.10-3.23 (m, 2H), 3.79-3.87 (m, 4H), 6.7 (d, 1H, J=7.9 Hz), 6.8 (d, 1H, J=7.3 Hz), 7.2 (t, 1H, J=7.6 Hz).

1-(2-Fluoro-ethyl)-3-(4-methoxy-indan-2-yl)-urea: The title compound was obtained from 4-methoxy-indan-2-ylamine (1.60 g, 9.80 mmol), diimidazole carbonyl (1.60 g, 9.86 mmol), fluoroethyl amine hydrochloride (980 mg, 90% purity, 8.86 mmol) and diisopropylethyl amine (3.40 mL, 19.52 mmol) according to general procedure A above. Spectroscopic data: $^1$H NMR (500 MHz, DMSO-d$_6$) δ 2.56-2.62 (m, 1H), 2.65-2.70 (m, 1H), 3.01-3.06 (m, 1H), 3.09-3.17 (m, 1H), 3.24-3.28 (m, 1H), 3.30-3.34 (m, 1H), 3.8 (s, 3H), 4.29-4.35 (m, 2H), 4.4 (t, 1H, J=4.9 Hz), 5.9 (t, 1H, J=5.9 Hz), 6.3 (d, 1H, J=6.8 Hz), 6.7 (d, 1H, J=8.3 Hz), 6.8 (d, 1H, J=7.3 Hz), 7.1 (t, 1H, J=7.8 Hz).

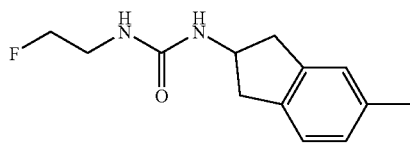

Synthesis of 1-(2-fluoro-ethyl)-3-(5-methyl-indan-2-yl)-urea

The title compound was generated from commercially available 6-methyl-1-indanone according to the general procedure F described above. The intermediates 6-methyl-indan-1,2-dione 2-oxime and 5-methyl-indan-2-ylamine were isolated and characterized.

6-Methyl-indan-1,2-dione 2-oxime[xxvi]: The title compound was obtained from isoamyl nitrite (5.00 mL, 37.20 mmol), 6-methyl-1-indanone (5.00 g, 34.0 mmol) and 3.0 mL of concentrated HCl in MeOH according to general procedure F.

5-Methyl-indan-2-ylamine[26]: The title amine was obtained from 6-methyl-indan-1,2-dione 2-oxime (3.83 g, 22.00 mmol) according to general procedure F. Spectroscopic data: $^1$H NMR (300 MHz, CDCl$_3$) δ 1.7 (s, 2H), 2.3 (s, 3H), 2.52-2.68 (m, 2H), 3.06-3.20 (m, 2H), 3.76-3.85 (m, 1H), 7.0 (d, 1H, J=7.6 Hz), 7.01-7.13 (m, 2H).

1-(2-Fluoro-ethyl)-3-(5-methyl-indan-2-yl)-urea: The title urea was obtained from 5-methyl-indan-2-ylamine (1.90 g, 12.90 mmol), diimidazole carbonyl (2.00 g, 12.33 mmol), fluoroethyl amine hydrochloride (1.30 g, 90% purity, 11.76 mmol) and diisopropylethyl amine (4.50 mL, 26.45 mmol) according to general procedure A above. Spectroscopic data: $^1$H NMR (500 MHz, DMSO-d$_6$) δ 2.3 (s, 3H), 2.59-2.66 (m, 2H), 3.04-3.10 (m, 2H), 3.24-3.33 (m, 2H), 4.28-4.34 (m, 2H), 4.4 (t, 1H, J=4.9 Hz), 6.0 (t, 1H, J=5.4 Hz), 6.3 (d, 1H, J=7.3 Hz), 6.9 (d, 1H, J=7.8 Hz), 7.0 (s, 1H), 7.1 (d, 1H, J=7.8 Hz).

General Procedure G for the Synthesis of Flouoroethyl Substituted Indan-2-yl Ureas

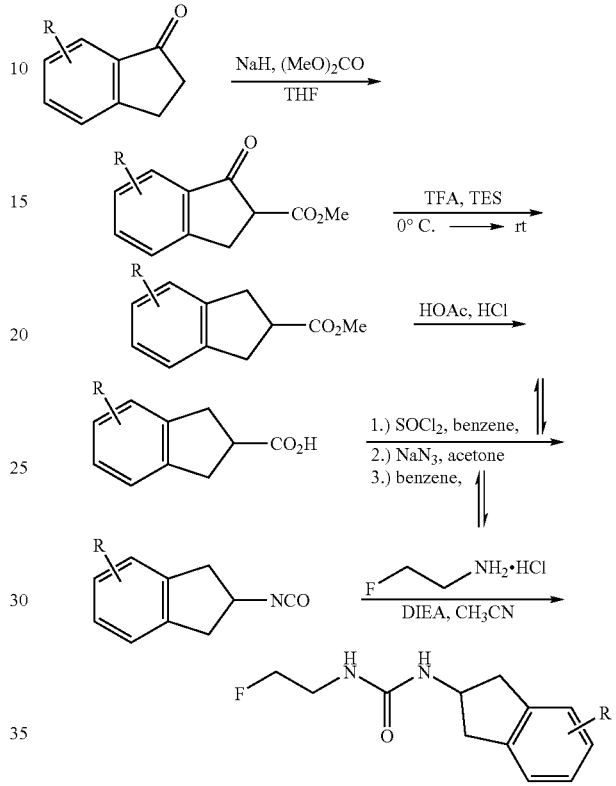

Dimethyl carbonate (1.5 eq) was added to a stirred solution of a substituted indanone (50.00 mmol) in THF, followed by NaH (2.0 eq) and the resulting mixture was refluxed for 30 minutes. After cooling to room temperature, the reaction mixture was quenched with 20% HCl and extracted with EtOAc (3×150 mL). The combined organic phases were washed with H$_2$O (3×100 mL) and brine (1×50 mL), then dried over MgSO$_4$ and concentrated. Purification by column chromatography using hexane:EtOAc (4:1) as eluant gave the desired keto methyl ester. This keto methyl ester (40.40 mmol) was then dissolved in TFA at 0° C., triethylsilane (6.0 eq) was added and the resulting mixture was stirred for 14 hours. The reaction mixture was then concentrated, and the residue was diluted with Et$_2$O and washed with H$_2$O (5×100 mL), saturated NaHCO$_3$ (3×50 mL) and brine (1×75 mL), then dried over MgSO$_4$ and concentrated. Purification by column chromatography using hexane:EtOAc (4:1) as eluant gave the desired methyl ester. A solution of this methyl ester in HOAc containing 20% HCl was stirred at room temperature for 14 hours, then concentrated. The residue was dissolved in 1N NaOH. The resulting mixture was washed with Et$_2$O (3×75 mL), then was acidified slowly using HCl. The aqueous solution was extracted with CH$_2$Cl$_2$ (3×150 mL) and the combined organic extracts was washed with H$_2$O (3×100 mL) and brine (1×75 mL), then dried over MgSO$_4$ and concentrated to give the desired indan carboxylic acid. This indan carboxylic acid (12.00 mmol) and SOCl$_2$ (1.5 eq) were then mixed in benzene and refluxed until no more gas evolution was observed. The solvent was evaporated and the residue was dissolved in acetone, cooled to 0° C. NaN₃ (1.2 eq) dissolved in minimum H₂O was added. The reaction mixture was stirred for 1 hour, then solvent was evaporated and the residue was dissolved in benzene and washed with H₂O (3×15 mL) and brine (1×15 mL), then dried over MgSO₄ and concentrated. The residue was dissolved in benzene and refluxed for 30 minutes. Evaporation of the solvent gave the crude isocyanate, which was mixed with fluoroethyl amine hydrochloride in the presence of diisopropylethyl amine and stirred for 14 hours. After evaporation of the solvent, the concentrate was diluted with EtOAc and washed with H₂O (5×30 mL). The pure product was obtained after recrystallization in CH₃CN. This method may be adapted to other cycloalkyl-aryl fused rings systems using starting materials such as those shown below.

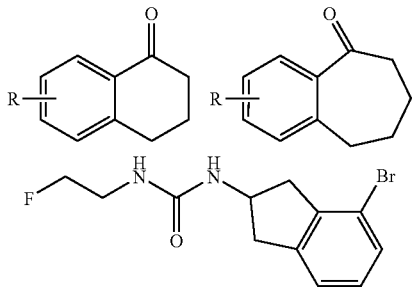

Synthesis of 1-(4-bromo-indan-2-yl)-3-(2-fluoro-ethyl)-urea

Starting material 4-bromo-1-indanone was produced from commercially available 3-(2-bromo-phenyl)-propionic acid using the chemistry described in the first part of the general procedure D. The title compound was thus generated from this indanone according to the protocol described in general procedure G above. The intermediates 4-bromo-1-oxo-indan-2-carboxylic acid methyl ester, 4-bromo-indan-2-carboxylic acid methyl ester, 4-bromo-indan-2-carboxylic acid, and 4-bromo-2-isocyanato-indan were isolated and characterized.

4-Bromo-1-oxo-indan-2-carboxylic acid methyl ester: The title keto ester was obtained from 4-bromo-1-indanone (10.50 g, 50.00 mmol), dimethyl carbonate (6.30 mL, 74.76 mmol) and NaH (4.00 g, 60% dispersion in mineral oil, 100.00 mmol) according to general procedure G described above. Spectroscopic data: ¹H NMR (300 MHz, CDCl₃) δ 3.28-3.39 (m, 1H), 3.45-3.56 (m, 1H), 3.73-3.80 (m, 1H), 3.80-3.84 (m, 3H), 7.3 (d, 1H, J=6.2 Hz), 7.52-7.63 (m, 1H), 7.8 (d, 1H, J=7.6 Hz).

4-Bromo-indan-2-carboxylic acid methyl ester: The title compound was obtained from 4-bromo-1-oxo-indan-2-carboxylic acid methyl ester (10.90 g, 40.40 mmol), TFA and triethylsilane (39.00 mL, 0.24 mol) according to general procedure G. Spectroscopic data: ¹H NMR (300 MHz, CDCl₃) δ 3.24-3.39 (m, 5H), 3.7 (s, 3H), 7.0 (t, 1H, J=7.3 Hz), 7.1 (d, 1H, J=7.3 Hz), 7.3 (d, 1H, J=7.6 Hz).

4-Bromo-indan-2-carboxylic acid: The title acid was obtained from the acidic hydrolysis of 4-bromo-indan-2-carboxylic acid methyl ester according to the protocol described in general procedure G above. Spectroscopic data: ¹H NMR (300 MHz, DMSO-d₆) δ 3.03-3.41 (m, 5H), 7.1 (t, 1H, J=7.9, 7.3 Hz), 7.2 (d, 1H, J=7.6 Hz), 7.3 (d, 1H, J=7.9 Hz), 12.4 (br s, 1H).

4-Bromo-2-isocyanato-indan: Title compound was obtained from 4-bromo-indan-2-carboxylic acid (2.87 g, 12.00 mmol), SOCl₂ (1.30 mL, 17.82 mmol) and NaN₃ (930 mg, 14.31 mmol) according to general procedure G. Spectroscopic data: ¹H NMR (300 MHz, CDCl₃) δ 3.00-3.13 (m, 2H), 3.26-3.40 (m, 2H), 4.33-4.42 (m, 1H), 7.1 (t, 1H, J=7.6 Hz), 7.2 (d, 1H, J=7.3 Hz), 7.3 (d, 1H, J=7.9 Hz).

1-(4-Bromo-indan-2-yl)-3-(2-fluoro-ethyl)-urea: The title urea was generated from 4-bromo-2-isocyanato-indan (12.00 mmol), fluoroethyl amine hydrochloride (1.20 g, 90% purity, 10.85 mmol) and diisopropylethyl amine (4.20 mL, 24.11 mmol) according to the protocol described in general procedure G. Spectroscopic data: ¹H NMR (300 MHz, DMSO-d₆) δ 2.64-2.94 (m, 2H), 3.06-3.42 (m, 4H), 4.28-4.40 (m, 2H), 4.5 (t, 1H, J=5.0 Hz), 6.0 (t, 1H, J=5.6 Hz), 6.4 (d, 1H, J=7.0 Hz), 7.1 (t, 1H, J=7.9 Hz), 7.2 (d, 1H, J=7.3 Hz), 7.4 (d, 1H, J=7.9 Hz).

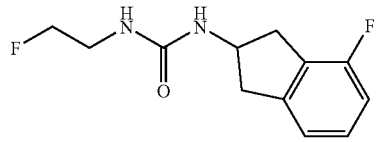

Synthesis of 1-(2-fluoro-ethyl)-3-(4-fluoro-indan-2-yl)-urea

Starting material 4-fluoro-1-indanone was produced from commercially available 3-(2-fluoro-phenyl)-propionic acid using the chemistry described in the first part of the general procedure D. The title compound was thus generated from this indanone according to the protocol described in general procedure G above. The intermediates 4-fluoro-1-oxo-indan-2-carboxylic acid methyl ester, 4-fluoro-indan-2-carboxylic acid methyl ester, 4-fluoro-indan-2-carboxylic acid, and 4-fluoro-2-isocyanato-indan were isolated and characterized.

4-Fluoro-1-oxo-indan-2-carboxylic acid methyl ester: The title compound was obtained from 4-bromo-1-indanone (11.10 g, 74.10 mmol), NaH (6.00 g, 60% dispersion in mineral oil, 150.00 mmol) and dimethyl carbonate (9.40 mL, 0.11 mol) according to the protocols as outlined in general procedure G above. Spectroscopic data: ¹H NMR (300 MHz, CDCl₃) δ 3.35-3.46 (m, 1H), 3.54-3.63 (m, 1H), 3.73-3.80 (m, 1H), 3.8 (s, 3H), 7.06-7.17 (m, 1H), 7.27-7.36 (m, 1H), 7.6 (d, 1H, J=7.3 Hz).

4-Fluoro-indan-2-carboxylic acid methyl ester: The title compound was obtained from 4-fluoro-1-oxo-indan-2-carboxylic acid methyl ester (12.60 g, 60.30 mmol) and triethylsilane (58.00 mL, 0.36 mol) in TFA according to the protocols as outlined in general procedure G. Spectroscopic data: ¹H NMR (300 MHz, CDCl₃) δ 3.17-3.42 (m, 5H), 3.7 (s, 3H), 6.8 (t, 1H, J=8.5 Hz), 7.0 (d, 1H, J=7.6 Hz), 7.09-7.18 (m, 1H).

4-Fluoro-indan-2-carboxylic acid: 4-Fluoro-indan-2-carboxylic acid methyl ester in HOAc containing 20% HCl was hydrolyzed according to the protocols as outlined in general procedure G to afford the desired title acid. Spectroscopic data: ¹H NMR (300 MHz, DMSO-d₆) δ 3.09-3.23 (m, 4H), 3.29-3.40 (m, 1H), 7.0 (t, 1H, J=8.5 Hz), 7.1 (d, 1H, J=7.3 Hz), 7.14-7.24 (m, 1H), 12.4 (br s, 1H).

4-Fluoro-2-isocyanato-indan: The title compound was generated from 4-fluoro-indan-2-carboxylic acid (2.00 g, 11.10 mmol), SOCl₂ (1.20 mL, 16.45 mmol) and NaN₃ (866 mg, 13.32 mmol) according to the protocols as outlined in general procedure G. Spectroscopic data: ¹H NMR (300 MHz, CDCl₃) δ 2.98-3.10 (m, 2H), 3.21-3.35 (m, 2H), 4.35-4.43 (m, 1H), 6.9 (t, 1H, J=8.2 Hz), 7.0 (d, 1H, J=7.6 Hz), 7.09-7.22 (m, 1H).

1-(2-Fluoro-ethyl)-3-(4-fluoro-indan-2-yl)-urea: The title urea was generated from 4-fluoro-2-isocyanato-indan (11.10 mmol), fluoroethyl amine hydrochloride (1.10 g, 90% purity, 9.95 mmol) and diisopropylethyl amine (3.90 mL, 22.39 mmol) according to the protocols as outlined in general procedure G. Spectroscopic data: $^1$H NMR (300 MHz, DMSO-$d_6$) δ 2.67-2.80 (m, 2H), 3.12-3.28 (m, 3H), 3.31-3.37 (m, 1H), 4.23-4.55 (m, 3H), 6.0 (t, 1H, J=6.7 Hz), 6.4 (d, 1H, J=7.0 Hz), 7.0 (t, 1H, J=9.1 Hz), 7.1 (d, 1H, J=7.3 Hz), 7.15-7.24 (m, 1H).

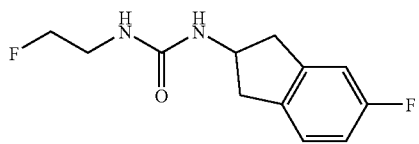

Synthesis of 1-(2-fluoro-ethyl)-3-(5-fluoro-indan-2-yl)-urea

Starting material 6-fluoro-1-indanone was produced from commercially available 3-(4-fluoro-phenyl)-propionic acid using the chemistry described in the first part of the general procedure D. The title compound was thus generated from this indanone according to the protocol described in general procedure G above. The intermediates 6-fluoro-1-oxo-indan-2-carboxylic acid methyl ester, 5-fluoro-indan-2-carboxylic acid methyl ester, 5-fluoro-indan-2-carboxylic acid, and 5-fluoro-2-isocyanato-indan were isolated and characterized.

6-Fluoro-1-oxo-indan-2-carboxylic acid methyl ester: The title compound was obtained from 6-fluoro-1-indanone (8.80 g, 58.60 mmol), NaH (4.70 g, 60% dispersion in mineral oil, 0.12 mol) and dimethyl carbonate (7.42 mL, 88.05 mmol) according to the protocols as outlined in general procedure G. Spectroscopic data: $^1$H NMR (300 MHz, CDCl$_3$) δ 3.29-3.42 (m, 1H), 3.47-3.59 (m, 2H), 3.8 (s, 3H), 7.29-7.53 (m, 3H).

5-Fluoro-indan-2-carboxylic acid methyl ester: The title compound was obtained from 6-fluoro-1-oxo-indan-2-carboxylic acid methyl ester (9.60 g, 46.10 mmol) and triethylsilane (44.00 mL, 0.28 mol) in TFA according to the protocols as outlined in general procedure G. Spectroscopic data: $^1$H NMR (300 MHz, CDCl$_3$) δ 2.76-2.95 (m, 1H), 3.12-3.25 (m, 3H), 3.29-3.40 (m, 1H), 3.7 (s, 3H), 6.77-6.92 (m, 2H), 7.00-7.15 (m, 1H).

5-Fluoro-indan-2-carboxylic acid: 5-fluoro-indan-2-carboxylic acid methyl ester in HOAc containing 20% HCl was hydrolyzed according to the protocols as outlined in general procedure G to give the desired title acid. Spectroscopic data: $^1$H NMR (300 MHz, DMSO-$d_6$) δ 3.02-3.16 (m, 4H), 3.25-3.37 (m, 1H), 6.90-6.98 (m, 1H), 7.01-7.07 (m, 1H), 7.17-7.25 (m, 1H), 12.3 (br s, 1H).

5-Fluoro-2-isocyanato-indan: The title compound was obtained from 5-fluoro-indan-2-carboxylic acid (2.00 g, 11.00 mmol), SOCl$_2$ (1.20 mL, 16.45 mmol) and NaN$_3$ (870 mg, 13.38 mmol) according to the protocols as outlined in general procedure G. Spectroscopic data: $^1$H NMR (300 MHz, CDCl$_3$) δ 2.62-2.85 (m, 1H), 2.89-3.40 (m, 4H), 6.80-6.95 (m, 2H), 7.07-7.19 (m, 1H).

1-(2-Fluoro-ethyl)-3-(5-fluoro-indan-2-yl)-urea: The title urea was obtained from 5-fluoro-2-isocyanato-indan (11.10 mmol), fluoroethyl amine hydrochloride (1.10 g, 90% purity, 9.95 mmol) and diisopropylethyl amine (3.90 mL, 22.39 mmol) according to the protocols as outlined in general procedure G. Spectroscopic data: $^1$H NMR (300 MHz, DMSO-$d_6$) δ 2.61-2.74 (m, 2H), 3.04-3.18 (m, 2H), 3.22-3.37 (m, 2H), 4.28-4.40 (m, 2H), 4.5 (t, 1H, J=5.6 Hz), 6.0 (t, 1H, J=5.6 Hz), 6.3 (d, 1H, J=7.0 Hz), 6.90-6.98 (m, 1H), 7.02-7.07 (m, 1H), 7.17-7.26 (m, 1H). $^{13}$C NMR (75 MHz, DMSO-$d_6$) δ 39.6, 40.4 (d, J=19.5 Hz), 40.6 (d, J=2.25 Hz), 52.0, 84.0 (d, J=164.1 Hz), 112.2 (d, J=21.8 Hz), 113.6 (d, J=21.8 Hz), 126.4 (d, J=8.0 Hz), 137.9 (d, J=2.3 Hz), 144.6, (d, J=9.2 Hz) 158.2, 162.1 (d, J=239.8 Hz).

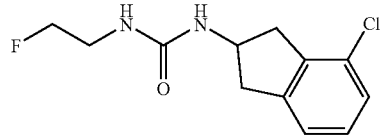

Synthesis of 1-(4-Chloro-indan-2-yl)-3-(2-fluoro-ethyl)-urea

Starting material 4-chloro-1-indanone was produced from commercially available 3-(2-chloro-phenyl)-propionic acid using the chemistry described in the first part of the general procedure D. The title compound was thus generated from this indanone according to the protocol described in general procedure G above. Intermediates 4-chloro-indan-2-carboxylic acid, and 4-chloro-2-isocyanato-indan were isolated and characterized.

4-Chloro-indan-2-carboxylic acid: The title compound was obtained from the hydrolysis of 4-chloro-indan-2-carboxylic acid methyl ester in HOAc containing 20% HCl according to the protocols as outlined in general procedure G. Spectroscopic data: $^1$H NMR (300 MHz, DMSO-$d_6$) δ 3.13-3.25 (m, 4H), 3.29-3.37 (m, 1H), 7.15-7.23 (m, 2H), 7.26-7.33 (m, 1H), 12.4 (br s, 1H).

4-Chloro-2-isocyanato-indan: The title compound was obtained from 4-chloro-indan-2-carboxylic acid (1.30 g, 6.60 mmol), SOCl$_2$ (723 μL, 9.91 mmol) and NaN$_3$ (516 mg, 7.94 mmol) according to the protocols as outlined in general procedure G.

1-(4-Chloro-indan-2-yl)-3-(2-fluoro-ethyl)-urea: The title compound was obtained from 4-chloro-2-isocyanato-indan (6.60 mmol), fluoroethyl amine hydrochloride (660 mg, 90% purity, 5.97 mmol) and diisopropylethyl amine (2.30 mL, 13.20 mmol) according to the protocols as outlined in general procedure G. Spectroscopic data: $^1$H NMR (300 MHz, DMSO-$d_6$) δ 2.70-2.84 (m, 2H), 3.14-3.28 (m, 3H), 3.31-3.37 (m, 1H), 4.28-4.40 (m, 2H), 4.5 (t, 1H, J=5.0 Hz), 6.0 (t, 1H, J=5.9 Hz), 6.3 (d, 1H, J=7.0 Hz), 7.14-7.24 (m, 3H). $^{13}$C NMR (75 MHz, DMSO-$d_6$) δ 39.8, 40.4 (d, J=21 Hz), 41.2, 50.7, 84.0 (d, J=164.1 Hz), 124.0, 126.9, 129.1, 130.4, 140.2, 144.7, 158.2.

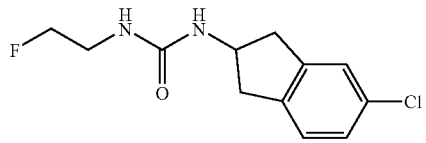

Synthesis of 1-(5-chloro-indan-2-yl)-3-(2-fluoro-ethyl)-urea

The title compound was generated from the commercially available 5-chloro-1-indanone according to the protocol described in general procedure G above. Intermediates 5-chloro-1-oxo-indan-2-carboxylic acid methyl ester, 5-chloro-indan-2-carboxylic acid methyl ester, 5-chloro-indan-2-carboxylic acid and 5-chloro-2-isocyanato-indan were isolated and characterized.

5-Chloro-1-oxo-indan-2-carboxylic acid methyl ester[xxvii]: 4.93 g (74%) of the title compound was obtained from 5-chloro-1-indanone (5.00 g, 30.00 mmol), dimethyl carbonate (3.70 mL, 43.91 mmol) and NaH (2.42 g, 60% dispersion in mineral oil, 60.50 mmol) according to the protocols as outlined in general procedure G. Spectroscopic data: $^1$H NMR (300 MHz, CDCl$_3$) δ 3.30-3.41 (m, 1H), 3.48-3.56 (m, 1H), 3.7 (dd, 1H, J=8.2 Hz), 3.8 (s, 3H), 7.35-7.41 (m, 1H), 7.48-7.53 (m, 1H), 7.7 (d, 1H, J=8.2 Hz).

5-Chloro-indan-2-carboxylic acid methyl ester: 4.52 g (96%) of the title compound was obtained from 5-chloro-1-oxo-indan-2-carboxylic acid methyl ester (4.93 g, 22.00 mmol) and triethylsilane (21.00 mL, 0.13 mol) according to the protocols as outlined in general procedure G. Spectroscopic data: $^1$H NMR (300 MHz, CDCl$_3$) δ 3.06-3.44 (m, 5H), 3.7 (s, 3H), 7.1 (br s, 2H), 7.2 (br s, 1H).

5-Chloro-indan-2-carboxylic acid: The title compound was obtained from the hydrolysis of 5-chloro-indan-2-carboxylic acid methyl ester (4.42 g, 21.00 mmol) in HOAc containing 20% HCl according to the protocols as outlined in general procedure G. Spectroscopic data: $^1$H NMR (300 MHz, CDCl$_3$) δ 3.16-3.29 (m, 4H), 3.32-3.43 (m, 1H), 7.08-7.16 (m, 2H), 7.2 (br s, 1H).

5-Chloro-2-isocyanato-indan: The crude title compound was obtained from SOCl$_2$ (1.40 mL, 19.19 mmol), NaN$_3$ (992 mg, 15.26 mmol) according to the protocols as outlined in general procedure G. This crude 5-chloro-2-isocyanato-indan was used in the next step without further purification.

1-(5-Chloro-indan-2-yl)-3-(2-fluoro-ethyl)-urea: The title urea was obtained from 5-chloro-2-isocyanato-indan (12.7 mmol, crude) and fluoroethyl amine hydrochloride (1.30 g, 90% purity, 11.75 mmol) according to the protocols as outlined in general procedure G described above. Spectroscopic data: $^1$H NMR (300 MHz, DMSO-d$_6$) δ 2.63-2.75 (m, 2H), 3.06-3.18 (m, 2H), 3.22-3.37 (m, 2H), 4.28-4.40 (m, 2H), 4.5 (t, 1H, J=5.0 Hz), 6.0 (t, 1H, J=5.9 Hz), 6.3 (d, 1H, J=7.0 Hz), 7.16 (d, 1H, J=7.92 Hz), 7.23 (d, 1H, J=7.62 Hz), 7.28 (s, 1H). $^{13}$C NMR (75 MHz, DMSO-d$_6$) δ 39.9, 40.4 (d, J=21 Hz), 40.41, 51.8, 84.0 (d, J=164.0 Hz), 125.2, 126.7, 126.9, 131.5, 141.1, 144.7, 158.2.

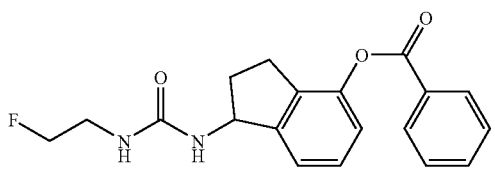

Synthesis of 1-({[(2-fluoroethyl)amino]carbonyl}amino)-2,3-dihydro-1H-inden-4-yl benzoate The title compound was generated from commercially available benzoic acid 1-oxo-indan-4-yl ester according to general procedure C described above. The intermediate benzoic acid 1-amino-indan-4-yl ester was isolated and characterized.

Benzoic acid 1-amino-indan-4-yl ester[xxviii]: The title amine was obtained from benzoic acid 1-oxo-indan-4-yl ester (5.0 g, 19.82 mmol), NaBH$_3$CN (13.00 g, 0.21 mol) and NH$_4$OAc (50.00 g, 0.65 mol) in isopropanol according to general procedure C.

1-({[(2-Fluoroethyl)amino]carbonyl}amino)-2,3-dihydro-1H-inden-4-yl benzoate: The title compound was produced from benzoic acid 1-amino-indan-4-yl ester (crude, taken from the previous step), diimidazole carbonyl (1.62 g, 10.00 mmol), fluoroethyl amine hydrochloride (1.00 g, 90% purity, 9.05 mmol) and diisopropylethyl amine (3.00 mL, 17.22 mmol) according to general procedure A above. Spectroscopic data: $^1$H NMR (300 MHz, DMSO-d$_6$) δ ppm 1.62-1.77 (m, 1H) 2.37-2.39 (m, 1H) 2.57-2.69 (m, 1H) 2.73-2.82 (m, 1H) 3.38 (t, J=5.72 Hz, 1H) 4.07 (q, J=5.18 Hz, 1H) 4.33 (t, J=5.13 Hz, 1H) 4.49 (t, J=5.13 Hz, 1H) 5.17 (d, J=8.21 Hz, 1H) 6.00-6.14 (m, 1H) 6.44 (d, J=8.50 Hz, 1H) 7.14 (dd, J=14.95, 7.62 Hz, 2H) 7.29 (t, J=7.62 Hz, 1H) 7.61 (t, J=7.62 Hz, 2H) 7.75 (t, J=7.33 Hz, 1H) 8.13 (d, J=7.92 Hz, 2H).

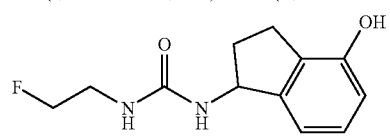

Synthesis of 1-(2-fluoroethyl)-3-(4-hydroxy-2,3-dihydro-1H-inden-1-yl)urea

N-(2-fluoroethyl)-N'-(4-hydroxy-2,3-dihydro-1H-inden-1-yl)urea: 1-({[(2-fluoroethyl)amino]carbonyl} amino)-2,3-dihydro-1H-inden-4-yl benzoate (reported earlier, 230 mg, 0.67 mmol) was dissolved in MeOH (20 mL) and lithium hydroxide (900.00 mg, 37.58 mmol) was added. The resulting reaction mixture was refluxed for 4 hours and then cooled to room temperature. Concentration followed by the addition of HCl (10%, 10.00 mL) gave a precipitate. The solid was then washed with water, ether and then vacuum-dried to afford the desired title compound. Spectroscopic data: $^1$H NMR (300 MHz, DMSO-d$_6$) δ ppm 1.53-1.68 (m, 1H) 2.27-2.41 (m, 1H) 2.47-2.61 (m, 1H) 2.70-2.85 (m, 1H) 3.24-3.39 (m, 2H) 4.31 (t, J=5.13 Hz, 1H) 4.47 (t, J=4.98 Hz, 1H) 4.97-5.10 (m, 1H) 6.03 (t, J=5.57 Hz, 1H) 6.25 (d, J=8.21 Hz, 1H) 6.58-6.72 (m, 2H) 6.97 (t, J=7.77 Hz, 1H) 9.24 (s, 1H).

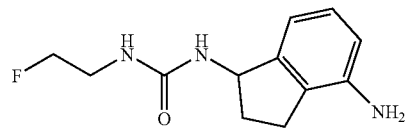

Synthesis of 1-(4-amino-indan-1-yl)-3-(2-fluoro-ethyl)-urea

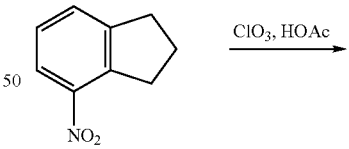

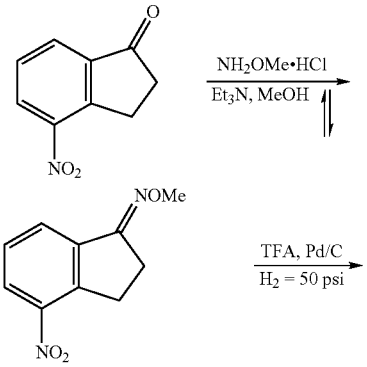

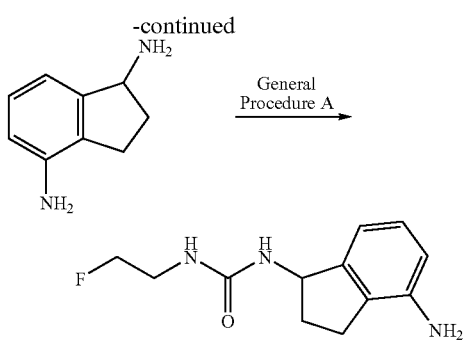

The title compound was generated from commercially available 4-nitroindan according to the chemistry described in the scheme above. The intermediates 4-nitro-indan-1-one, 4-nitro-indan-1-one O-methyl-oxime and indan-1,4-diamine were isolated and characterized.

4-Nitro-indan-1-one[xxix]: A sample of CrO$_3$ (18 g, 180 mmol) in 300 mL of HOAc was added to a solution of 4-nitroindane (10.96 g, 66.42 mmol) in HOAc (200 mL). The resulting solution was stirred for 2 hours after which it was quenched into water. The resulting mixture was extracted with EtOAc (3×200 mL), and the combined organic extracts were washed with H$_2$O (3×200 mL), brine (1×200 mL), dried over MgSO$_4$ and concentrated. Purification by column chromatography using hex:EtOAc (4:1) as eluant afforded 5.96 g (50% yield) of the title compound. Spectroscopic data: $^1$H NMR (300 MHz, CDCl$_3$) δ 2.78-2.85 (m, 2H), 3.63-3.69 (m, 2H), 7.62 (t, J=7.92, 6.74 Hz, 1H), 8.09 (d, J=8.50 Hz, 1H), 8.48 (d, J=7.92 Hz, 1H).

4-Nitro-indan-1-one O-methyl-oxime: To a solution of 4-nitroindane-1-one (4.75 g, 26.81 mmol) in MeOH was added methoxyl amine hydrochloride (4.50 g, 53.88 mmol) and triethyl amine (7.50 mL, 53.81 mmol). After refluxing overnight, the reaction mixture was cooled to room temperature and extracted with EtOAc (3×200 mL). The combined organic extracts were washed with H$_2$O (3×200 mL), brine (1×200 mL), dried over MgSO$_4$ and concentrated. Purification by column chromatography using hex: Et$_2$O (4:1) as eluant afforded 5.31 g (97% yield) of the title compound. Spectroscopic data: $^1$H NMR (300 MHz, CDCl$_3$) δ (1$^{st}$ isomer) 2.92-2.98 (m, 2H), 3.50-3.56 (m, 2H), 4.01 (s, 3H), 7.45 (t, J=7.62 Hz, 1H), 8.00 (d, J=7.33 Hz, 1H), 8.20 (d, J=7.92 Hz, 1H). 2$^{nd}$ isomer: 2.90-2.98 (m, 2H), 3.49-3.58 (m, 2H), 4.02 (s, 3H), 7.45 (t, J=8.21 Hz, 1H), 8.19 (d, J=8.21 Hz, 1H), 8.66 (d, J=7.92 Hz, 1H).

Indan-1,4-diamine: A solution of 4-nitro-indan-1-one O-methyl-oxime (5.31 g, 25.75 mmol) in 50 mL of TFA was mixed with Pd/C (150 mg) and hydrogenated at 50 psi for 14 hours. The resulting mixture was filtered through a pad of celite and the filtrate was concentrated to give the crude title compound, which was used in the next step without further purification. Spectroscopic data: $^1$H NMR (300 MHz, DMSO-d$_6$) δ 1.90-2.03 (m, 1H), 2.41-2.53 (m, 3H), 2.63-3.18 (m, 2H), 4.65-4.75 (m, 1H), 7.00-7.13 (m, 1H), 7.18-7.27 (m, 2H), 8.31 (s, 2H).

1-(4-Amino-indan-1-yl)-3-(2-fluoro-ethyl)-urea: The title urea was obtained from diimidazole carbonyl (4.20 g, 25.89 mmol), fluoroethylamine hydrochloride (2.60 g, 90% purity, 23.52 mmol), diisopropyl ethyl amine (9.0 mL, 51.67 mmol) and indane amine (3.80 g, 25.7 mmol) according to the protocols as outlined in general procedure A described above. Spectroscopic data: $^1$H NMR (500 MHz, DMSO-d$_6$) δ 1.58-1.66 (m, 1H), 2.32-2.40 (m, 1H), 2.44-2.52 (m, 1H), 2.66-2.73 (m, 1H), 3.31 (q, J=5.37 Hz, 1H), 3.37 (q, J=5.86, 4.88 Hz, 1H), 4.36 (t, J=4.88 Hz, 1H), 4.45 (t, J=4.88 Hz, 1H), 4.88 (s, 2H), 5.02 (q, J=7.81 Hz, 1H), 6.05 (t, J=5.37 Hz, 1H), 6.21 (d, J=8.30 Hz, 1H), 6.42-6.48 (m, 2H), 6.89 (t, J=7.81, 6.83 Hz, 1H). $^{13}$C NMR (126 MHz, DMSO-d$_6$) δ 27.28, 34.43, 40.54 (d, J=20.62 Hz), 55.74, 84.13 (d, J=164.46 Hz), 112.15, 113.06, 127.00, 127.91, 145.09, 145.91, 158.44.

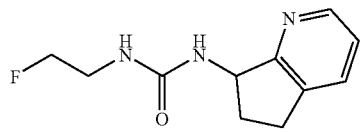

Synthesis of 1-(6,7-dihydro-5H-[1]pyrindin-7-yl)-3-(2-fluoro-ethyl)-urea

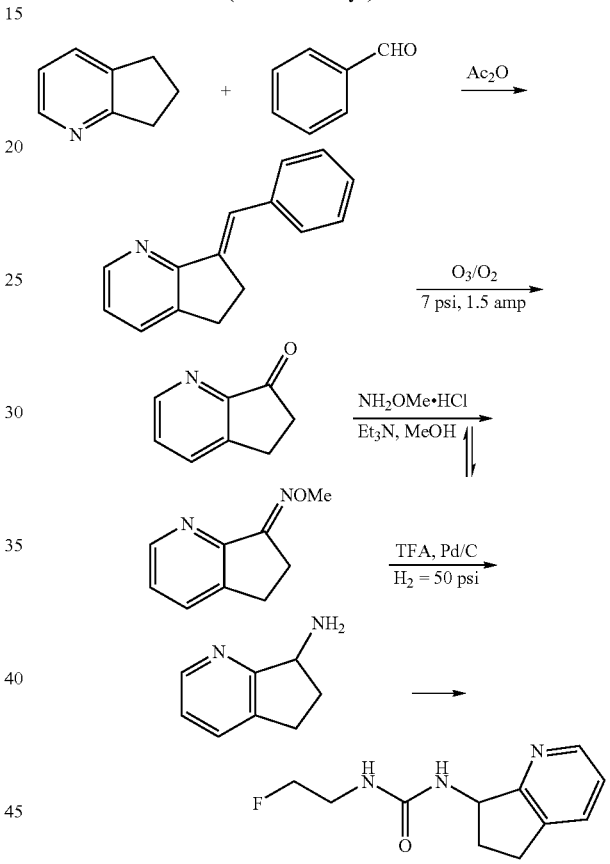

The title compound was generated from commercially available 6,7-dihydro-5H-[1]pyrindine according to the chemistry described in the scheme above. The intermediates 5-benzylidene-6,7-dihydro-5H-[1]pyrindine, 5,6-dihydro-[1]pyrindin-7-one, 4-nitro-indan-1-one, 5,6-dihydro-[1]pyrindin-7-one O-methyl-oxime and 6,7-dihydro-5H-[1]pyrindin-7-ylamine were isolated and characterized.

5-Benzylidene-6,7-dihydro-5H-[1]pyindine[xxx]: A sample of 6,7-dihydro-5H-[1]pyrindine (14.51 g, 0.12 mol), benzaldehyde (13.6 mL, 0.13 mol) and acetic anhydride (22.0 mL, 0.23 mol) was heated at 140° C. overnight. After cooling down to room temperature, the resulting mixture was extracted with CH$_2$Cl$_2$ (3×300 mL). The combined organic extracts were washed with brine (1×200 mL), dried over MgSO$_4$ and concentrated. Purification by column chromatography using hex:Et$_2$O (4:1) as eluant afforded 12.18 g (67.7% yield) of the title compound. Spectroscopic data: $^1$H NMR (300 MHz, CDCl$_3$) δ 3.06-3.21 (m, 4H), 7.06-7.15 (m, 1H), 7.22-7.30 (m, 1H), 7.34-7.43 (m, 2H), 7.51-7.60 (m, 4H), 8.45-8.50 (m, 1H).

5,6-Dihydro-[1]pyrindin-7-one[32]: A solution of 5-benzylidene-6,7-dihydro-5H-[1]pyindine (12.18 g, 58.8 mmol) in 200 mL of MeOH: $CH_2Cl_2$ (1:1) was subjected to ozonolysis at 7 psi and 1.5 amperes. The resulting mixture was quenched with thiourea, filtered and concentrated. Purification by column chromatography using hex:EtOAc (4:1) as eluant afforded 5.96 g (76%) of the title compound. Spectroscopic data: $^1$H NMR (300 MHz, $CDCl_3$) δ 2.75-2.82 (m, 2H), 3.15-3.22 (m, 2H), 7.47 (q, J=4.40, 3.52 Hz, 1H), 7.91 (d, J=8.79 Hz, 1H), 8.79 (d, J=5.28 Hz, 1H).

5,6-Dihydro-[1]pyrindin-7-one O-methyl-oxime: Methoxylamine hydrochloride (6.20 g, 74.23 mmol) was added to a solution of 5,6-dihydro-[1]pyrindin-7-one (4.96 g, 37.25 mmol) in MeOH and triethylamine (10.4 mL, 74.62 mmol) was added. After refluxing overnight, the reaction mixture was cooled to room temperature and extracted with EtOAc (3×200 mL). The combined organic extracts were washed with $H_2O$ (3×200 mL), brine (1×200 mL), dried over $MgSO_4$ and concentrated. Purification by column chromatography using hex: $Et_2O$ (4:1) as the eluant afforded 4.10 g (68% yield) of the title oxime.31 g (96.5% yield) of the title compound. Spectroscopic data: $^1$H NMR (300 MHz, $CDCl_3$) δ 2.90-2.96 (m, 2H), 2.99-3.07 (m, 2H), 4.08 (s, 3H), 7.21 (q, J=4.69, 2.93 Hz, 1H), 7.63 (d, J=7.92 Hz, 1H), 8.55 (d, J=4.69 Hz, 1H).

6,7-Dihydro-5H-[1]pyrindin-7-ylamine: 5,6-Dihydro-[1]pyrindin-7-one O-methyl-oxime (4.1 g, 25.28 mmol) and Pd/C (150 mg) were mixed in TFA and then resulting reaction mixture was hydrogenated under 50 psi for 14 hours. Filtration via celite and concentration afforded the desired title amine. Spectroscopic data: $^1$H NMR (300 MHz, $CDCl_3$) δ 1.89-2.02 (m, 1H), 2.46-2.58 (m, 1H), 2.89-3.01 (m, 2H), 4.62-4.73 (m, 1H), 7.30-7.37 (m, 1H), 7.77 (d, J=7.62 Hz, 1H), 8.35-8.50 (m, 3H).

1-(6,7-Dihydro-5H-[1]pyrindin-7-yl)-3-(2-fluoro-ethyl)-urea: The title compound was obtained from 6,7-dihydro-5H-[1]pyrindin-7-ylamine (25.3 mmole), diimidazole carbonyl (4.00 g, 24.65 mmol), fluoroethyl amine hydrochloride (2.50 g, 90% purity, 22.61 mmol) and diisopropyl ethyl amine (8.80 mL, 50.52 mmol) according to the protocols as outlined in general procedure A. Spectroscopic data: $^1$H NMR (500 MHz, DMSO-$d_6$) δ 1.67-1.75 (m, 1H), 2.46-2.53 (m, 1H), 2.75-2.82 (m, 1H), 2.84-2.91 (m, 1H), 3.28-3.33 (m, 1H), 3.34-3.40 (m, 1H), 4.37 (t, J=4.88 Hz, 1H), 4.46 (t, J=5.37 Hz, 1H), 5.00 (q, J=7.81 Hz, 1H), 6.22 (t, J=5.37 Hz, 1H), 6.35 (d, J=7.32 Hz, 1H), 7.20 (q, J=4.88, 2.44 Hz, 1H), 7.65 (d, J=7.32 Hz, 1H), 8.36 (d, J=4.88 Hz, 1H). $^{13}$C NMR (126 MHz, DMSO-$d_6$) δ 27.77, 33.97, 40.55 (d, J=20.14 Hz), 55.43, 84.08 (d, J=163.97 Hz), 123.01, 133.35, 136.81, 148.26, 158.47, 164.30.

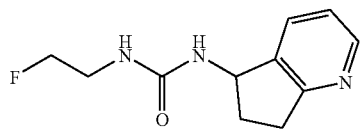

Synthesis of 1-(6,7-dihydro-5H-[1]pyrindin-5-yl)-3-(2-fluoro-ethyl)-urea

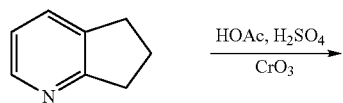

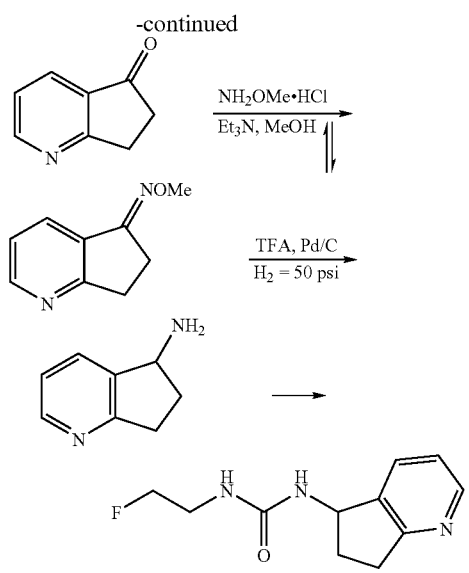

The title compound was generated from commercially available 6,7-dihydro-5H-[1]pyrindine according to the chemistry described in the scheme above. The intermediates 6,7-dihydro-[1]pyrindin-5-one, 6,7-dihydro-[1]pyrindin-5-one O-methyl-oxime and 6,7-dihydro-5H-[1]pyrindin-5-ylamine were isolated and characterized.

6,7-Dihydro-[1]pyrindin-5-one[xxxi]: To a solution of 6,7-dihydro-5H-[1]pyrindine (11.00 g, 92.30 mmol) in 50 mL HOAc and 10 mL $H_2SO_4$ at 0° C. was added $CrO_3$ (18.50 g, 0.19 mol) dissolved in 6 mL $H_2O$ and 30 mL HOAc. The resulting mixture was stirred overnight, cooled on ice and basified with $NH_4OH$ to pH 11. The mixture was extracted with $CHCl_3$ (3×250 mL), and the combined organic extracts were washed with $H_2O$ (3×100 mL), brine (1×200 mL), dried over $MgSO_4$ and concentrated. Purification by column chromatography using hexane:EtOAc (2:3) as the eluant gave 2.29 g (18.6%) of the title compound. Spectroscopic data: $^1$H NMR (300 MHz, $CDCl_3$) δ 2.77-2.83 (m, 2H), 3.27-3.33 (m, 2H), 7.34 (dd, J=7.62 Hz, 1H), 8.03 (dd, J=7.62 Hz, 1H), 8.82 (dd, J=4.69 Hz, 1H).

6,7-Dihydro-[1]pyrindin-5-one O-methyl-oxime: A solution of 6,7-dihydro-[1]pyrindin-5-one (5.34 g, 40.10 mmol), methoxyl amine hydrochloride (6.70 g, 80.22 mmol) and triethyl amine (11.20 mL, 80.36 mmol) in MeOH were reacted according to the protocols as outlined in general procedure H to give 5.43 g (84%) of the title oxime. Spectroscopic data: $^1$H NMR (300 MHz, $CDCl_3$) δ 2.85-2.98 (m, 2H), 3.11-3.23 (m, 2H), 4.00 (s, 3H), 7.13-7.22 (m, 1H), 7.90-7.99 (m, 1H), 8.47-8.59 (m, 1H).

6,7-Dihydro-5H-[1]pyrindin-5-ylamine: A solution of 6,7-dihydro-[1]pyrindin-5-one O-methyl-oxime (5.43 g, 33.5 mmol) and Pd/C (150 mg) in TFA were hydrogenated under 50 psi for 14 hours. Filtration via celite and concentration afforded the title amine. Spectroscopic data: $^1$H NMR (300 MHz, $CDCl_3$) δ 1.66-1.77 (m, 2H), 2.17-2.27 (m, 2H), 2.45-2.50 (m, 1H), 3.24-3.33 (m, 2H), 8.42-8.58 (m, 1H), 8.61-8.72 (m, 1H), 9.37-9.50 (m, 1H).

1-(6,7-Dihydro-5H-[1]pyrindin-5-yl)-3-(2-fluoro-ethyl)-urea: The title compound was obtained from 6,7-dihydro-5H-[1]pyrindin-5-ylamine (33.5 mmol, crude, taken from the previous step without further purification), diimidazole carbonyl (5.40 g, 33.28 mmol), fluoroethyl amine hydrochloride (3.30 g, 90% purity, 29.85 mmol) and diisopropyl ethyl amine (11.70 mL, 67.17 mmol) according to the protocols as outlined in general procedure A. Spectroscopic data: $^1$H NMR (500 MHz, DMSO-d$_6$) δ 1.70-1.78 (m, 1H), 2.40-2.47 (m, 1H), 2.78-2.99 (m, 2H), 3.32 (q, J=6.35, 5.37, 4.39 Hz, 1H), 3.38 (q, J=5.37 Hz, 1H), 4.37 (t, J=5.37 Hz, 1H), 4.47 (t, J=5.37 Hz, 1H), 5.13 (q, J=7.81 Hz, 1H), 6.08 (t, J=5.37 Hz, 1H), 6.44 (d, J=8.30 Hz, 1H), 7.18 (dd, J=7.81 Hz, 1H), 7.58 (d, J=7.32 Hz, 1H), 8.35-8.37 (m, 1H). $^{13}$C NMR (126 MHz, DMSO-d$_6$) δ 32.17, 32.61, 40.57 (d, J=20.62 Hz), 53.39, 84.02 (d, J=164.46 Hz), 122.22, 132.57, 138.67, 149.22, 158.40, 164.31.

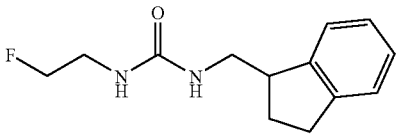

Synthesis of
1-(2-Fluoro-ethyl)-3-indan-1-ylmethyl-urea

The title compound was generated from commercially available indene according to the procedures described below. The intermediates 3H-indene-1-carboxylic acid ethyl ester and indan-1-yl-methylamine were isolated and characterized.

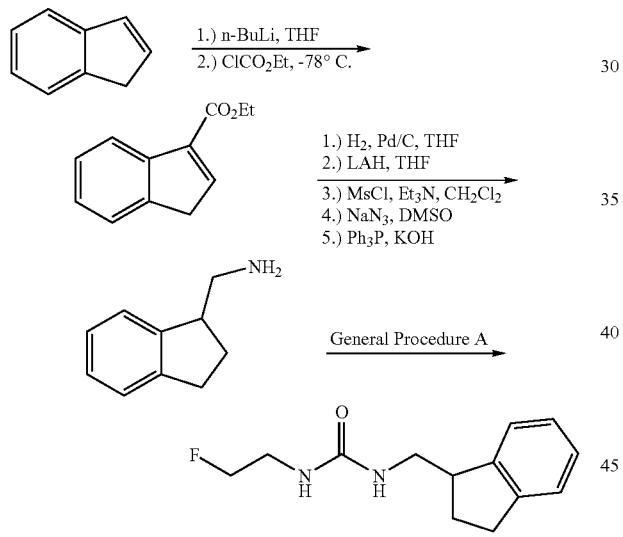

3H-indene-1-carboxylic acid ethyl ester[xxxii]: To a solution of indene (10.00 mL, 76.40 mmol) in THF at −78° C. was added n-BuLi (37.00 mL, 2.5 M in hexane, 92.50 mmol) and the resulting mixture was stirred overnight. Ethyl chloroformate (15.00 mL, 0.16 mol) was then added and the resulting solution was stirred for 5 minutes after which it was quenched with saturated NH$_4$Cl. The resulting mixture was extracted with Et$_2$O (3×300 mL) and the combined organic extracts were washed with H$_2$O (2×200 mL), brine (1×200 mL), dried over MgSO$_4$ and concentrated. Purification by column chromatography using hex:EtOAc (1:1) as eluant afforded 8.00 g (55% yield) of the title compound.

Indan-1-yl-methylamine[xxxiii]: A solution of 3H-indene-1-carboxylic acid ethyl ester (8.00 g, 42.60 mmol) in THF was mixed with Pd/C (800 mg) and hydrogenated at 50 psi for 6 hours. The resulting mixture was filtered through a pad of celite and the filtrate was concentrated. The residue[xxxiv] was dissolved in THF and cooled to 0° C. LAH (43.00 mL, 1.0 M in THF, 43.00 mmol) was added and the reaction mixture was stirred overnight. The resulting solution was quenched with NaOH and extracted with Et$_2$O (3×250 mL). The combined organic extracts were washed with H$_2$O (3×150 mL), brine (1×150 mL), dried over MgSO$_4$ and concentrated to give indan-1-yl-methanol[xxxv]. To a solution of the alcohol in CH$_2$Cl$_2$ was added Et$_3$N (12.00 mL, 86.10 mmol) and MsCl (5.20 mL, 67.18 mmol). The resulting mixture was stirred overnight, after which it was washed with brine (1×150 mL), dried over MgSO$_4$ and concentrated. The residue was dissolved in DMSO and NaN$_3$ (5.50 g, 84.60 mmol) was added. The reaction mixture was stirred at room temperature overnight. The resulting mixture was diluted with water and extracted with Et$_2$O (3×300 mL). The combined organic extracts were washed with H$_2$O (3×150 mL), brine (1×150 mL) dried over MgSO$_4$ and concentrated. The crude azide was dissolved in THF:H$_2$O (3:1) and Ph$_3$P (11.20 g, 42.70 mmol) was added followed by KOH (2.40 g, 42.77 mmol). The reaction mixture was stirred overnight after which it was acidified with concentrated HCl. The resulting solution was washed with Et$_2$O and the aqueous layer was basified with ammonium hydroxide and extracted with Et$_2$O (3×200 mL). The combined organic extracts was washed with H$_2$O (3×100 mL), brine (1×100 mL), dried over MgSO$_4$ and concentrated to give the title amine.

1-(2-Fluoro-ethyl)-3-indan-1-ylmethyl-urea: The title compound was generated from indan-1-yl-methylamine (1.50 g, 10.30 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.68-1.82 (m, 1H), 2.06-2.21 (m, 1H), 2.77-2.91 (m, 2H), 3.07-3.14 (m, 1H), 3.17-3.27 (m, 2H), 3.32-3.41 (m, 2H), 4.3 (t, J=5.0 Hz, 1H), 4.5 (t, J=5.0 Hz, 1H), 6.0 (t, J=5.3 Hz, 1H), 6.2 (t, J=5.3 Hz, 1H), 7.12-7.27 (m, 4H).

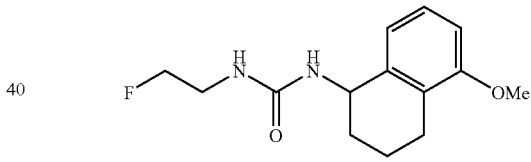

Synthesis of 1-(2-fluoro-ethyl)-3-(5-methoxy-1,2,3,4-tetrahydro-naphthalen-1-yl)-urea The title compound was generated from commercially available 5-methoxy-3,4-dihydro-2H-naphthalen-1-one according to the general procedure C described above. The intermediate 5-methoxy-1,2,3,4-tetrahydro-naphthalen-1-ylamine was isolated and characterized.

5-Methoxy-1,2,3,4-tetrahydro-naphthalen-1-ylamine[xxxvi]: The title amine was obtained from 5-methoxy-3,4-dihydro-2H-naphthalen-1-one (5.00 g, 28.40 mmol), NaBH$_3$CN (12.50 g, 0.20 mmol) and NH$_4$OAc (50.00 g, 0.65 mmol) according to the protocols as outlined in general procedure A above.

1-(2-Fluoro-ethyl)-3-(5-methoxy-1,2,3,4-tetrahydro-naphthalen-1-yl)-urea: The title urea was obtained from 5-methoxy-1,2,3,4-tetrahydro-naphthalen-1-ylamine (1.80 g, 10.10 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ

1.46-1.92 (m, 4H), 2.46-2.62 (m, 2H), 3.26-3.41 (m, 2H), 3.8 (s, 3H,) 4.3 (t, J=5.0 Hz, 1H), 4.5 (t, J=5.0 Hz, 1H), 4.70-4.79 (m, 1H), 6.0 (t, J=5.6 Hz, 1H), 6.3 (d, J=8.8 Hz, 1H), 6.79 (d, J=8.2 Hz, 1H), 6.83 (d, J=7.6 Hz, 1H), 7.1 (t, J=7.9 Hz, 1H).

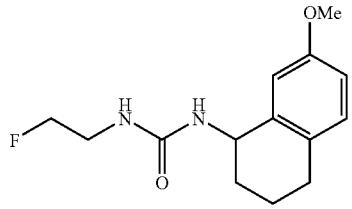

Synthesis of 1-(2-fluoro-ethyl)-3-(7-methoxy-1,2,3,4-tetrahydro-naphthalen-1-yl)-urea The title compound was generated from commercially available 7-methoxy-3,4-dihydro-2H-naphthalen-1-one according to the general procedure C described above. The intermediate 7-methoxy-1,2,3,4-tetrahydro-naphthalen-1-ylamine was isolated and characterized.

7-Methoxy-1,2,3,4-tetrahydro-naphthalen-1-ylamine[xxxvii]: The title amine was obtained from 7-methoxy-3,4-dihydro-2H-naphthalen-1-one (5.00 g, 28.40 mmol), NaBH$_3$CN (12.50 g, 0.20 mol) and NH$_4$OAc (50.00 g, 0.65 mol) according to general procedure C.

1-(2-Fluoro-ethyl)-3-(7-ethoxy-1,2,3,4-tetrahydro-naphthalen-1-yl)-urea: The title compound was produced from 7-methoxy-1,2,3,4-tetrahydro-naphthalen-1-ylamine (1.80 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to general procedure A above. Spectroscopic data: $^1$H NMR (300 MHz, DMSO-d$_6$) δ 1.49-1.92 (m, 4H), 2.6 (s, 2H), 3.27-3.42 (m, 2H), 3.7 (s, 3H), 4.3 (t, J=5.0 Hz, 1H), 4.5 (t, J=5.0 Hz, 1H), 4.67-4.77 (m, 1H), 6.0 (t, J=6.2, 5.6 Hz, 1H), 6.3 (d, J=8.5 Hz, 1H), 6.70-6.79 (m, 2H), 7.0 (d, J=8.2 Hz, 1H).

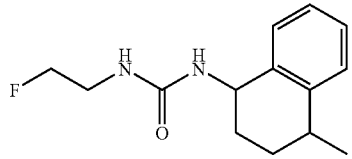

Synthesis of 1-(2-fluoro-ethyl)-3-(4-methyl-1,2,3,4-tetrahydro-naphthalen-1-yl)-urea 4-Methyl-1,2,3,4-tetrahydro-naphthalen-1-ylamine: The title amine was obtained from 4-methyl-3,4-dihydro-2H-naphthalen-1-one (5.00 g, 31.30 mmol), NaBH$_3$CN (13.74 g, 0.22 mol) and NH$_4$OAc (72.30 g, 0.94 mol) according to the protocols as outlined in general procedure C above.

1-(2-Fluoro-ethyl)-3-(4-methyl-1,2,3,4-tetrahydro-naphthalen-1-yl)-urea: The title urea was obtained from 4-methyl-1,2,3,4-tetrahydro-naphthalen-1-ylamine (1.60 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.2 (q, J=8.2, 7.0 Hz, 3H), 1.37-2.03 (m, 4H), 2.78-2.93 (m, 1H), 3.27-3.41 (m, 2H), 4.3 (t, J=5.0 Hz, 1H), 4.5 (t, J=5.3 Hz, 1H), 4.69-4.80 (m, 1H), 5.91-6.04 (m, 1H), 6.25-6.38 (m, 1H), 7.10-7.23 (m, 4H).

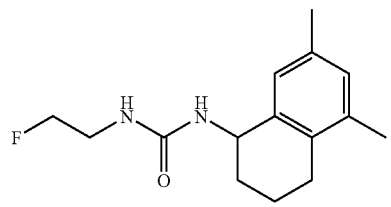

Synthesis of 1-(5,7-Dimethyl-1,2,3,4-tetrahydro-naphthalen-1-yl)-3-(2-fluoro-ethyl)-urea The title compound was generated from commercially available 5,7-Dimethyl-3,4-dihydro-2H-naphthalen-1-one according to the general procedure C described above. The intermediate 5,7-dimethyl-1,2,3,4-tetrahydro-naphthalen-1-ylamine was isolated and characterized.

5,7-Dimethyl-1,2,3,4-tetrahydro-naphthalen-1-ylamine[xxxviii]: The title amine was obtained from 5,7-Dimethyl-3,4-dihydro-2H-naphthalen-1-one (5.00 g, 27.80 mmol), NaBH$_3$CN (12.6 g, 0.20 mol) and NH$_4$OAc (66.40 g, 0.81 mol) according to the protocols as outlined in general procedure C above.

1-(5,7-Dimethyl-1,2,3,4-tetrahydro-naphthalen-1-yl)-3-(2-fluoro-ethyl)-urea: The title urea was obtained from 5,7-dimethyl-1,2,3,4-tetrahydro-naphthalen-1-ylamine (1.75 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.56-1.83 (m, 3H), 2.1 (s, 3H), 2.2 (s, 3H), 2.41-2.55 (m, 2H), 3.22-3.34 (m, 2H), 3.34-3.46 (m, 1H), 4.3 (t, J=5.0 Hz, 1H), 4.5 (t, J=5.0 Hz, 1H), 4.66-4.75 (m, 1H), 6.0 (t, J=5.6 Hz, 1H), 6.2 (d, J=8.5 Hz, 1H), 6.8 (s, 1H), 6.9 (s, 1H).

General procedure H for the Synthesis of Fluoroethyl Substituted (1,2,3,4,-Tetrahydronaphthalen-1-yl) Ureas:

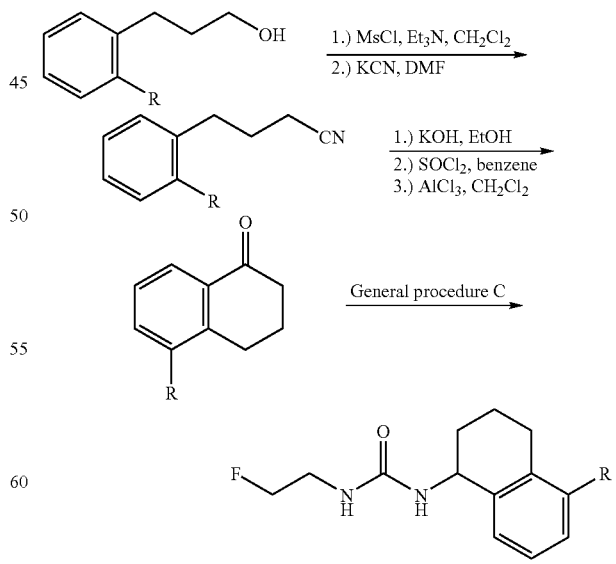

To a solution of 3-(2-substituted-phenyl)-propan-1-ol in CH$_2$Cl$_2$ at 0° C. was added Et$_3$N (2.0 eq) and MsCl (1.5 eq). The resulting mixture was stirred for 1 hour, then washed with H$_2$O (3×100 mL), brine (1×150 mL), dried over MgSO$_4$ and concentrated. The residue was dissolved in DMF and KCN (2.0 eq) was added and the resulting mixture was stirred at 75° C. for 14 hours. After cooling to room temperature, the reaction mixture was quenched into water and extracted with Et$_2$O (3×300 mL). The combined organic extracts were washed with H$_2$O (2×200 mL), brine (1×200 mL), dried over MgSO$_4$ and concentrated to give 4-(2-substituted-phenyl)-butyronitrile. This crude butyronitrile was taken up in ethanol and KOH (2 eq) was added. The resulting mixture was refluxed for 14 hours. The reaction mixture was cooled to room temperature, diluted with water and washed with Et$_2$O (2×150 mL). The aqueous layer was acidified with concentrated HCl and the resulting solution was extracted with Et$_2$O (3×300 mL). The combined organic extracts were washed with H$_2$O (2×200 mL), brine (1×200 mL), dried over MgSO$_4$ and concentrated to give 4-(2-substituted-phenyl)-butyric acid. The crude acid was then dissolved in benzene and SOCl$_2$ (1.5 eq) was added and the reaction mixture was refluxed for 4 hours. After cooling to room temperature, the reaction mixture was concentrated and the residue was taken up in CH$_2$Cl$_2$ and cooled to 0° C. AlCl$_3$ (1.1 eq) was added and the resulting mixture was stirred for 14 hours. The reaction mixture was quenched with HCl, washed with H$_2$O (2×200 mL), brine (1×200 mL), dried over MgSO$_4$ and concentrated to give 5-substituted-3,4-dihydro-2H-naphthalen-1-one. This ketone was thus converted into the desired fluoroethyl cyanoguanidine according to general procedure C.

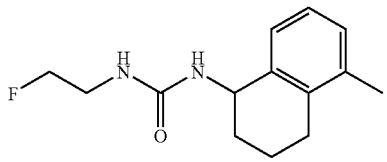

Synthesis of 1-(2-fluoro-ethyl)-3-(5-methyl-1,2,3,4-tetrahydro-naphthalen-1-yl)-urea

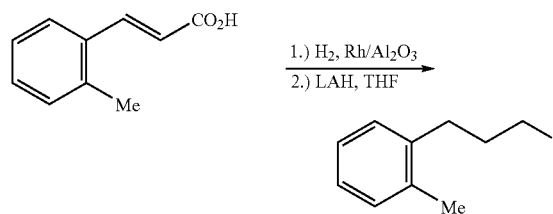

The desired starting 3-o-tolylpropan-1-ol was prepared from the commercially available 3-o-tolyl-acrylic acid using the protocol described in the scheme above. The title urea was thus obtained from this alcohol according to general procedure H. The intermediates 3-o-tolylpropan-1-ol, 4-o-tolyl-butyronitrile, 5-methyl-3,4-dihydro-2H-naphthalen-1-one and 5-methyl-1,2,3,4-tetrahydro-naphthalen-1-ylamine were separated and characterized.

3-o-Tolyl-propan-1-ol[xxxix]: 3-o-Tolyl-acrylic acid (10.00 g, 62.00 mmol) in THF was mixed with Rh/Al$_2$O$_3$ (800 mg) and hydrogenated at 50 psi for 6 hours. The resulting mixture was filtered through a pad of celite and the filtrate was concentrated. The residue was dissolved in THF and cooled to 0° C. LAH (62.00 mL, 1.0 M in THF, 62.00 mmol) was added and the reaction mixture was stirred for 14 hours. The resulting mixture was quenched with NaOH and extracted with Et$_2$O (3×250 mL). The combined organic extracts were washed with H$_2$O (3×150 mL), brine (1×150 mL), dried over MgSO$_4$ and concentrated to give the title alcohol.

4-o-Tolyl-butyronitrile[xl]: The title compound was obtained from 3-o-tolyl-propan-1-ol (taken from the previous step), Et$_3$N (17.20 mL, 0.12 mol), MsCl (7.60 mL, 98.19 mmol) and KCN (8.00 g, 0.12 mol) according to the protocols as outlined in general procedure H.

5-Methyl-3,4-dihydro-2H-naphthalen-1-one[xli]: The title compound was obtained from 4-o-tolyl-butyronitrile (taken from the previous step), KOH (7.00 g, 124.75 mmol), SOCl$_2$ (7.00 mL, 95.96 mmol) and AlCl$_3$ (9.00 g, 67.50 mmol) according to the protocols as outlined in general procedure H.

5-Methyl-1,2,3,4-tetrahydro-naphthalen-1-ylamine: The title amine was obtained from 5-methyl-3,4-dihydro-2H-naphthalen-1-one (7.00 g, 43.80 mmol), NaBH$_3$CN (19.30 g, 0.31 mol) and NH$_4$OAc (101.20 g, 1.31 mol) according to the protocols as outlined in general procedure B.

1-(2-Fluoro-ethyl)-3-(5-methyl-1,2,3,4-tetrahydro-naphthalen-1-yl)-urea: The title compound was obtained from 5-methyl-1,2,3,4-tetrahydro-naphthalen-1-ylamine (10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.58-1.72 (m, 1H), 1.72-1.86 (m, 3H), 2.2 (s, 3H), 2.47-2.60 (m, 2H), 3.26-3.41 (m, 2H), 4.3 (t, J=5.0 Hz, 1H), 4.5 (t, J=5.0 Hz, 1H), 4.71-4.81 (m, 1H), 6.0 (t, J=5.9 Hz, 1H), 6.3 (d, J=8.5 Hz, 1H), 6.98-7.10 (m, 3H). $^{13}$C NMR (75 MHz, DMSO-d$_6$) δ 19.9, 20.1, 26.7, 30.6, 40.5 (d, J=19.5 Hz), 48.0, 84.1 (d, J=164.1 Hz), 125.9, 126.8, 128.6, 135.9, 136.4, 139.1, 158.1.

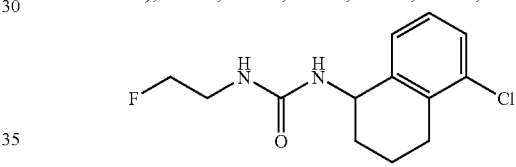

Synthesis of 1-(5-chloro-1,2,3,4-tetrahydro-naphthalen-1-yl)-3-(2-fluoro-ethyl)-urea

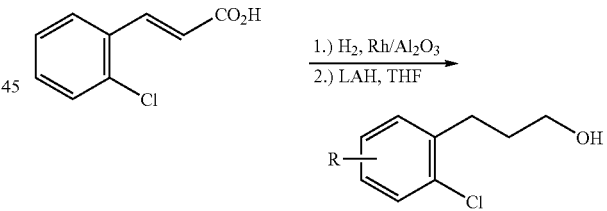

The desired starting 3-(2-chlorophenyl)propan-1-ol was prepared from the commercially available 3-(2-chlorophenyl)-acrylic acid using the protocol described in the scheme above. The title urea was thus obtained from this alcohol according to general procedure H. The intermediates 3-(2-chlorophenyl)propan-1-ol, 4-(2-chlorophenyl)butyronitrile, 5-chloro-3,4-dihydro-2H-naphthalen-1-one and 5-chloro-1,2,3,4-tetrahydro-naphthalen-1-ylamine were separated and characterized.

3-(2-Chloro-phenyl)-propan-1-ol[xlii]: 3-(2-Chloro-phenyl)-acrylic acid (10.00 g, 55.00 mmol) in THF was mixed with Rh/Al$_2$O$_3$ (800 mg) and hydrogenated at 50 psi for 6 hours. The resulting mixture was filtered through a pad of celite and the filtrate was concentrated. The residue was dissolved in THF and cooled to 0° C. LAH (55.00 mL, 1.0 M in THF, 55.00 mmol) was added and the reaction mixture was stirred for 14 hours. The resulting mixture was quenched with NaOH and extracted with Et$_2$O (3×250 mL). The combined organic extracts were washed with H$_2$O (3×150 mL), brine (1×150 mL), dried over MgSO$_4$ and concentrated to give the title alcohol.

4-(2-Chloro-phenyl)-butyronitrile[xliii]: The title compound was obtained from 3-(2-chloro-phenyl)-propan-1-ol (taken from the previous step without further purification), Et$_3$N (15.00 mL, 0.11 mol), MsCl (7.00 mL, 90.44 mmol) and KCN (7.02 g, 0.11 mol) according to the protocols as outlined in procedure H.

5-Chloro-3,4-dihydro-2H-naphthalen-1-one[14]: The title compound was obtained from 4-(2-chloro-phenyl)-butyronitrile (taken from the previous step without further purification), KOH (4.00 g, 71.29 mmol), SOCl$_2$ (4.00 mL, 54.84 mmol) and AlCl$_3$ (5.30 g, 39.75 mmol) according to the protocols as outlined in procedure H.

5-Chloro-1,2,3,4-tetrahydro-naphthalen-1-ylamine[xliv]: The title compound was obtained from 5-Chloro-3,4-dihydro-2H-naphthalen-1-one (6.00 g, 33.30 mmol), NaBH$_3$CN (15.00 g, 0.24 mol) and NH$_4$OAc (77.00 g, 1.00 mol) according to the protocols as outlined in procedure B.

1-(5-Chloro-1,2,3,4-tetrahydro-naphthalen-1-yl)-3-(2-fluoro-ethyl)-urea: The title compound was obtained from 5-chloro-1,2,3,4-tetrahydro-naphthalen-1-ylamine (10.0 mmol), diimidazole carbonyl (1.70 g, 10.48 mmol), fluoro-ethyl amine hydrochloride (1.00 g, 90% purity, 9.05 mmol) and diisopropylethyl amine (3.60 mL, 20.67 mmol) in THF was reacted according to the protocols as outlined in general procedure A above. Spectroscopic data: $^1$H NMR (300 MHz, DMSO-d$_6$) δ 1.59-1.73 (m, 1H), 1.74-1.88 (m, 3H), 2.61-2.76 (m, 2H), 3.27-3.41 (m, 2H), 4.3 (t, J=5.0 Hz, 1H), 4.5 (t, J=5.0 Hz, 1H), 4.75-4.86 (m, 1H), 6.0 (t, J=5.9 Hz, 1H), 6.4 (d, J=8.8 Hz, 1H), 7.15-7.25 (m, 2H), 7.26-7.33 (m, 1H). $^{13}$C NMR (75 MHz, DMSO-d$_6$) δ 19.9, 27.4, 30.2, 40.5 (d, J=19.5 Hz), 47.8, 84.0 (d, J=164.1 Hz), 127.6, 127.85, 127.92, 133.8, 135.1, 142.3, 158.2.

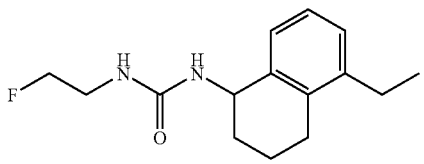

Synthesis of 1-(5-ethyl-1,2,3,4-tetrahydro-naphthalen-1-yl)-3-(2-fluoro-ethyl)-urea

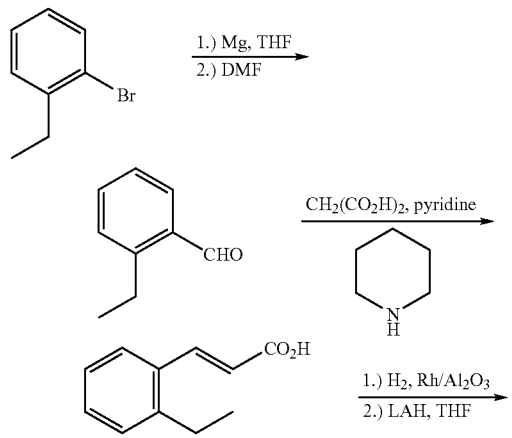

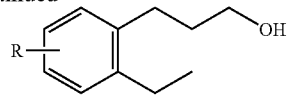

The desired starting 3-(2-ethylphenyl)propan-1-ol was prepared from the commercially available 1-bromo-2-ethyl-benzene using the protocol described in the scheme above. The title urea was thus obtained from this alcohol according to general procedure H. The intermediates 2-ethylbenzaldehyde, 3-(2-ethylphenyl)acrylic acid, 3-(2-ethylphenyl)propan-1-ol, 4-(2-ethylphenyl)butyronitrile, 5-ethyl-3,4-dihydro-2H-naphthalen-1-one and 5-ethyl-1,2,3,4-tetrahydro-naphthalen-1-ylamine were separated and characterized.

2-Ethyl-benzaldehyde[8]: 1-Bromo-2-ethyl-benzene (5.00 g, 27.00 mmol), Mg (4.00 g, 164.54 mmol) and a catalytic amount of 12 in THF were refluxed for 2 hours. The reaction mixture was cooled to 0° C., DMF (10.00 mL, 129.17 mmol) was added. The resulting reaction mixture was stirred for 30 minutes, then was quenched with 10% HCl. The resulting solution was extracted with Et$_2$O (3×200 mL) and the combined organic extracts were washed with H$_2$O (2×200 mL) and brine (1×200 mL), then dried over MgSO$_4$ and concentrated to give the desired title benzaldehyde.

3-(2-Ethyl-phenyl)-acrylic acid[9]: 2-Ethyl-benzaldehyde (18.40 g, 0.14 mol) and malonic acid (28.00 g, 0.27 mol) were mixed in pyridine, then 10.00 mL of piperidine was added. The resulting mixture was slowly refluxed for 3 hours. After cooling to room temperature, the reaction mixture was quenched into cold water, acidified to pH<1 and the resulting solid was filtered, washed with water and dried under vacuum to give the desired title acid.

3-(2-Ethyl-phenyl)-propan-1-ol: 3-(2-Ethyl-phenyl)-acrylic acid (17.00 g, 96.60 mmol) in THF was mixed with Pd/C (1.50 g) and hydrogenated at 50 psi for 6 hours. The resulting mixture was filtered through a pad of celite and the filtrate was concentrated. The residue was dissolved in THF and cooled to 0° C. LAH (100.00 mL, 1.0 M in THF, 0.10 mol) was added and the reaction mixture was stirred for 14 hours. The resulting mixture was quenched with NaOH and extracted with Et$_2$O (3×250 mL). The combined organic extracts were washed with H$_2$O (3×150 mL) and brine (1×150 mL), then dried over MgSO$_4$ and concentrated to give the title alcohol.

4-(2-Ethyl-phenyl)-butyronitrile: The title compound was obtained from 3-(2-ethyl-phenyl)-propan-1-ol (taken from the previous step without further purification), Et$_3$N (13.00 mL, 93.27 mmol), MsCl (5.50 mL, 71.06 mmol) and KCN (6.50 g, 99.82 mmol) according to the protocols as outlined in general procedure H.

5-Ethyl-3,4-dihydro-2H-naphthalen-1-one[xlv]: The title compound was obtained from of 3-(2-ethyl-phenyl)-propionitrile (taken from the previous step without further purification), KOH (4.00 g, 71.29 mmol), SOCl$_2$ (4.00 mL, 54.84 mmol) and AlCl$_3$ (5.40 g, 40.50 mmol) according to the protocols as outlined in general procedure H.

5-Ethyl-1,2,3,4-tetrahydro-naphthalen-1-ylamine: The title compound was obtained from 5-ethyl-3,4-dihydro-2H-naphthalen-1-one (4.50 g, 25.90 mmol), NaBH$_3$CN (11.40 g, 0.18 mol) and NH$_4$OAc (60.00 g, 0.78 mol) according to the protocols as outlined in general procedure B.

1-(5-Ethyl-1,2,3,4-tetrahydro-naphthalen-1-yl)-3-(2-fluoro-ethyl)-urea: The title compound was obtained from 5-ethyl-1,2,3,4-tetrahydro-naphthalen-1-ylamine (10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-$d_6$) δ 1.1 (t, J=7.6 Hz, 3H), 1.62-1.69 (m, 1H), 1.71-1.85 (m, 3H), 2.49-2.58 (m, 3H), 2.60-2.68 (m, 1H), 3.25-3.33 (m, 1H), 3.4 (q, J=5.3 Hz, 1H), 4.3 (t, J=5.3 Hz, 1H), 4.5 (t, J=5.0 Hz, 1H), 4.72-4.81 (m, 1H), 5.9 (t, J=5.9 Hz, 1H), 6.3 (d, J=8.5 Hz, 1H), 7.00-7.12 (m, 3H). $^{13}$C NMR (75 MHz, DMSO-$d_6$) δ 14.9, 20.2, 25.7, 25.9, 30.6, 40.5 (d, J=20.7 Hz), 48.1, 84.1 (d, J=164.1 Hz), 126.2, 126.8, 126.9, 135.2, 139.2, 142.0, 158.1.

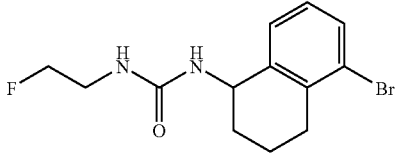

Synthesis of 1-(5-bromo-1,2,3,4-tetrahydro-naphthalen-1-yl)-3-(2-fluoro-ethyl)-urea

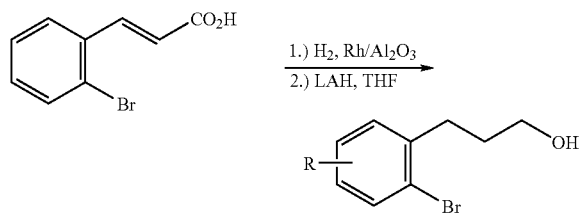

The desired starting 3-(2-bromophenyl)propan-1-ol was prepared from the commercially available 3-(2-bromophenyl)-acrylic acid using the protocol described in the scheme above. The title urea was thus obtained from this alcohol according to general procedure D. The intermediates 3-(2-bromophenyl)propan-1-ol, 4-(2-bromophenyl)butyronitrile, 5-bromo-3,4-dihydro-2H-naphthalen-1-one and 5-bromo-1,2,3,4-tetrahydro-naphthalen-1-ylamine were separated and characterized.

3-(2-Bromo-phenyl)-propan-1-ol[xlvi]: 3-(2-Bromo-phenyl)-acrylic acid 3-o-(10.00 g, 44.00 mmol) in THF was mixed with Rh/Al$_2$O$_3$ (800 mg) and hydrogenated at 50 psi for 6 hours. The resulting mixture was filtered through a pad of celite and the filtrate was concentrated. The residue was dissolved in THF and cooled to 0° C. LAH (44.00 mL, 1.0 M in THF, 44.00 mmol) was added and the reaction mixture was stirred for 14 hours. The resulting mixture was quenched with NaOH and extracted with Et$_2$O (3×250 mL). The combined organic extracts were washed with H$_2$O (3×150 mL), brine (1×150 mL), dried over MgSO$_4$ and concentrated to give the title alcohol.

4-(2-Bromo-phenyl)-butyronitrile[xlvii]: The title compound was obtained from 3-(2-bromo-phenyl)-propan-1-ol (taken from the previous step without further purification), Et$_3$N (12.30 mL, 88.25 mmol), MsCl (5.40 mL, 69.77 mmol) and KCN (5.70 g, 87.53 mmol) according to the protocols as outlined in general procedure H.

5-Bromo-3,4-dihydro-2H-naphthalen-1-one[xlviii]: The title compound was obtained from 4-(2-bromo-phenyl)-butyronitrile, KOH (5.00 g, 89.11 mmol), SOCl$_2$ (4.80 mL, 65.80 mmol) and AlCl$_3$ (6.50 g, 48.75 mmol) according to the protocols as outlined in general procedure H.

5-Bromo-1,2,3,4-tetrahydro-naphthalen-1-ylamine: The title compound was obtained from 5-bromo-3,4-dihydro-2H-naphthalen-1-one (5.00 g, 22.22 mmol), NaBH$_3$CN (9.80 g, 0.16 mol) and NH$_4$OAc (51.40 g, 0.67 mol) according to the protocols as outlined in general procedure B.

1-(5-Bromo-1,2,3,4-tetrahydro-naphthalen-1-yl)-3-(2-fluoro-ethyl)-urea: The title compound was obtained from 5-bromo-1,2,3,4-tetrahydro-naphthalen-1-ylamine (10.0 mmol), diimidazole carbonyl (1.70 g, 10.48 mmol), fluoro-ethyl amine hydrochloride (1.0 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-$d_6$) δ 1.60-1.69 (m, 1H), 1.72-1.86 (m, 3H), 2.58-2.74 (m, 2H), 3.26-3.41 (m, 2H), 4.3 (t, J=5.3 Hz, 1H), 4.5 (t, J=5.3 Hz, 1H), 4.75-4.85 (m, 1H), 6.0 (t, J=5.9 Hz, 1H), 6.4 (d, J=8.5 Hz, 1H), 7.03-7.16 (m, 1H), 7.3 (d, J=7.6 Hz, 1H), 7.5 (d, J=7.0 Hz, 1H).

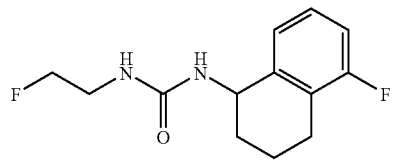

Synthesis of 1-(2-fluoro-ethyl)-3-(5-fluoro-1,2,3,4-tetrahydro-naphthalen-1-yl)-urea

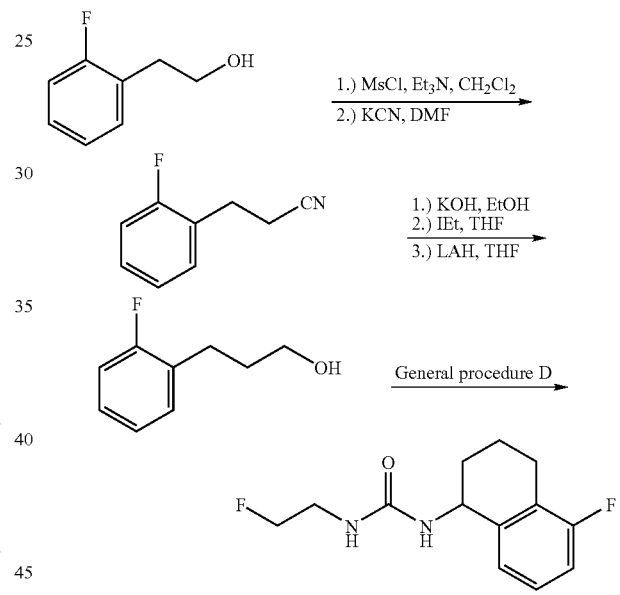

3-(2-Fluoro-phenyl)-propionitrile[xlix]: To a solution of 2-(2-fluoro-phenyl)-ethanol (10.00 g, 71.50 mmol) in CH$_2$Cl$_2$ at 0° C. was added Et$_3$N (20.00 mL, 0.14 mol) followed by MsCl (19.00 mL, 0.25 mol). The resulting mixture was stirred for 1 hour, then washed with H$_2$O (3×100 mL) and brine (1×150 mL), dried over MgSO$_4$ and concentrated. The residue was dissolved in DMF and KCN (9.30 g, 0.14 mol) was added. The resulting mixture was stirred at 75° C. for 14 hours. After cooling to room temperature, the reaction mixture was quenched into water and extracted with Et$_2$O (3×300 mL). The combined organic extracts were washed with H$_2$O (2×200 mL), brine (1×200 mL), dried over MgSO$_4$ and concentrated to give the title compound.

3-(2-Fluoro-phenyl)-propan-1-ol[l]: 3-(2-Fluoro-phenyl)-propionitrile (taken from the previous step without further purification) was dissolved in ethanol and KOH (8.00 g, 0.14 mol) was added. The resulting mixture was refluxed for 14 hours. After cooling to room temperature, the reaction mixture was diluted with water and washed with Et$_2$O (2×150 mL). The aqueous layer was acidified with concentrated HCl, then extracted with Et$_2$O (3×300 mL). The combined organic phases were washed with H₂O (2×200 mL), and brine (1×200 mL), then dried over MgSO₄ and concentrated to give the desired (3-chloro-2-fluoro-phenyl)-acetic acid. The acid was then dissolved in THF and iodoethane (12.00 mL, 0.15 mol) was added. The resulting mixture was refluxed for 2 hours. After cooling to room temperature, the reaction mixture was extracted with Et₂O (3×300 mL) and the combined organic extracts were washed with H₂O (2×200 mL) and brine (1×200 mL), then dried over MgSO₄ and concentrated to give the desired 3-(2-fluoro-phenyl)-propionic acid ethyl ester. This ethyl ester was then dissolved in THF and cooled to 0° C. LAH (72.00 mL, 1.0 M in THF, 72.00 mmol) was added. The resulting reaction mixture was stirred for 14 hours, then quenched with NaOH. The resulting mixture was extracted with Et₂O (3×250 mL) and the combined organic extracts were washed with H₂O (3×150 mL) and brine (1×150 mL), then dried over MgSO₄ and concentrated to give the desired title alcohol.

4-(2-Fluoro-phenyl)-butyronitrile: The title compound was obtained from 3-(2-fluoro-phenyl)-propan-1-ol (taken from the previous step without further purification), Et₃N (20.00 mL, 143.63 mmol), MsCl (9.00 mL, 0.12 mol) and KCN (9.30 g, 0.14 mol) according to the protocols as outlined in general procedure H.

5-Fluoro-3,4-dihydro-2H-naphthalen-1-one: The title compound was obtained from 3-(2-Fluoro-phenyl)-butyronitrile (taken from the previous step without further purification), KOH (8.00 g, 0.14 mol), SOCl₂ (7.00 mL, 95.97 mmol) and AlCl₃ (9.50 g, 71.25 mmol) according to general procedure H.

5-Fluoro-1,2,3,4-tetrahydro-naphthalen-1-ylamine: The title amine was obtained from 5-fluoro-3,4-dihydro-2H-naphthalen-1-one (4.50 g, 27.40 mmol), NaBH₃CN (12.00 g, 0.19 mol) and NH₄OAc (63.40 g, 0.82 mol) according to the protocols as outlined in general procedure B.

1-(2-Fluoro-ethyl)-3-(5-fluoro-1,2,3,4-tetrahydro-naphthalen-1-yl)-urea: The title compound was obtained from 5-fluoro-1,2,3,4-tetrahydro-naphthalen-1-ylamine (1.65 g, 10.00 mmol), diimidazole carbonyl (1.70 g, 10.48 mmol), fluoroethyl amine hydrochloride (1.00 g, 90% purity, 10.48 mmol) and diisopropylethyl amine (3.60 mL, 20.67 mmol) according to the protocols as outlined in general procedure A above. Spectroscopic data: ¹H NMR (300 MHz, DMSO-d₆) δ 1.62-1.69 (m, 1H), 1.72-1.88 (m, 3H), 2.57-2.72 (m, 2H), 3.23-3.34 (m, 1H), 3.4 (q, J=5.3 Hz, 1H), 4.3 (t, J=5.0 Hz, 1H), 4.5 (t, J=5.0 Hz, 1H), 4.75-4.85 (m, 1H), 6.0 (t, J=5.9 Hz, 1H), 6.4 (d, J=8.5 Hz, 1H), 7.0 (t, J=9.1 Hz, 1H), 7.1 (d, J=7.3 Hz, 1H), 7.15-7.23 (m, 1H). ¹³C NMR (75 MHz, DMSO-d₆) δ 19.5, 22.1 (d, J=3.4 Hz), 30.5, 40.5 (d, J=20.7 Hz), 47.4 (d, J=3.4 Hz), 84.1 (d, J=164.1 Hz), 113.3 (d, J=21.8 Hz), 124.6 (d, J=2.3 Hz), 124.9 (d, J=17.2 Hz), 127.4 (d, J=9.2 Hz), 142.2 (d, J=4.6 Hz), 158.2, 160.5 (d, J=242.1 Hz).

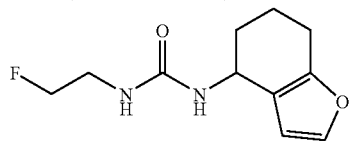

Synthesis of 1-(2-fluoroethyl)-3-(4,5,6,7-tetrahydro-1-benzofuran-4-yl)urea

The title compound was generated from commercially available 6,7-dihydro-5H-benzofuran-4-one according to the general procedure C described above. The intermediate 4,5,6,7-tetrahydro-benzofuran-4-ylamine was isolated and characterized.

4,5,6,7-Tetrahydro-benzofuran-4-ylamine: The title compound was produced from 6,7-dihydro-5H-benzofuran-4-one (5.0 g, 36.72 mmol), NaBH₃CN (13.00 g, 0.21 mol) and NH₄OAc (51.00 g, 0.66 mol) in isopropanol according to the protocols as outlined in general procedure C. Spectroscopic data: ¹H NMR (300 MHz, DMSO-d₆) δ ppm 1.29-1.42 (m, 1H) 1.55-1.70 (m, 1H) 1.79-1.95 (m, 2H) 2.41-2.55 (m, 2H) 3.07 (br s, 2H) 3.70 (td, J=4.62, 2.49 Hz, 1H) 6.42 (d, J=2.05 Hz, 1H) 7.38 (d, J=1.76 Hz, 1H).

1-(2-Fluoroethyl)-3-(4,5,6,7-tetrahydro-1-benzofuran-4-yl)urea: The title compound was generated from 4,5,6,7-Tetrahydro-benzofuran-4-ylamine (crude, taken from the previous step), diimidazole carbonyl (1.80 g, 11.08 mmol), fluoroethyl amine hydrochloride (1.20 g, 90% purity, 10.85 mmol) and diisopropylethyl amine (3.60 mL, 20.67 mmol) according to the protocols as outlined in general procedure A above. Spectroscopic data: ¹H NMR (300 MHz, DMSO-d₆) δ ppm 1.43-1.59 (m, 1H) 1.69-1.84 (m, 2H) 2.42-2.57 (m, 2H) 3.22-3.37 (m, 2H) 4.30 (t, J=4.98 Hz, 1H) 4.46 (t, J=4.98 Hz, 1H) 4.57 (br s, 1H) 5.95 (t, J=5.57 Hz, 1H) 6.12 (d, J=8.21 Hz, 1H) 6.29 (s, 1H) 7.42 (s, 1H).

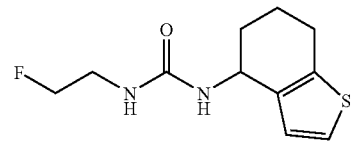

Synthesis of 1-(2-fluoroethyl)-3-(4,5,6,7-tetrahydro-1-benzothien-4-yl)urea

The title compound was generated from commercially available 6,7-dihydro-5H-benzo[b]thiophen-4-one according to the general procedure C described above. The intermediate 4,5,6,7-tetrahydro-benzo[b]thiophen-4-ylamine was isolated and characterized.

4,5,6,7-Tetrahydro-benzo[b]thiophen-4-ylamine[ii]: The title compound was produced from 6,7-dihydro-5H-benzo[b]thiophen-4-one (5.40 g, 35.47 mmol), NaCNBH₃ (12.50 g, 0.20 mol) and NH₄OAc (51.00 g, 0.66 mol) in isopropanol according to the protocols as outlined in general procedure C. Spectroscopic data: ¹H NMR (300 MHz, DMSO-d₆) δ ppm 1.37-1.49 (m, 1H) 1.60-1.74 (m, 1H) 1.83-1.97 (m, 2H) 2.61-2.74 (m, 2H) 3.74 (dd, J=7.33, 4.69 Hz, 1H) 7.03 (d, J=4.98 Hz, 1H) 7.17 (d, J=4.98 Hz, 1H).

1-(2-Fluoroethyl)-3-(4,5,6,7-tetrahydro-1-benzothien-4-yl)urea: The title compound was generated from 4,5,6,7-Tetrahydro-benzo[b]thiophen-4-ylamine (crude, taken from the previous step), diimidazole carbonyl (2.30 g, 14.18 mmol), fluoroethyl amine hydrochloride (1.55 g, 90% purity, 14.02 mmol) and diisopropylethyl amine (4.00 mL, 22.97 mmol) according to the protocols as outlined in general procedure A above. Spectroscopic data: ¹H NMR (300 MHz, DMSO-d₆) δ ppm 1.51-1.65 (m, 1H) 1.73-1.88 (m, 3H) 2.44-2.55 (m, 1H) 2.61-2.76 (m, 2H) 3.23-3.39 (m, 2H) 4.26-4.37 (m, 1H) 4.41-4.54 (m, 1H) 4.62-4.75 (m, 1H) 5.95 (t, J=5.86 Hz, 1H) 6.26 (d, J=8.50 Hz, 1H) 6.79-6.90 (m, 1H) 7.23 (t, J=6.01 Hz, 1H).

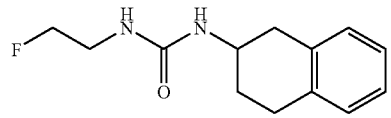

Synthesis of 1-(2-fluoro-ethyl)-3-(1,2,3,4-tetrahydro-naphthalen-2-yl)-urea

The title compound was generated from commercially available 3,4-dihydro-1H-naphthalen-2-one according to the general procedure C described above. The intermediate 1,2,3,4-tetrahydro-naphthalen-2-ylamine was isolated and characterized.

1,2,3,4Tetrahydro-naphthalen-2-ylamine[liii]: The title amine was produced from 3,4-dihydro-1H-naphthalen-2-one (5.00 g, 34.20 mmol), NaBH$_3$CN (15.00 g, 0.24 mol) and NH$_4$OAc (79.00 g, 1.02 mol) according to the protocols as outlined in general procedure C.

1-(2-Fluoro-ethyl)-3-(1,2,3,4-tetrahydro-naphthalen-2-yl)-urea: The title compound was afforded from 1,2,3,4-tetrahydro-naphthalen-2-ylamine (1.5 g, 10.0 mmole), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.54-1.68 (m, 1H), 1.82-1.97 (m, 1H), 2.47-2.62 (m, 1H), 2.71-2.85 (m, 2H), 2.90-3.02 (m, 1H), 3.22-3.37 (m, 2H), 3.77-3.90 (m, 1H), 4.23-4.36 (m, 1H), 4.41-4.51 (m, 1H), 6.0 (br s, 2H), 7.1 (br s, 4H).

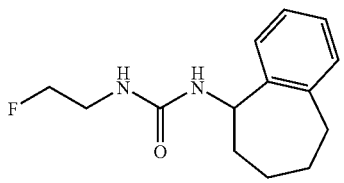

Synthesis of 1-(2-fluoro-ethyl)-3-(6,7,8,9-tetrahydro-5H-benzocyclohepten-5-yl)-urea The title compound was generated from commercially available 6,7,8,9-Tetrahydro-benzocyclohepten-5-one according to the general procedure C described above. The intermediate 6,7,8,9-Tetrahydro-5H-benzocyclohepten-5-ylamine was isolated and characterized.

6,7,8,9-Tetrahydro-5H-benzocyclohepten-5-ylamine[liiii]: The title compound was produced from 6,7,8,9-Tetrahydro-benzocyclohepten-5-one (5.00 g, 31.30 mmol), NaBH$_3$CN (13.70 g, 0.22 mol) and NH$_4$OAc (72.30 g, 0.94 mol) according to the protocols as outlined in general procedure C.

1-(2-Fluoro-ethyl)-3-(6,7,8,9-tetrahydro-5H-benzocyclohepten-5-yl)-urea: The title urea was obtained from 6,7,8,9-tetrahydro-5H-benzocyclohepten-5-ylamine (1.60 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.33-1.48 (m, 1H), 1.63-1.78 (m, 4H), 2.72-2.87 (m, 2H), 3.22-3.37 (m, 3H), 4.3 (t, J=5.0 Hz, 1H), 4.5 (t, J=4.7 Hz, 1H), 4.8 (t, J=8.5 Hz, 1H), 6.2 (t, J=6.2, 5.3 Hz, 1H), 6.5 (d, J=8.5 Hz, 1H), 7.07-7.20 (m, 4H).

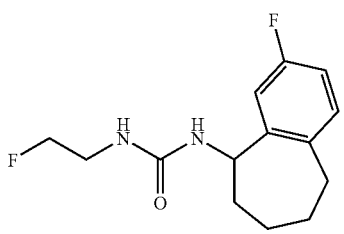

Synthesis of 1-(2-fluoro-ethyl)-3-(3-fluoro-6,7,8,9-tetrahydro-5H-benzocyclohepten-5-yl)-urea The title compound was generated from commercially available 3-fluoro-6,7,8,9-Tetrahydro-benzocyclohepten-5-one according to the general procedure C described above. The intermediate 3-fluoro-6,7,8,9-tetrahydro-5H-benzocyclohepten-5-ylamine was isolated and characterized.

3-Fluoro-6,7,8,9-tetrahydro-5H-benzocyclohepten-5-ylamine: 3-Fluoro-6,7,8,9-tetrahydro-benzocyclohepten-5-one (5.00 g, 28.00 mmol), NaBH$_3$CN (12.50 g, 0.20 mol) and NH$_4$OAc (65.00 g, 0.84 mol) in isopropanol were reacted according to the protocols as outlined in general procedure C to afford the title amine.

1-(2-Fluoro-ethyl)-3-(3-fluoro-6,7,8,9-tetrahydro-5H-benzocyclohepten-5-yl)-urea: The title compound was generated from 3-fluoro-6,7,8,9-tetrahydro-5H-benzocyclohepten-5-ylamine (1.80 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-d$_6$) δ 1.21-1.37 (m, 1H), 1.47-1.60 (m, 1H), 1.68-1.84 (m, 4H), 2.69-2.83 (m, 2H), 3.23-3.38 (m, 2H), 4.3 (t, J=5.0 Hz, 1H), 4.5 (t, J=5.0 Hz, 1H), 4.8 (t, J=8.8 Hz, 1H), 6.2 (t, J=5.6 Hz, 1H), 6.6 (d, J=8.5 Hz, 1H), 6.85-6.98 (m, 2H), 7.08-7.19 (m, 1H).

General Procedure I for the Synthesis of Fluoroethyl Substituted Cycloalk-2-enyl Ureas:

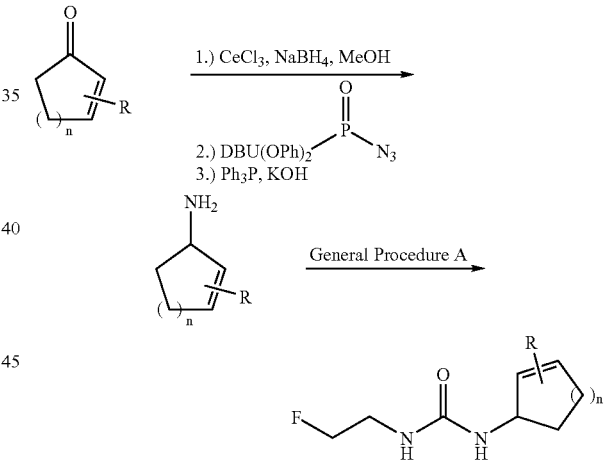

An appropriately substituted cycloalken-2-enone was dissolved in ether, and CeCl$_3$.H$_2$O (1.1 eq) was added. The mixture was colled to 0° C., NaBH$_4$ (1.0 eq) in MeOH was added. After stirring at 0° C. for 1 hour, the reaction mixture was quenched with saturated NH$_4$Cl. The resulting mixture was extracted with Et$_2$O (3×250 mL). The combined organic extracts was thus washed with H$_2$O (3×150 mL), brine (1×150 mL), dried over MgSO$_4$ and concentrated. Column chromatography using hexane:EtOAc (3:2) as eluant gave the desired allylic alcohol. To a solution of thus obtained substituted cycloalken-2-enol in Et$_2$O at 0° C. was added diphenylphosphoryl azide (1.2 eq) followed by slow addition of DBU (1.2 eq). After stirring the reaction mixture overnight, it was decanted and the residue was washed with Et$_2$O. The combined organic layers were concentrated and the residue was treated with Ph$_3$P (1.0 eq) and KOH (1.0 eq) according to the protocols as outlined in general procedure B to give the desired amine. The title urea compound was thus produced from this amine according to the protocol described in general procedure A.

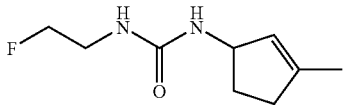

Synthesis of 1-(2-fluoro-ethyl)-3-(3-methyl-cyclopent-2-enyl)-urea

The title compound was generated from commercially available 3-methyl-cyclopent-2-enone according to the General Procedure I described above. The intermediates 3-methyl-cyclopent-2-enol and 3-methyl-cyclopent-2-enylamine were isolated and characterized.

3-Methyl-cyclopent-2-enol[liv]: The title alcohol was obtained from 3-methyl-cyclopent-2-enone (9.71 g, 0.10 mol) according to the General Procedure I described above.

3-Methyl-cyclopent-2-enylamine[lv]: The title compound was obtained from 3-methyl-cyclopent-2-enol (9.00 g, 92.00 mmol) according to general procedure I described above.

1-(2-Fluoro-ethyl)-3-(3-methyl-cyclopent-2-enyl)-urea: The title urea was afforded from 3-methyl-cyclopent-2-enylamine (1.00 g, 10.30 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-$d_6$) δ 1.37-1.52 (m, 1H), 1.7 (s, 3H), 1.97-2.40 (m, 2H), 3.29-3.38 (m, 3H), 4.3 (q, J=5.0 Hz, 1H), 4.4 (q, J=4.7 Hz, 1H), 4.51-4.62 (m, 1H), 5.20-5.33 (m, 1H), 5.86-5.99 (m, 2H).

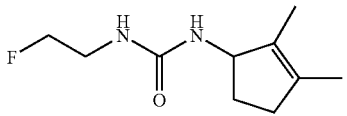

Synthesis of 1-(2,3-Dimethyl-cyclopent-2-enyl)-3-(2-fluoro-ethyl)-urea

The title compound was generated from commercially available 2,3-dimethyl-cyclopent-2-enone according to the general procedure I described above. The intermediates 2,3-dimethyl-cyclopent-2-enol and 2,3-dimethyl-cyclopent-2-enylamine were isolated and characterized.

2,3-Dimethyl-cyclopent-2-enol[lvi]: The title alcohol was obtained from 2,3-dimethyl-cyclopent-2-enone (10.00 g, 91.00 mmol), CeCl$_3$.7H$_2$O (37.20 g, 99.84 mmol) and NaBH$_4$ (3.40 g, 89.88 mmol) according to the protocols as outlined in general procedure I.

2,3-Dimethyl-cyclopent-2-enylamine: The title amine was obtained from 2,3-dimethyl-cyclopent-2-enol (10.00 g, 89.30 mmol), diphenylphosphoryl azide (23.00 mL, 0.11 mol), DBU (16.00 mL, 0.11 mol), Ph$_3$P (23.40 g, 87.84 mmol) and KOH (5.00 g, 89.11 mmol) according to the protocols as outlined in general procedure I.

1-(2,3-Dimethyl-cyclopent-2-enyl)-3-(2-fluoro-ethyl)-urea: The title urea was obtained from 2,3-dimethyl-cyclopent-2-enylamine (1.10 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1$H NMR (300 MHz, DMSO-$d_6$) δ 1.25-1.39 (m, 1H), 1.5 (s, 3H), 1.6 (s, 3H), 2.03-2.15 (m, 3H), 2.17-2.26 (m, 1H), 3.19-3.34 (m, 2H), 4.3 (t, J=5.0 Hz, 1H), 4.4 (t, J=5.0 Hz, 1H), 5.79-5.93 (m, 2H). $^{13}$C NMR (75 MHz, DMSO-$d_6$) δ 11.8, 14.7, 31.5, 35.6, 40.4 (d, J=20.7 Hz), 59.6, 83.0 (d, J=164.1 Hz), 132.6, 133.6, 158.3.

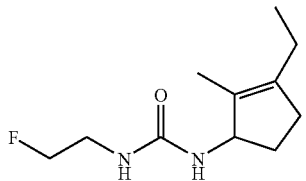

Synthesis of 1-(3-ethyl-2-methyl-cyclopent-2-enyl)-3-(2-fluoro-ethyl)-urea

The desired starting material 3-ethyl-2-methyl-cyclopent-2-enone was prepared from the commercially available 3-ethoxy-2-methyl-cyclopent-2-enone. The title compound was thus generated from this enone according to the general procedure I described above. The intermediates 3-methyl-cyclopent-2-enol and 3-methyl-cyclopent-2-enylamine were isolated and characterized.

3-Ethyl-2-methyl-cyclopent-2-enone[lvii]: Ethylmagnesium chloride (2.0 M in THF, 25.00 mL, 50.00 mmol) was added to 3-ethoxy-2-methyl-cyclopent-2-enone (5.00 g, 35.00 mmol) in THF (20 mL) already cooled to 0 oC. The resulting reaction mixture was stirred for 60 min, then 5% HCl was added and the stirring was continued for another 20 min. The reaction mixture was extracted with ether. The combined ether layers were washed with brine, dried over magnesium sulfate and concentrated to afford the title compound. Spectroscopic data: $^1$H NMR (300 MHz, Solvent) δ ppm 1.06 (t, J=7.62 Hz, 3H) 1.57 (t, J=2.05 Hz, 3H) 2.23-2.26 (m, 2H) 2.40 (q, J=7.62 Hz, 2H) 2.45-2.53 (m, 2H).

3-Ethyl-2-methyl-cyclopent-2-enol[lviii]: The title alcohol was obtained from 3-ethyl-2-methyl-cyclopent-2-enone (crude, from the previous step), cerium trichloride heptahydrate (18.00 g, 48.31 mmol) and sodium borohydride (2.80 g, 74.02 mmol) according to the general procedure I described above.

3-Ethyl-2-ethyl-cyclopent-2-enylamine[lix]: The title compound was obtained from 3-ethyl-2-methyl-cyclopent-2-enol according to general procedure I described above. Spectroscopic data: $^1$H NMR (300 MHz, DMSO-$d_6$) d ppm 0.89 (t, J=7.62 Hz, 3H) 1.19-1.30 (m, 1H) 1.35 (br s, 2H) 1.54 (s, 3H) 1.95-2.09 (m, 4H) 2.14-2.28 (m, 1H) 3.50 (br s, 1H).

1-(3-Ethyl-2-methyl-cyclopent-2-enyl)-3-(2-fluoro-ethyl)-urea: The title urea was afforded from 3-ethyl-2-methyl-cyclopent-2-enylamine (crude, taken from the previous step without further purification), diimidazole carbonyl (1.62 g, 10.00 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-$d_6$) δ ppm 0.91 (td, J=7.55, 1.61 Hz, 3H) 1.26-1.41 (m, 1H) 1.49 (s, 3H) 1.97-2.13 (m, 3H) 2.24 (s, 1H) 2.48 (d, J=1.76 Hz, 1H) 3.13-3.27 (m, 1H) 3.29-3.32 (m, 1H) 4.22-4.35 (m, 1H) 4.44 (s, 1H) 4.45 (d, J=1.76 Hz, 1H) 5.78-5.93 (m, 2H).

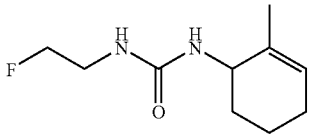

Synthesis of 1-(2-fluoro-ethyl)-3-(2-methyl-cyclohex-2-enyl)-urea

The title compound was generated from commercially available 2-methyl-cyclohex-2-enone according to general procedure I described above. The intermediates 2-methyl-cyclohex-2-enol, 6-Azido-1-methyl-cyclohexene and 2-methyl-cyclohex-2-enylamine were isolated and characterized.

2-Methyl-cyclohex-2-enol[lx]: 5.59 g (69%) of the title alcohol was generated from NaBH$_4$ (2.74 g, 72.40 mmol), 2-methyl-cyclohex-2-enone (8.00 g, 72.6 mmol) and CeCl$_3$.7H$_2$O (29.80 g, 80.00 mmol) according to general procedure I described above. Spectroscopic data: $^1$H NMR (300 MHz, CDCl$_3$) δ 1.42-1.83 (m, 8H), 1.92-2.07 (m, 2H), 3.94-4.03 (m, 1H), 5.52-5.57 (m, 1H).

6-Azido-1-methyl-cyclohexene: 2.53 g (37%) of the title azide was obtained from diphenylphosphoryl azide (13.00 mL, 47.24 mmol), 2-methyl-cyclohex-2-enol (5.60 g, 49.90 mmol) and DBU (9.00 mL, 60.20 mmol) according to general procedure I described above. Spectroscopic data: $^1$H NMR (300 MHz, CDCl$_3$) δ 1.56-1.68 (m, 2H), 1.77 (s, 3H), 1.79-2.14 (m, 4H), 3.63-3.70 (m, 1H), 5.66-5.72 (m, 1H).

2-Methyl-cyclohex-2-enylamine[lxi]: The title amine was obtained from 6-azido-1-methyl-cyclohexene (2.53 g, 18.40 mmol), triphenyl phosphine (4.90 g, 18.7 mmol) and KOH (1.80 g, 17.8 mmol) according to general procedure I described above. Spectroscopic data: $^1$H NMR (300 MHz, CDCl$_3$) δ 1.43-1.71 (m, 4H), 1.71-1.77 (m, 3H), 1.76-1.89 (m, 2H), 1.89-2.06 (m, 2H), 3.12-3.18 (m, 1H), 5.40-5.47 (m, 1H).

1-(2-Fluoro-ethyl)-3-(2-methyl-cyclohex-2-enyl)-urea: The title compound was obtained from 2-methyl-cyclohex-2-enylamine (1.30 g, 11.70 mmol), diimidazole carbonyl (1.90 g, 11.71 mmol), fluoroethyl amine hydrochloride (1.20 g, 90% purity, 10.85 mmol) and diisopropyl ethyl amine (4.00 mL, 22.97 mmol) according to the protocols as outlined in general procedure A. Spectroscopic data: $^1$H NMR (500 MHz, DMSO-d$_6$) δ 1.42-1.64 (m, 7H), 1.88-1.97 (m, 2H), 3.27 (q, J=5.37 Hz, 1H), 3.33 (q, J=5.86, 4.88 Hz, 1H), 3.94-3.99 (m, 1H), 4.34 (t, J=4.88 Hz, 1H), 4.43 (t, J=4.88 Hz, 1H), 5.45-5.51 (m, 1H), 5.94 (t, J=5.86 Hz, 1H), 5.99 (d, J=8.79 Hz, 1H). $^{13}$C NMR (126 MHz, DMSO-d$_6$) δ 19.07, 21.59, 25.46, 30.93, 40.49 (d, J=20.62 Hz), 47.67, 84.15 (d, J=163.97 Hz), 125.08, 135.08, 158.30.

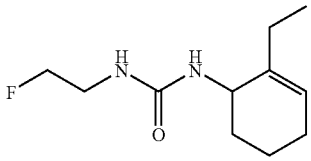

Synthesis of 1-(2-ethyl-cyclohex-2-enyl)-3-(2-fluoro-ethyl)-urea

The title compound was generated from commercially available 2-ethyl-cyclohex-2-enone according to general procedure I described above. The intermediates 2-ethyl-cyclohex-2-enol, 6-azido-1-ethyl-cyclohexene and 2-ethyl-cyclohex-2-enylamine were isolated and characterized.

2-Ethyl-cyclohex-2-enol[lxii]: The title alcohol was obtained from NaBH$_4$ (2.50 g, 66.10 mmol), 2-ethyl-cyclohex-2-enone (8.35 g, 67.25 mmol) and CeCl$_3$.7H$_2$O (27.60 g, 74.07 mmol) according to the protocols as outlined in general procedure I. Spectroscopic data: $^1$H NMR (300 MHz, CDCl$_3$) δ 1.05 (t, J=7.33 Hz, 3H), 1.43-1.84 (m, 5H), 1.87-2.22 (m, 4H), 4.03-4.12 (m, 1H), 5.51-5.59 (m, 1H).

6-Azido-1-ethyl-cyclohexene: The title azide was obtained from diphenylphosphoryl azide (14.50 mL, 67.28 mmol), 2-ethyl-cyclohex-2-enol (7.06 g, 56.00 mmol) and DBU (10.00 mL, 66.87 mmol) according to the protocols as outlined in general procedure I. Spectroscopic data: $^1$H NMR (300 MHz, CDCl$_3$) δ 1.05 (t, J=7.33 Hz, 3H), 1.58-2.20 (m, 8H), 3.71-3.77 (m, 1H), 5.68-5.73 (m, 1H).

2-Ethyl-cyclohex-2-enylamine[lxiii]: The title amine was generated from 6-azido-1-ethyl-cyclohexene (5.70 g 37.71 mmol), triphenyl phosphine (10.00 g, 38.12 mmol) and KOH (2.14 g, 38.14 mmol) according to the protocols as outlined in general procedure I. Spectroscopic data: $^1$H NMR (300 MHz, CDCl$_3$) δ 0.99 (t, J=7.33 Hz, 3H), 1.46-1.86 (m, 5H), 1.87-2.19 (m, J=32.00 Hz, 5H), 3.19-3.26 (m, 1H), 5.41-5.46 (m, 1H).

1-(2-Ethyl-cyclohex-2-enyl)-3-(2-fluoro-ethyl)-urea: The title compound was obtained from 2-ethyl-cyclohex-2-enylamine (3.46 g, 27.60 mmol), diimidazole carbonyl (4.50 g, 27.73 mmol), fluoroethyl amine hydrochloride (2.80 g, 90% purity, 25.33 mmol) and diisopropyl ethyl amine (9.60 mL, 55.12 mmol) according to the protocols as outlined in general procedure A. Spectroscopic data: $^1$H NMR (500 MHz, DMSO-d$_6$) δ 0.94 (t, J=7.32 Hz, 3H), 1.47-1.57 (m, 4H), 1.90-1.98 (m, 4H), 3.27 (q, J=5.37 Hz, 1H), 3.33 (q, J=5.37 Hz, 1H), 4.04-4.09 (m, 1H), 4.33 (t, J=5.37 Hz, 1H), 4.43 (t, J=4.88 Hz, 1H), 5.46-5.50 (m, 1H), 5.93 (t, J=5.86 Hz, 1H), 5.97 (d, J=9.28 Hz, 1H). $^{13}$C NMR (126 MHz, DMSO-d$_6$) δ 13.12, 18.97, 25.38, 27.37, 31.06, 40.49 (d, J=20.14 Hz), 45.90, 84.17 (d, J=163.97 Hz), 123.26, 140.48, 158.20.

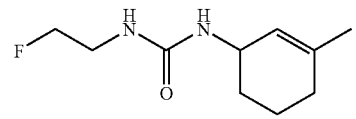

Synthesis of 1-(2-fluoro-ethyl)-3-(3-methyl-cyclohex-2-enyl)-urea

The title compound was generated from commercially available 3-methyl-cyclohex-2-enone according to general procedure I described above. The intermediates 3-methyl-cyclohex-2-enol, 3-azido-1-methyl-cyclohexene and 3-methyl-cyclohex-2-enylamine were isolated and characterized.

3-Methyl-cyclohex-2-enol[lxiv]: The title alcohol was obtained from NaBH$_4$ (1.72 g, 45.47 mmol), 3-methyl-cyclohex-2-enone (5.00 g, 45.40 mmol) and CeCl$_3$.7H$_2$O (18.6 g, 50.00 mmol) according to the protocols as outlined in general procedure I. Spectroscopic data: $^1$H NMR (300 MHz, CDCl$_3$) δ 1.53-1.63 (m, 3H), 1.66-1.72 (m, 3H), 1.72-1.85 (m, 2H), 1.87-1.96 (m, 2H), 4.12-4.24 (m, 1H), 5.44-5.55 (m, 1H).

3-Azido-1-methyl-cyclohexene[lxv]: The title azide was generated from diphenylphosphoryl azide (9.70 mL, 44.87 mmol), 3-methyl-cyclohex-2-enol (4.21 g, 37.54 mmol) and DBU (6.70 mL, 44.8 mmol) according to the protocols as outlined in general procedure I. Spectroscopic data: $^1$H NMR (300 MHz, CDCl$_3$) δ 1.63-1.70 (m, 2H), 1.72-1.82 (m, 5H), 1.91-2.05 (m, 2H), 3.83-3.91 (m, 1H), 5.44-5.49 (m, 1H).

3-Methyl-cyclohex-2-enylamine[lxvi]: The title amine was afforded from 3-azido-1-methyl-cyclohexene (3.78 g, 27.60 mmol), triphenyl phosphine (7.30 g, 27.80 mmol) and KOH (1.56 g, 27.80 mmol) according to the protocols as outlined in general procedure I. Spectroscopic data: $^1$H NMR (300 MHz, CDCl$_3$) δ 1.09-1.33 (m, 2H), 1.50-1.62 (m, 1H), 1.63-1.67 (m, 3H), 1.68-1.97 (m, 5H), 3.26-3.34 (m, 1H), 5.32-5.37 (m, 1H).

1-(2-Fluoro-ethyl)-3-(3-methyl-cyclohex-2-enyl)-urea: The title compound was obtained from 3-methyl-cyclohex-2-enylamine (2.95 g, 26.50 mmol), diimidazole carbonyl (4.30 g, 26.50 mmol), fluoroethyl amine hydrochloride (2.64 g, 90% purity, 23.88 mmol) and diisopropyl ethyl amine (9.30 mL, 53.39 mmol) according to the protocols as outlined in general procedure A. Spectroscopic data: $^1$H NMR (500 MHz, DMSO-d$_6$) δ 1.25-1.37 (m, 1H), 1.52-1.66 (m, 6H), 1.78-1.92 (m, 2H), 3.23 (q, J=5.57, 4.69 Hz, 1H), 3.33 (q, J=5.57, 4.69 Hz, 1H), 3.99-4.08 (m, 1H), 4.29 (t, J=4.98 Hz, 1H), 4.45 (t, J=5.28 Hz, 1H), 5.26-5.29 (m, 1H), 5.85-5.97 (m, 2H). $^{13}$C NMR (75.5 MHz, DMSO-d$_6$) δ 25.01, 28.78, 34.80, 34.92, 45.13 (d, J=19.50 Hz), 50.00, 88.83 (d, J=164.06 Hz), 129.10, 141.45, 162.63.

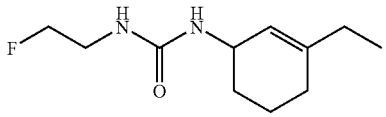

Synthesis of 1-(3-Ethyl-cyclohex-2-enyl)-3-(2-fluoro-ethyl)-urea

The desired starting material 3-ethyl-cyclohex-2-enone was prepared from the commercially available 3-ethoxy-cyclohex-2-enone. The title compound was thus generated from this enone according to general procedure I described above. The intermediates 3-ethyl-cyclohex-2-enone, 3-ethyl-cyclohex-2-enol, 3-azido-1-ethyl-cyclohexene and 3-ethyl-cyclohex-2-enylamine were isolated and characterized.

3-Ethyl-cyclohex-2-enone[lxvii]: To a solution of 3-ethoxy-cyclohex-2-enone (8.50 g, 60.60 mmol) in THF at 0° C. was added EtMgBr (3.0 M in THF, 24.30 mL, 72.90 mmol) dropwise. The reaction mixture was stirred for 1 hour after which it was quenched with 1N HCl. The resulting solution was then stirred for 1 hour and extracted with Et$_2$O (3×200 mL), and the combined organic extracts were washed with H$_2$O (3×100 mL), brine (1×200 mL), dried over MgSO$_4$ and concentrated. Purification by column chromatography using hexane:EtOAc (3:2) as eluant gave 5.00 g (66.7%) of the title enone. Spectroscopic data: $^1$H NMR (300 MHz, CDCl$_3$) δ 1.11 (t, J=7.92, 7.04 Hz, 3H), 1.95-2.05 (m, 3H), 2.19-2.40 (m, 5H), 5.88 (s, 1H).

3-Ethyl-cyclohex-2-enol[72]: 4.50 g (90%) of the title alcohol was obtained from NaBH$_4$ (1.52 g, 40.20 mmol), 3-ethyl-cyclohex-2-enone (5.00 g, 40.30 mmol) and CeCl$_3$.7H$_2$O (16.50 g, 44.30 mmol) according to the protocols as outlined in general procedure I. Spectroscopic data: $^1$H NMR (300 MHz, CDCl$_3$) δ 1.01 (t, J=7.33 Hz, 3H), 1.53-1.64 (m, 3H), 1.70-1.86 (m, 2H), 1.90-2.03 (m, 4H), 4.16-4.25 (m, 1H), 5.47-5.52 (m, 1H).

3-Azido-1-ethyl-cyclohexene: The title azide was afforded from diphenylphosphoryl azide (9.30 mL, 43.00 mmol), 3-ethyl-cyclohex-2-enol (4.50 g, 35.70 mmol) and DBU (6.40 mL, 42.80 mmol) according to the protocols as outlined in general procedure I. Spectroscopic data: $^1$H NMR (300 MHz, CDCl$_3$) δ 1.03 (t, J=7.33 Hz, 3H), 1.54-1.87 (m, 3H), 1.93-2.08 (m, 5H), 3.85-3.93 (m, 1H), 5.43-5.48 (m, 1H).

3-Ethyl-cyclohex-2-enylamine: The title amine was generated from 3-azido-1-ethyl-cyclohexene (2.27 g, 15.00 mmol), triphenyl phosphine (4.00 g, 15.20 mmol) and KOH (0.85 g, 15.20 mmol) according to the protocols as outlined in general procedure I. Spectroscopic data: $^1$H NMR (300 MHz, CDCl$_3$) δ 0.99 (t, J=7.62 Hz, 3H), 1.09-1.34 (m, 2H), 1.48-1.62 (m, 1H), 1.69-1.79 (m, 1H), 1.83-1.98 (m, 6H), 3.26-3.40 (m, 1H), 5.29-5.38 (m, 1H).

1-(3-Ethyl-cyclohex-2-enyl)-3-(2-fluoro-ethyl)-urea: The title urea was obtained from 3-ethyl-cyclohex-2-enylamine (2.10 g, 16.80 mmol), diimidazole carbonyl (2.70 g, 16.64 mmol), fluoroethyl amine hydrochloride (1.70 g, 90% purity, 15.38 mmol) and diisopropyl ethyl amine (5.80 mL, 33.30 mmol) according to the protocols as outlined in general procedure A. Spectroscopic data: $^1$H NMR (500 MHz, DMSO-d$_6$) δ 0.95 (t, J=7.33 Hz, 3H), 1.26-1.39 (m, 1H), 1.52-1.68 (m, 3H), 1.84-1.97 (m, 4H), 3.23 (q, J=5.28 Hz, 1H), 3.33 (q, J=6.16, 5.28, 4.40 Hz, 1H), 4.01-4.11 (m, 1H), 4.30 (t, J=5.28 Hz, 1H), 4.45 (t, J=5.57, 4.98 Hz, 1H), 5.21-5.30 (m, 1H), 5.86-5.99 (m, 2H). $^{13}$C NMR (75.5 MHz, DMSO-d$_6$) δ 12.66, 20.39, 28.42, 30.33, 30.52, 40.41 (d, J=20.65 Hz), 45.23, 84.11 (d, J=164.07 Hz), 122.54, 142.02, 157.89.

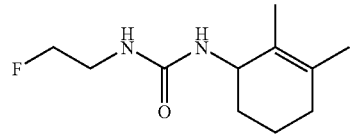

Synthesis of 1-(2,3-dimethyl-cyclohex-2-enyl)-3-(2-fluoro-ethyl)-urea

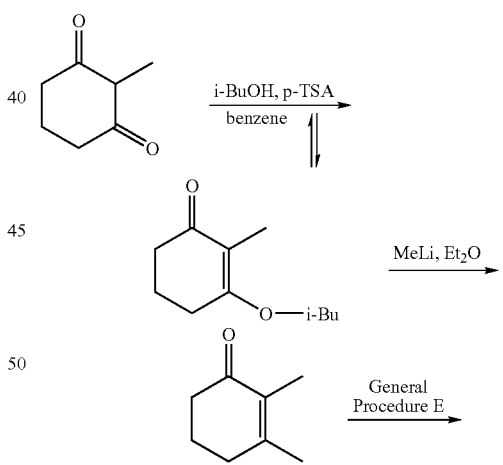

The desired starting material 2,3-dimethyl-cyclohex-2-enone was prepared from the commercially available 2-methyl-cyclohexane-1,3-dione. The title compound was thus generated from this enone according to general procedure I described above. The intermediates 3-isobutoxy-2-methyl-cyclohex-2-enone, 2,3-dimethyl-cyclohex-2-enone, 2,3- dimethyl-cyclohex-2-enol, 3-azido-1,2-dimethyl-cyclohexene and 2,3-dimethyl-cyclohex-2-enylamine were isolated and characterized.

3-Isobutoxy-2-methyl-cyclohex-2-enone: A solution of 2-methyl-cyclohexane-1,3-dione (20.00 g, 0.16 mol), i-BuOH (37.40 mL, 0.39 mol) and p-TSA (500 mg) in benzene was fitted with a Dean-Stark trap and refluxed for 14 hours. After cooling to room temperature, the resulting mixture was washed with dilute NaHCO$_3$ (3×150 mL). The NaHCO$_3$ solution was then back-extracted with Et$_2$O (1×200 mL). The combined ether and benzene fractions were concentrated and purified by column chromatography using hexane:Et$_2$O (3:2) as eluant to give 14.51 g (50.3%) of the title enone. Spectroscopic data: $^1$H NMR (300 MHz, CDCl$_3$) δ 0.94 (t, J=7.33 Hz, 3H), 1.25 (d, J=6.16 Hz, 3H), 1.54-1.68 (m, 2H), 1.71 (t, J=1.47 Hz, 3H), 1.90-2.02 (m, 2H), 2.29-2.39 (m, 2H), 2.45-2.54 (m, 2H), 4.25-4.37 (m, 1H).

2,3-Dimethyl-cyclohex-2-enone[lxviii]: To a solution of MeLi (79.70 mL, 127.52 mmol) in 150 mL of Et$_2$O at 0° C. was added dropwise 3-isobutoxy-2-methyl-cyclohex-2-enone (14.51 g, 79.70 mmol) in 50 mL of Et$_2$O. The resulting mixture was stirred for 1.5 hours, quenched into water and acidified with dilute H$_2$SO$_4$ to pH 1. The mixture was extracted with Et$_2$O (3×250 mL), and the combined organic extracts were washed with H$_2$O (3×100 mL), brine (1×200 mL), dried over MgSO$_4$ and concentrated. Purification by column chromatography using hexane:Et$_2$O (4:1) as eluant gave 7.00 g (71%) of the title enone. Spectroscopic data: $^1$H NMR (300 MHz, CDCl$_3$) δ 1.75-1.80 (m, 3H), 1.89-1.98 (m, 5H), 2.36 (s, 4H).

2,3-Dimethyl-cyclohex-2-enol[lxix]: The title alcohol was obtained from NaBH$_4$ (2.13 g, 56.30 mmol), 2,3-dimethyl-cyclohex-2-enone (7.00 g, 56.40 mmol) and CeCl$_3$.7H$_2$O (23.10 g, 62.00 mmol) according to the protocols as outlined in general procedure I. Spectroscopic data: $^1$H NMR (300 MHz, CDCl$_3$) δ 1.48-1.80 (m, 12H), 1.84-1.99 (m, 1H), 3.91-3.99 (m, 1H).

3-Azido-1,2-dimethyl-cyclohexene: The title azide was afforded from diphenylphosphoryl azide (13.60 mL, 63.10 mmol), 2,3-dimethyl-cyclohex-2-enol (6.62 g, 52.50 mmol) and DBU (9.40 mL, 62.97 mmol) according to the protocols as outlined in general procedure I. Spectroscopic data: $^1$H NMR (300 MHz, CDCl$_3$) δ 1.61-1.76 (m, 11H), 1.88-2.03 (m, 1H), 3.65-3.70 (m, 1H).

2,3-Dimethyl-cyclohex-2-enylamine: The title compound was generated from 3-azido-1,2-dimethyl-cyclohexene (6.60 g, 43.70 mmol), triphenyl phosphine (11.60 g, 44.20 mmol) and KOH (2.50 g, 44.60 mmol) according to the protocols as outlined in general procedure I. Spectroscopic data: $^1$H NMR (300 MHz, CDCl$_3$) δ 1.45-1.82 (m, 13H), 1.88-1.96 (m, 1H), 3.10-3.17 (m, 1H).

1-(2,3-Dimethyl-cyclohex-2-enyl)-3-(2-fluoro-ethyl)-urea: The title urea was obtained from 2,3-dimethyl-cyclohex-2-enylamine (3.79 g, 30.30 mmol), diimidazole carbonyl (4.90 g, 30.20 mmol), fluoroethyl amine hydrochloride (3.00 g, 90% purity, 27.14 mmol) and diisopropyl ethyl amine (10.60 mL, 60.86 mmol) according to the protocols as outlined in general procedure A. Spectroscopic data: $^1$H NMR (500 MHz, DMSO-d$_6$) δ 1.45-1.52 (m, 4H), 1.52-1.58 (m, 6H), 1.76-1.90 (m, 2H), 3.22 (q, J=5.57, 4.98 Hz, 1H), 3.32 (q, J=5.28 Hz, 1H), 3.86-3.95 (m, 1H), 4.26 (t, J=4.98 Hz, 1H), 4.43 (t, J=5.28 Hz, 1H), 5.84-5.97 (m, 2H). $^{13}$C NMR (75.5 MHz, DMSO-d$_6$) δ 17.12, 19.17, 19.85, 30.88, 31.90, 40.44 (d, J=20.65 Hz), 48.76, 84.12 (d, J=164.06 Hz), 127.06, 129.72, 158.29.

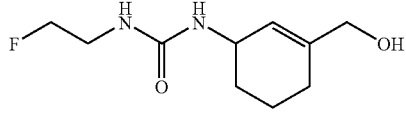

Synthesis of 1-(2-Fluoro-ethyl)-3-(3-hydroxymethyl-cyclohex-2-enyl)-urea

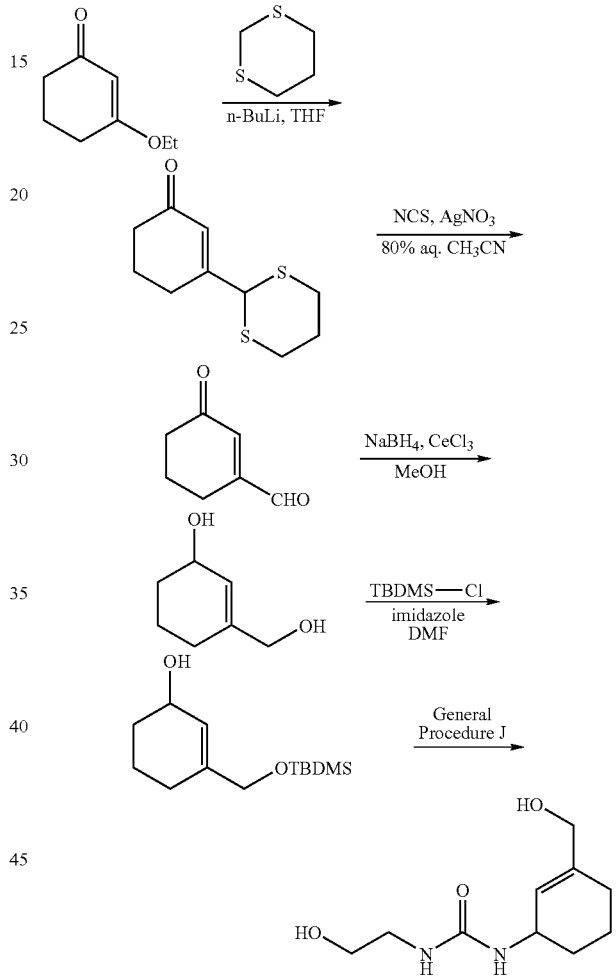

3-[1,3]Dithian-2-yl-cyclohex-2-enone[lxx]: To a solution of 1,3-dithiane (14.00 g, 116.40 mmol) in THF at −78° C. was added dropwise n-BuLi (46.6 mL, 2.5 M in hexanae, 116.50 mmol). The resulting mixture was stirred for 2 hours, then 3-ethoxy-cyclohex-2-enone (16.30 g, 116.30 mmol) in THF was added in a dropwise fashion. The resulting mixture was stirred for 1 hour, then warmed to 0° C. H$_2$SO$_4$ was added and the resulting mixture was stirred for another hour. The reaction mixture was then poured into brine and extracted with Et$_2$O (3×300 mL). The combined organic extracts were washed with NaHCO$_3$ (1×300 mL), brine (1×300 mL), dried over MgSO$_4$ and concentrated. Purification by column chromatography using hexane:EtOAc (4:1) as eluant gave 18.51 g (74%) of the title enone. Spectroscopic data: $^1$H NMR (300 MHz, CDCl$_3$) δ 1.81-2.21 (m, 6H), 2.34-2.43 (m, 2H), 2.47-2.54 (m, 2H), 2.86-2.99 (m, 2H), 4.65 (s, 1H), 6.21 (s, 1H).

3-Oxo-cyclohex-1-enecarbaldehyde[lxxi]: To a solution of N-chlorosuccinimide (2.00 g, 15.00 mmol) and AgNO$_3$ (2.93 g, 17.20 mmol) in 20 mL of 80% aqueous CH$_3$CN at 0° C. was added 3-[1,3]dithian-2-yl-cyclohex-2-enone (1.00 g, 4.70 mmol) dissolved in 4 mL CH$_3$CN. The resulting reaction mixture was stirred for 30 minutes, 5.20 g of Na$_2$S$_2$O$_3$ in 10 mL of H$_2$O was then added followed by 6.00 g of Na$_2$CO$_3$ in 10 mL of H$_2$O. The resulting mixture was stirred for 5 minutes and filtered through a pad of celite. The celite was washed with EtOAc and the combined organic phases were washed with brine (1×15 mL), dried over MgSO$_4$ and concentrated. Purification by column chromatography using hexane:EtOAc (4:1) as eluant gave 220 mg (38%) of the desired title aldehyde. Spectroscopic data: $^1$H NMR (300 MHz, CDCl$_3$) δ 2.01-2.11 (m, 2H), 2.45-2.56 (m, 4H), 6.53 (t, J=1.76 Hz, 1H), 9.75-9.77 (m, 1H).

3-Hydroxy ethyl-cyclohex-2-eno[lxxii]: A sample of NaBH$_4$ (551 mg, 14.60 mmol) was added to a cooled (0° C.) solution of 3-oxo-cyclohex-1-enecarbaldehyde (1.81 g, 14.60 mmol) and CeCl$_3$.7H$_2$O (6.00 g, 16.10 mmol) in MeOH. The reaction mixture was stirred for 1 hour and then filtered through a pad of SiO$_2$ using CH$_2$Cl$_2$:MeOH (4.5:0.5) as the eluant. Concentration of the combined organic phases afforded the desired title diol. Spectroscopic data: $^1$H NMR (300 MHz, CDCl$_3$) δ 1.53-1.65 (m, 2H), 1.69-2.08 (m, 4H), 2.31 (s, 2H), 3.99 (s, 2H), 4.19-4.27 (m, 1H), 5.70-5.77 (m, 1H).

3-(tert-Butyl-dimethyl-silanyloxymethyl)-cyclohex-2-enol[80]: 1.54 g (54%) of the desired title compound was obtained from 3-hydroxymethyl-cyclohex-2-enol (1.50 g, 11.70 mmol), TBDMS-Cl (2.20 g, 14.60 mmol) and imidazole (2.02 g, 29.70 mmol) according to the protocols as outlined in general procedure J. Spectroscopic data: $^1$H NMR (300 MHz, CDCl$_3$) δ 0.00 (s, 6H), 0.82 (s, 9H), 1.44-1.61 (m, 3H), 1.62-1.92 (m, 4H), 3.95 (s, 2H), 4.13-4.20 (m, 1H), 5.67-5.71 (m, 1H).

(3-Azido-cyclohex-1-enylmethoxy)-tert-butyl-dimethyl-silane: The title compound was obtained from diphenylphosphoryl azide (1.70 mL, 7.90 mmol), 3-(tert-butyl-dimethyl-silanyloxymethyl)-cyclohex-2-enol (1.54 g, 6.40 mmol) and DBU (1.20 mL, 8.00 mmol) according to general procedure I. Spectroscopic data: $^1$H NMR (300 MHz, CDCl$_3$) δ-0.01 (s, 6H), 0.83 (s, 9H), 1.50-1.92 (m, 6H), 3.82-3.89 (m, 1H), 3.97-4.00 (m, 2H), 5.64-5.69 (m, 1H).

3-(tert-Butyl-dimethyl-silanyloxymethyl)-cyclohex-2-enylamine: The desired title amine was obtained from (3-azido-cyclohex-1-enylmethoxy)-tert-butyl-dimethyl-silane (600 mg, 2.20 mmol), triphenyl phosphine (595 mg, 2.30 mmol) and KOH (127 mg, 2.30 mmol) according to the protocols as outlined in general procedure I. Spectroscopic data: $^1$H NMR (300 MHz, CDCl$_3$) δ 0.00 (s, 6H), 0.82 (s, 9H), 1.13-1.30 (m, 3H), 1.39-1.90 (m, 5H), 3.19-3.34 (m, 1H), 3.94 (s, 2H), 5.40-5.68 (m, 1H).

1-[3-(tert-Butyl-dimethyl-silanyloxy ethyl)-cyclohex-2-enyl]-3-(2-fluoro-ethyl)-urea: The title urea was obtained from 3-(tert-butyl-dimethyl-silanyloxymethyl)-cyclohex-2-enylamine (2.24 mmol, crude, taken directly from the previous step without further purification), diimidazole carbonyl (364 mg, 2.24 mmol), fluoroethyl amine hydrochloride (223 mg, 90% purity, 2.01 mmol) and diisopropyl ethyl amine (782 µL, 4.49 mmol) according to the protocols as outlined in general procedure A. Spectroscopic data: $^1$H NMR (300 MHz, CDCl$_3$) δ 0.00 (s, 6H), 0.84 (s, 9H), 1.41-1.51 (m, 1H), 1.53-1.64 (m, 3H), 1.75-1.89 (m, 4H), 3.40 (t, J=4.69 Hz, 1H), 3.49 (t, J=4.69 Hz, 1H), 3.92-3.96 (m, 2H), 4.16-4.25 (m, 1H), 4.34 (t, J=4.98, 4.40 Hz, 1H), 4.50 (t, J=4.69 Hz, 1H), 5.48-5.56 (m, 1H).

1-(2-Fluoro-ethyl)-3-(3-hydroxymethyl-cyclohex-2-enyl)-urea: The title urea was obtained from 1-[3-(tert-butyl-dimethyl-silanyloxymethyl)-cyclohex-2-enyl]-3-(2-fluoro-ethyl)-urea (500 mg, 1.5 mmol) and t-butyl ammonium fluoride (1.50 mL, 1.0 M in THF, 1.50 mmol) according to the protocols as outlined in general procedure J. Spectroscopic data: $^1$H NMR (300 MHz, DMSO-d$_6$) δ 1.25-1.38 (m, 1H), 1.42-1.74 (m, 3H), 1.76-1.89 (m, 2H), 3.22 (q, J=5.57, 4.98 Hz, 1H), 3.32 (q, J=5.28 Hz, 1H), 3.75 (d, J=5.57 Hz, 2H), 3.98-4.11 (m, 1H), 4.27 (t, J=5.28 Hz, 1H), 4.43 (t, J=4.98 Hz, 1H), 4.69 (t, J=5.57 Hz, 1H), 5.44-5.48 (m, 1H), 5.85-5.97 (m, 2H). $^{13}$C NMR (75.5 MHz, DMSO-d$_6$) δ 20.17, 25.63, 30.65, 40.40 (d, J=20.65 Hz), 45.05, 65.13, 84.08 (d, J=162.91 Hz), 122.85, 141.13, 157.95.

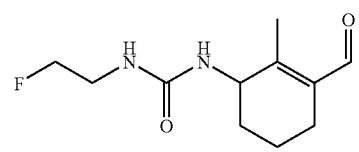

Synthesis of 1-(2-fluoro-ethyl)-3-(3-formyl-2-methyl-cyclohex-2-enyl)-urea

The desired starting material 3-[1,3]dithian-2-yl-2-methyl-cyclohex-2-enone was prepared from the commercially available 2-methyl-cyclohexane-1,3-dione. The dithiane-protected urea was thus generated from this enone according to general procedure I described above. Deprotection of the dithiane functionality afforded the desired final urea. The intermediates 3-ethoxy-2-methyl-cyclohex-2-enone, 3-[1,3]dithian-2-yl-2-methyl-cyclohex-2-enone, 3-[1,3]dithian-2-yl-2-methyl-cyclohex-2-enol, 2-(3-azido-2-methyl-cyclohex-1-enyl)-[1,3]dithiane, 3-[1,3]dithian-2-yl-2-methyl-cyclohex-2-enylamine and 1-(3-[1,3]dithian-2-yl-2-methyl-cyclohex-2-enyl)-3-(2-fluoro-ethyl)-urea were isolated and characterized.

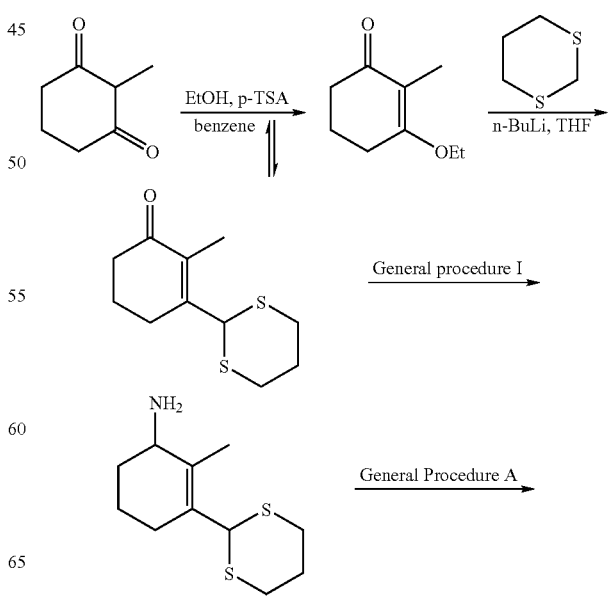

-continued

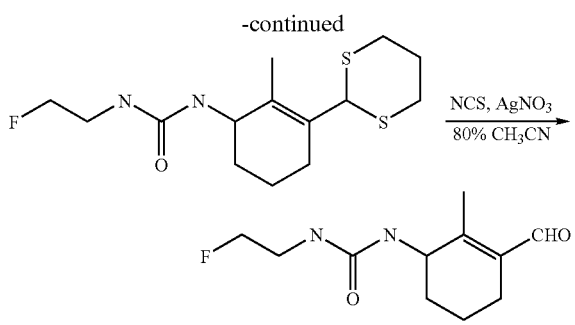

3-Ethoxy-2-methyl-cyclohex-2-enone: A solution of 2-methyl-cyclohexane-1,3-dione (20.00 g, 0.16 mol), EtOH (25.00 mL) and a catalytic amount of p-TSA (500 mg) in benzene was fitted with a Dean-Stark trap and refluxed for 14 hours. The reaction mixture was cooled to room temperature and washed with dilute $NaHCO_3$ (3×150 mL). The $NaHCO_3$ solution was then back-extracted with $Et_2O$ (1×200 mL). The combined ether and benzene fractions was concentrated and purified by column chromatography using hexane:$Et_2O$ (3:2) as the eluant to give 8.96 g (37%) of the title enone. Spectroscopic data: $^1H$ NMR (300 MHz, $CDCl_3$) δ 1.34 (t, J=7.04 Hz, 3H), 1.68-1.72 (m, 3H), 1.91-2.01 (m, 2H), 2.33 (t, J=7.33, 6.16 Hz, 2H), 2.51-2.57 (m, 2H), 4.06 (q, J=7.04 Hz, 2H).

3-[1,3]Dithian-2-yl-2-methyl-cyclohex-2-enone: n-BuLi (36.40 mL, 2.5 M in hexane, 91.00 mmol) was added dropwise to a solution of 1,3-dithiane (11.00 g, 91.50 mmol) in THF at −78° C. The resulting mixture was stirred for 2 hours at this temperature, then a solution of 3-ethoxy-2-methyl-cyclohex-2-enone (14.00 g, 90.90 mmol) in THF was added in a dropwise fashion. The resulting mixture was stirred for 1 hour then warmed to 0° C. It was then quenched with $H_2SO_4$ and stirred for another hour. The resulting mixture was then poured into brine and extracted with $Et_2O$ (3×300 mL). The combined organic extracts were washed with $NaHCO_3$ (1×300 mL) and brine (1×300 mL), then dried over $MgSO_4$ and concentrated. Purification by column chromatography using hexane:EtOAc (4:1) as the eluant gave the desired title enone. Spectroscopic data: $^1H$ NMR (300 MHz, $CDCl_3$) δ 1.87-2.00 (m, 6H), 2.11-2.20 (m, 1H), 2.41 (t, J=7.04 Hz, 2H), 2.52-2.62 (m, 2H), 2.85-2.94 (m, 2H), 2.98-3.09 (m, 2H), 5.22 (s, 1H).

3-[1,3]Dithian-2-yl-2-methyl-cyclohex-2-enol[lxxiii]: 5.63 g (68.7%) of the title compound was obtained from $NaBH_4$ (970 mg, 25.60 mmol), 3-[1,3]dithian-2-yl-2-methyl-cyclohex-2-enone (5.84 g, 25.60 mmol) and $CeCl_3.7H_2O$ (10.50 g, 28.20 mmol) according to the protocols described in general procedure I above. Spectroscopic data: $^1H$ NMR (300 MHz, $CDCl_3$) δ 1.53-1.85 (m, 6H), 1.89 (s, 3H), 2.04-2.17 (m, 2H), 2.21-2.32 (m, 1H), 2.79-2.87 (m, 2H), 2.92-3.04 (m, 2H), 3.93-3.99 (m, 1H), 5.07 (s, 1H).

2-(3-Azido-2-methyl-cyclohex-1-enyl)-[1,3]dithiane: 4.37 g (70%) of the title azido compound was obtained from diphenylphosphoryl azide (6.40 mL, 29.60 mmol), 3-[1,3]dithian-2-yl-2-methyl-cyclohex-2-enol (5.63 g, 24.50 mmol) and DBU (4.40 mL, 29.40 mmol) according to the protocols described in general procedure I. Spectroscopic data: $^1H$ NMR (300 MHz, $CDCl_3$) δ 1.59-1.97 (m, 8H), 2.06-2.21 (m, 2H), 2.27-2.38 (m, 1H), 2.80-2.89 (m, 2H), 2.94-3.06 (m, 2H), 3.67-3.73 (m, 1H), 5.09 (s, 1H).

3-[1,3]Dithian-2-yl-2-methyl-cyclohex-2-enylamine: The title amine was obtained from 2-(3-azido-2-methyl-cyclohex-1-enyl)-[1,3]dithiane (4.37 g, 17.10 mmol), triphenyl phosphine (4.54 g, 17.31 mmol) and KOH (970 mg, 17.29 mmol) according to the protocols described in general procedure I. Spectroscopic data: $^1H$ NMR (300 MHz, $CDCl_3$) δ 1.42-1.71 (m, 3H), 1.74-1.90 (m, 6H), 2.04-2.31 (m, 2H), 2.78-2.87 (m, 3H), 2.90-3.05 (m, 3H), 3.10-3.17 (m, 1H), 5.05-5.10 (m, 1H).

1-(3-[1,3]Dithian-2-yl-2-methyl-cyclohex-2-enyl)-3-(2-fluoro-ethyl)-urea: The title urea was obtained from 3-[1,3]dithian-2-yl-2-methyl-cyclohex-2-enylamine (6.43 g, 28.00 mmol), diimidazole carbonyl (2.80 g, 17.26 mmol), fluoroethyl amine hydrochloride (1.70 g, 90% purity, 15.38 mmol) and diisopropyl ethyl amine (6.00 mL, 34.45 mmol) according to the protocols as outlined in general procedure A. Spectroscopic data: $^1H$ NMR (300 MHz, DMSO-$d_6$) δ 1.42-1.58 (m, 4H), 1.69 (s, 3H), 1.96-2.11 (m, 4H), 2.71-2.81 (m, 2H), 2.97-3.10 (m, 2H), 3.23 (q, J=5.57, 4.98 Hz, 1H), 3.32 (q, J=5.28 Hz, 1H), 3.94-4.05 (m, 1H), 4.28 (t, J=5.28 Hz, 1H), 4.44 (t, J=4.98 Hz, 1H), 5.20 (s, 1H), 5.92 (t, J=5.86 Hz, 1H), 6.03 (d, J=9.09 Hz, 1H).

1-(2-Fluoro-ethyl)-3-(3-formyl-2-methyl-cyclohex-2-enyl)-urea: 1-(3-[1,3]Dithian-2-yl-2-methyl-cyclohex-2-enyl)-3-(2-fluoro-ethyl)-urea (630 mg, 2.00 mmol) dissolved in 3 mL $CH_3CN$ was added to a solution of N-chlorosuccinimide (845 mg, 6.30 mmol) and $AgNO_3$ (1.24 g, 7.30 mmol) in 14 mL of 80% aqueous $CH_3CN$ at 0° C. The reaction mixture was stirred for 30 minutes, and then 3.60 g of $Na_2S_2O_3$ in 7.0 mL of $H_2O$ was added, followed by 4.20 g of $Na_2CO_3$ in 7.0 mL of $H_2O$. The resulting mixture was stirred for 5 minutes and filtered through a pad of celite. The celite was washed with EtOAc and the combined organic phases were washed with brine (1×15 mL), dried over $MgSO_4$ and concentrated. Purification by column chromatography using hexane:EtOAc (4:1) as the eluant gave the desired title urea. Spectroscopic data: $^1H$ NMR (500 MHz, DMSO-$d_6$) δ 1.49-1.58 (m, 3H), 1.60-1.67 (m, 1H), 1.92-2.00 (m, 1H), 2.08-2.14 (m, 4H), 3.29 (q, J=4.88 Hz, 1H), 3.35 (q, J=5.86, 4.88 Hz, 1H), 4.20-4.25 (m, 1H), 4.35 (t, J=4.88 Hz, 1H), 4.45 (t, J=4.88 Hz, 1H), 6.01 (t, J=5.37 Hz, 1H), 6.28 (d, J=8.79 Hz, 1H), 10.1 (s, 1H). $^{13}C$ NMR (126 MHz, DMSO-$d_6$) δ 15.62, 18.72, 22.79, 30.23, 40.62 (d, J=20.14 Hz), 50.08, 84.04 (d, J=163.98 Hz), 134.63, 155.68, 158.31, 193.00.

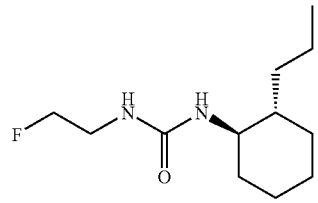

Synthesis of 1-(2-fluoro-ethyl)-3-(2R-propyl-1R-cyclohexyl)-urea:

1-(2-Fluoro-ethyl)-3-(2R-propyl-1R-cyclohexyl)-urea: The title compound was obtained from 2R-propyl-1R-cyclohexylamine (1.40 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure A above. Spectroscopic data: $^1H$ NMR (300 MHz, DMSO-$d_6$) δ ppm 0.76-0.88 (m, 2H) 1.21 (s, 2H) 1.36 (s, 2H) 3.57 (s, 2H) 4.51 (s, 4H) 4.66 (s, 2H) 7.19 (s, 4H) 7.29 (s, 2H) 7.43 (s, 4H) 8.75 (s, 2H).

[i] Siscovic, E. et al. Indian J. Chem. 1968, 6, 400-401.

[ii] Adamczyk, Maciej; Watt, David S.; Netzel, Daniel A. J. Org. Chem. 1984, 49, 4226-4237.

[iii] Colette; Perrot Helv. Chim. Acta 1977, 60, 2089-2094.

[iv] Tombari, D. G.; Moglioni, A. G.; Iglesias, G. Y. Moltrasio *Org. Prep. Proced. Int.* 1995, 27, 671-674.

[v] Nakada et al. *Agric. Biol. Chem.* 1978, 42, 1365-1372.

[vi] Mattson, Ronald J.; Catt, John D.; Keavy, Daniel; Sloan, Charles P.; Epperson, James; Gao, Qi; Hodges, Donald B.; Iben, Lawrence; Mahle, Cathy D.; Ryan, Elaine; Yocca, Frank D. *Bioorg. Med. Chem. Lett.* 2003, 13, 1199-1202.

[vii] Nguy, Nim Ming; Chiu, I. C.; Kohn, Harold *J. Org. Chem.* 1987, 52, 1649-1655.

[viii] Adcock, W. et al. *J. Organomet. Chem.* 1975, 102; 297-311.

[ix] Lewschina; Kolodkina J. Gen. Chem. USSR (Engl. Transl.) 1960, 30, 3656; *Zh. Obshch. Khim.* 1960, 30, 3692. Borne, R. F. et al. *J. Med. Chem.* 1977, 20, 771-776.

[xi] Novak; Protiva *CCCCAK; Collect. Czech. Chem. Commun.* 1962, 27, 2413, 2416.

[xii] Musso, David L.; Cochran, Felicia R.; Kelley, James L.; McLean, Ed W.; Selph, Jeffrey L.; Rigdon, Greg C.; Orr, G. Faye; Davis, Ronda G.; Cooper, Barrett R.; Styles, Virgil L.; Thompson, James B.; Hall, William R. *J. Med. Chem.* 2003, 46, 399-408.

[xiii] Patent; Eli Lilly and Co.; Indianapolis; Ind. (V.St.A); DE 2812578; 1978; Chem.Abstr., 90, 54730.

[xiv] Adamczyk, Maciej; Watt, David S.; Netzel, Daniel A. *J. Org. Chem.* 1984, 49, 4226-4237.

[xv] Immer, H.; Bagli, J. F. *J. Org. Chem.* 1968, 33, 2457-2462.

[xvi] Landsiedel-Maier, Dorothea; Frahm, August Wilhelm *Arch. Pharm.* (Weinheim Ger.) 1998, 331, 59-71.

[xvii] Nakamura, Y.; O-kawa, K.; Minami, S.; Ogawa, T.; Tobita, S.; Nishimura, J. *J. Org. Chem.* 2002, 67, 1247-1252.

[xviii] Cope, A. C.; Liss, T. A.; Smith, D. S. *J. Am. Chem. Soc.* 1957, 79, 240-243.

[xix] a.) Bartmann, W.; Konz, E.; Ruger, W. *J. Het. Chem.* 1987, 24, 677-682.
b.) Sircar, I.; Duell, B. L.; Cain, M. H.; Burke, S. E.; Bristol, J. A. *J. Med. Chem.* 1986, 29, 2142-2148. For AlCl$_3$/NaCl cyclization.

[xx] a.) Bartmann, W.; Konz, E.; Ruger, W. *J. Het. Chem.* 1987, 24, 677-682.
b.) Sircar, I.; Duell, B. L.; Cain, M. H.; Burke, S. E.; Bristol, J. A. *J. Med. Chem.* 1986, 29, 2142-2148. For AlCl$_3$/NaCl cyclization.

[xx] Bartmann, Wilhelm; Konz, Elmar; Rueger, Wolfgang; JHTCAD; J. Heterocycl. Chem.; EN; 24; 1987; 677-682.

[xxii] Johnson, M. P.; Frescas, S. P.; Oberlender, R.; Nichols, D. E. *J. Med. Chem.* 1991, 34, 1662-1668.

[xxiii] Haadsma-Svensson, Susanne; Cleek, Kerry A.; Dinh, Dac M.; Duncan, J. Neil; Haber, Christopher L.; Huff, Rita M.; Lajiness, Mary E.; Nichols, Nanette F.; Smith, Martin W.; Svensson, Kjell A.; Zaya, Matt J.; et al. *J. Med. Chem.* 2001, 44, 4716-4732.

[xxiv] Simchen, G.; Kraemer, W. *Chem. Ber.* 1969, 102, 3656-3665.

[xxv] Colette; Perrot *Helv. Chim. Acta* 1977, 60, 2089-2094.

[xxvi] Simchen, G.; Kraemer, W. *Chem. Ber.* 1969, 102, 3656-3665.

[xxvii] Stratford, E. S. et al. *J. Pharm. Sci.* 1978, 67, 80-83.

[xxviii] Vaccaro, W.; et al. *J. Med. Chem.* 1996, 39, 1704-1719.

[xxix] Hahn, R. C. et al. *J. Am. Chem. Soc.* 1971, 93, 5816-5820.

[xxx] Thummel, Randolph P.; Lefoulon, Francois; Cantu, David; Mahadevan, Ramanathan *J. Org. Chem.* 1984, 49, 2208-2212.

[xxxi] Caprathe, Bradley W.; Jaen, Juan C.; Wise, Lawrence D.; Heffner, Thomas G.; Pugsley, Thomas A.; et al. *J. Med. Chem.* 1991, 34, 2736-2746.

[xxxii] Clemo, G. R.; Groves, L. H.; Munday, L.; Swan, G. A. *J. Chem. Soc.* 1951, 863-867.

[xxxiii] Seidl, G. et al. *Tetrahedron* 1964, 20, 633-640.

[xxxiv] Askam, V.; Linnell, W. H. *J. Chem. Soc.* 1954, 4691-4693.

[xxxv] Ranade, V. S.; Consiglio, G.; Prins, R. *J. Org. Chem.* 1999, 64, 8862-8867.

[xxxvi] Perrone, Roberto; Berardi, Francesco; Leopoldo, Marcello; Tortorella, Vincenzo; Formaretto, Maria Gioia; et al. *J. Med. Chem.* 1996, 39, 3195-3202.

[xxvii] Vaccaro, W.; et al. *J. Med. Chem.* 1996, 39, 1704-1719.

[xxxviii] Sarges et al. *J. Med. Chem.* 1973, 16, 1003, 1004.

[xxxix] Stipanovic, B.; Pines, H. *J. Org. Chem.* 1969, 34, 2106-2113.

[xl] Staab, Heinz A.; Nikolic, Susanne; Krieger, Claus *Eur. J. Org. Chem.* 1999, 6, 1459-1470.

[xli] Zhang, Xiaoyan; Angeles, Joseph E. De Los; He, Mei-Ying; Dalton, James T.; Shams, Gamal; et al. *J. Med. Chem.* 1997, 40, 3014-3024.

[xlii] Houghton, Roy P.; Shervington, Leroy A. *J. Chem. Res. Miniprint* 1989, 8, 1872-1892.

[xliii] Bunnett, J. F.; Skorcz, J. A. *J. Org. Chem.* 1962, 27, 3836-3843.

[xliv] Kuiban et al. *J. Gen. Chem. USSR (Engl. Transl.)* 1964, 34, 1592; *Zh. Obshch. Khim.* 1964, 34, 1581.

[xlv] Burnham, J. W. et al. *J. Org. Chem.* 1974, 39, 1416-1420.

[xlvi] Ksander, Gary M.; Jesus, Reynalda de; Yuan, Andrew; Ghai, R. D.; Trapani, A.; et al. *J. Med. Chem.* 1997, 40, 495-505.

[xlvii] Wolfe, John P.; Rennels, Roger A.; Bulchwald, Stephen L. *Tetrahedron* 1996, 52, 7525-7546.

[xlviii] Adamczyk, Maciej; Watt, David S.; Netzel, Daniel A. *J. Org. Chem.* 1984, 49, 4226-4237.

[xlix] Houghton, Roy P.; Voyle, Martyn; Price, Raymond *J. Chem. Soc. Perkin Trans. I* 1984, 5, 925-931.

[l] Houghton, Roy P.; Voyle, Martyn; Price, Raymond *J. Organomet. Chem.* 1983, 259, 183-188.

[li] Cauquil-Caubere, Isoline; Kamenka, Jean-Marc *Eur. J. Med. Chem. Chim. Ther.* 1998, 33, 867-878.

[lii] Cannon, Joseph G.; Perez, Julio A.; Pease, Jonathan P; Long, John Paul; Flynn, Jan R.; et al. *J. Med. Chem.* 1980, 23, 745-749.

[liii] Vejdelek, Z. J.; Protiva, M. *CCCCAK; Collect. Czech. Chem. Commun.* 1971, 36, 1611-1623.

[liv] Ward, Dale E.; Rhee, Chung K. *Can. J. Chem.* 1989, 67, 1206-1211.

[lv] Leblanc, Y.; Zamboni, R.; Bernstein, M. A. *J. Org. Chem.* 1991, 56, 1971-1972.

[lvi] Baldwin, Steven W.; Tomesch, John C. *J. Org. Chem.* 1980, 45, 1455-1462.

[lvii] Berube, Gervais; Fallis, Alex G. *Can. J. Chem.* 1991, 69, 77-83.

[lviii] Russell, G. A. et al. *J. Am. Chem. Soc.* 1971, 93, 1452-1466.

[lix] Leblanc, Y.; Zamboni, R.; Bernstein, M. A. *J. Org. Chem.* 1991, 56, 1971-1972.

[lx] Ito, Satoru; Kasai, Masaji; Ziffer, Herman; Silverton, J. V. *Can. J. Chem.* 1987, 65, 574-582.

[lxi] Braun, H.; Felber, H.; Kresse, G.; Ritter, A.; Schmidtchen, F. P.; Schneider, A. *Tetrahedron* 1991, 47, 3313-3328.

[lxii] Organ, Michael G.; Murray, Aaron P. *J. Org. Chem.* 1997, 62, 1523-1526.

[lxiii] Laurent, Andre; Mison, Pierre; Nafti, Abdelhafid; Ben Cheikh, Ridha; Chaabouni, Rifaat *J. Chem. Res. Miniprint* 1984, 11, 3165-3194.

[lxiv] Barnier, Jean-Pierre; Morisson, Veronique; Volle, Isabelle; Blanco, Luis *Tetrahedron: Asymmetry* 1999, 10, 1107-1118.

[lxv] Mizuno, Masanori; Shioiri, Takayuki *Chem. Commun.* 1997, 22, 2165-2166.

[lxvi] Pau, Amedeo; Cerri, Riccardo; Boatto, Gianpiero; Palomba, Michele; Pintore, Giorgio; et al. *Farmaco* 1997, 52, 93-98.

[lxvii] Carrea, Giacomo; Danieli, Bruno; Palmisano, Giovanni; Riva, Sergio; Santagostino, Marco *Tetrahedron: Asymmetry* 1992, 3, 775-784.

[lxviii] Adlerova et al. *CCCCAK; Collect. Czech. Chem. Commun.* 1958, 23, 681-688.

[lxix] Srikrishna, A.; Viswajanani, R.; Sattigeri, J. A. *Tetrahedron: Asymmetry* 2003, 14, 2975-2984.

[lxx] Callis, David J.; Thomas, Noel F.; Pearson, David P. J.; Potter, Barry V. L. *J. Org. Chem.* 1996, 61, 4634-4640.

[lxxi] Kuwahara, Shigefumi; Suzuki, Katsuyuki; Hiramatsu, Akira *Biosci. Biotechnol Biochem.* 1992, 56, 1510-1511.

[lxxii] Shoji, Mitsuru; Imai, Hiroki; Shiina, Isamu; Kakeya, Hideaki; Osada, Hiroyuki; Hayashi, Yujiro *J. Org. Chem.* 2004, 69, 1548-1556.

[lxxiii] Hua, Duy H.; Chen, Yi; Sin, Hong-Sig; Maroto, Maria J.; Robinson, Paul D.; et al. *J. Org. Chem.* 1997, 62, 6888-6896.

What is claimed is:

1. A compound having the formula

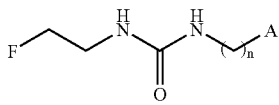

or a pharmaceutically acceptable salt thereof;
wherein n is 0 or 1; and
A is 5 to 7-membered cycloalkenyl optionally fused to an aromatic ring;
wherein A has 0, 1, 2, 3, or 4 substituents;
said substituents each independently consisting of: a moiety consisting of from 0 to 8 carbon atoms, 0 or 1 nitrogen atoms, 0 or 1 oxygen atoms, 0 or 1 sulfur atoms, 0 to 3 fluorine atoms, and from 0 to 22 hydrogen atoms; F; Cl; Br; or I;
provided that A is not unsubstituted 2-cyclohexen-1-yl.

2. The compound of claim 1 having the formula

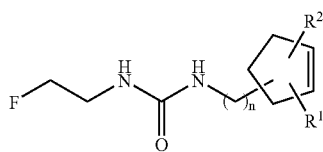

or a pharmaceutically acceptable salt thereof;
wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I.

3. The compound of claim 1 having the formula

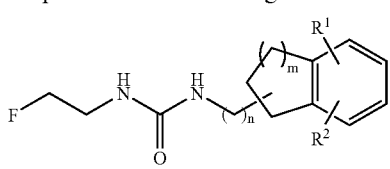

or a pharmaceutically acceptable salt thereof;
wherein $R^1$ and $R^2$ are substituents which independently consist of: a moiety consisting of from 0 to 3 carbon atoms, 0 or 1 oxygen atoms, and from 0 to 9 hydrogen atoms; F; Cl; Br; or I; and
m is 1, 2, or 3.

4. The compound according to claim 1 having the formula

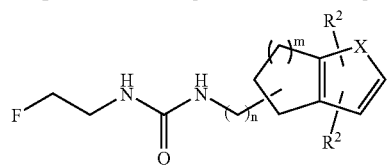

or a pharmaceutically acceptable salt thereof;
wherein X is S, N, or O;
$R^1$ and $R^2$ are substituents which independently consist of: a moiety consisting of from 0 to 3 carbon atoms, 0 or 1 oxygen atoms, and from 0 to 9 hydrogen atoms;
F; Cl; Br; or I; and
m is 1, 2, or 3.

5. The compound according to claim 1 wherein A is cyclopentenyl optionally fused to an aromatic ring.

6. The compound according to claim 1 wherein A is cyclohexenyl optionally fused to an aromatic ring.

7. The compound according to claim 1 wherein A is tetrahydronaphthylenyl.

8. The compound according to claim 1 wherein A is cycloheptenyl optionally fused to an aromatic ring.

9. The compound according to claim 1 wherein A has 0, 1, or 2 substituents.

10. The compound of claim 9 wherein the substituents are independently $C_{1-3}$ alkyl, $C_{1-3}$ alkoxy, F, Cl, Br, I, or $NH_2$.

11. The compound according to claim 1 wherein n is 0.

12. The compound according to claim 1 wherein n is 1.

13. The compound according to claim 1 selected from
1-(2-fluoro-ethyl)-3-indan-2-yl-urea;
1-(2-Fluoro-ethyl)-3-indan-1-yl-urea;
(R)-(−)-1-(2-Fluoro-ethyl)-3-indan-1-yl-urea;
(S)-(−)-1-(2-Fluoro-ethyl)-3-indan-1-yl-urea;
1-(2-fluoroethyl)-3-(3-methylindan-1-yl)urea;
1-(2-fluoro-ethyl)-3-(2-methyl-indan-1-yl)-urea;
1-(2-fluoro-ethyl)-3-(4-methyl-indan-1-yl)-urea;
1-(2-fluoro-ethyl)-3-(6-methyl-indan-1-yl)-urea;
1-(2-fluoro-ethyl)-3-(6-methoxy-indan-1-yl)-urea;
1-(2-fluoro-ethyl)-3-(5-fluoro-indan-1-yl)-urea;
1-(2-fluoro-ethyl)-3-(4-methoxy-indan-1-yl)-urea;
1-(2-fluoro-ethyl)-3-(5-methoxy-indan-1-yl)-urea;
1-(5-chloro-indan-1-yl)-3-(2-fluoro-ethyl)-urea;
1-(5-bromo-indan-1-yl)-3-(2-fluoro-ethyl)-urea;
1-(2-fluoro-ethyl)-3-(6-fluoro-indan-1-yl)-urea;
1-(4-chloro-indan-1-yl)-3-(2-fluoro-ethyl)-urea;
1-(4-bromo-indan-1-yl)-3-(2-fluoro-ethyl)-urea;
1-(2-fluoro-ethyl)-3-(4-fluoro-indan-1-yl)-urea;
1-(2-fluoro-ethyl)-3-(7-methoxy-indan-1-yl)-urea;
1-(6-bromo-indan-1-yl)-3-(2-fluoro-ethyl)-urea;
1-(6-chloro-indan-1-yl)-3-(2-fluoro-ethyl)-urea;
1-(2-fluoro-ethyl)-3-(7-methyl-indan-1-yl)-urea;
1-(2-fluoro-ethyl)-3-(5-methyl-indan-1-yl)-urea;
1-(4-ethyl-indan-1-yl)-3-(2-fluoro-ethyl)-urea;
1-(2-fluoro-ethyl)-3-(7-fluoro-indan-1-yl)-urea;
1-(7-bromo-indan-1-yl)-3-(2-fluoro-ethyl)-urea;
1-(7-chloro-indan-1-yl)-3-(2-fluoro-ethyl)-urea;
1-(6,7-dichloro-indan-1-yl)-3-(2-fluoro-ethyl)-urea;
1-(6,7-difluoro-indan-1-yl)-3-(2-fluoro-ethyl)-urea;
1-(6,7-dimethyl-indan-1-yl)-3-(2-fluoro-ethyl)-urea;

1-(6-chloro-7-methyl-indan-1-yl)-3-(2-fluoro-ethyl)-urea;
1-(6-bromo-7-methyl-indan-1-yl)-3-(2-fluoro-ethyl)-urea;
1-(2-fluoro-ethyl)-3-(5-methoxy-indan-2-yl)-urea;
1-(2-fluoro-ethyl)-3-(4-methyl-indan-2-yl)-urea;
1-(2-fluoro-ethyl)-3-(4-methoxy-indan-2-yl)-urea;
1-(2-fluoro-ethyl)-3-(5-methyl-indan-2-yl)-urea;
1-(4-bromo-indan-2-yl)-3-(2-fluoro-ethyl)-urea;
1-(2-fluoro-ethyl)-3-(4-fluoro-indan-2-yl)-urea;
1-(2-fluoro-ethyl)-3-(5-fluoro-indan-2-yl)-urea;
1-(4-Chloro-indan-2-yl)-3-(2-fluoro-ethyl)-urea;
1-(5-chloro-indan-2-yl)-3-(2-fluoro-ethyl)-urea;
1-({[(2-fluoroethyl)amino]carbonyl}amino)-2,3-dihydro-1H-inden-4-yl benzoate;
1-(2-fluoroethyl)-3-(4-hydroxy-2,3-dihydro-1H-inden-1-yl)urea;
1-(4-amino-indan-1-yl)-3-(2-fluoro-ethyl)-urea;
1-(6,7-dihydro-5H-[1]pyrindin-7-yl)-3-(2-fluoro-ethyl)-urea;
1-(6,7-dihydro-5H-[1]pyrindin-5-yl)-3-(2-fluoro-ethyl)-urea;
1-(2-Fluoro-ethyl)-3-indan-1-ylmethyl-urea;
1-(2-fluoro-ethyl)-3-(5-methoxy-1,2,3,4-tetrahydro-naphthalen-1-yl)-urea;
1-(2-fluoro-ethyl)-3-(7-methoxy-1,2,3,4-tetrahydro-naphthalen-1-yl)-urea;
1-(2-fluoro-ethyl)-3-(4-methyl-1,2,3,4-tetrahydro-naphthalen-1-yl)-urea;
1-(5,7-Dimethyl-1,2,3,4-tetrahydro-naphthalen-1-yl)-3-(2-fluoro-ethyl)-urea;
1-(2-fluoro-ethyl)-3-(5-methyl-1,2,3,4-tetrahydro-naphthalen-1-yl)-urea;
1-(5-chloro-1,2,3,4-tetrahydro-naphthalen-1-yl)-3-(2-fluoro-ethyl)-urea;
1-(5-ethyl-1,2,3,4-tetrahydro-naphthalen-1-yl)-3-(2-fluoro-ethyl)-urea;
1-(5-bromo-1,2,3,4-tetrahydro-naphthalen-1-yl)-3-(2-fluoro-ethyl)-urea;
1-(2-fluoro-ethyl)-3-(5-fluoro-1,2,3,4-tetrahydro-naphthalen-1-yl)-urea;
1-(2-fluoroethyl)-3-(4,5,6,7-tetrahydro-1-benzofuran-4-yl)urea;
1-(2-fluoroethyl)-3-(4,5,6,7-tetrahydro-1-benzothien-4-yl)urea;
1-(2-fluoro-ethyl)-3-(1,2,3,4-tetrahydro-naphthalen-2-yl)-urea;
1-(2-fluoro-ethyl)-3-(6,7,8,9-tetrahydro-5H-benzocyclohepten-5-yl)-urea;
1-(2-fluoro-ethyl)-3-(3-fluoro-6,7,8,9-tetrahydro-5H-benzocyclohepten-5-yl)-urea;
1-(2-fluoro-ethyl)-3-(3-methyl-cyclopent-2-enyl)-urea;
1-(2,3-Dimethyl-cyclopent-2-enyl)-3-(2-fluoro-ethyl)-urea;
1-(3-ethyl-2-methyl-cyclopent-2-enyl)-3-(2-fluoro-ethyl)-urea;
1-(2-fluoro-ethyl)-3-(2-methyl-cyclohex-2-enyl)-urea;
1-(2-ethyl-cyclohex-2-enyl)-3-(2-fluoro-ethyl)-urea;
1-(2-fluoro-ethyl)-3-(3-methyl-cyclohex-2-enyl)-urea;
1-(3-Ethyl-cyclohex-2-enyl)-3-(2-fluoro-ethyl)-urea;
1-(2,3-dimethyl-cyclohex-2-enyl)-3-(2-fluoro-ethyl)-urea;
1-(2-Fluoro-ethyl)-3-(3-hydroxymethyl-cyclohex-2-enyl)-urea;
1-(2-fluoro-ethyl)-3-(3-formyl-2-methyl-cyclohex-2-enyl)-urea; and
1-(2-fluoro-ethyl)-3-(2R-propyl-1R-cyclohexyl)-urea.

14. A method of treating pain comprising administering a compound according to claim 1 to a mammal in need thereof.

15. The method of claim 14 wherein the pain is chronic pain.

16. The method of claim 14 wherein the pain is neuropathic pain.

17. The method of claim 14 wherein the pain is visceral pain.

18. The method of claim 14 wherein the pain is associated with allodynia.

19. The method of claim 14 wherein the pain is associated with muscle spasticity.

20. The method of claim 14 wherein the pain is associated with diarrhea.

21. A dosage form comprising a compound of claim 1 and a pharmaceutically acceptable excipient.

* * * * *